United States Patent [19]

Kundu et al.

[11] Patent Number: 5,174,959
[45] Date of Patent: Dec. 29, 1992

[54] BREATH COMPONENT MONITORING DEVICE

[75] Inventors: Samar K. Kundu; Richard W. George; Steven C. March, all of Libertyville; Sangvorn Rutnarak, Long Grove, all of Ill.

[73] Assignee: Abbott Laboratories, Abbott Park, Ill.

[21] Appl. No.: 685,317

[22] Filed: Apr. 15, 1991

Related U.S. Application Data

[60] Division of Ser. No. 131,811, Dec. 17, 1987, Pat. No. 5,071,769, which is a continuation-in-part of Ser. No. 944,083, Dec. 22, 1986, Pat. No. 4,970,172.

[51] Int. Cl.⁵ ............................................. G01N 31/22
[52] U.S. Cl. ........................................ 422/59; 422/58; 422/61; 422/84; 422/85; 436/128; 436/132; 436/167; 436/181
[58] Field of Search ................ 422/58, 59, 84, 85, 422/61; 436/128, 132, 167, 181

[56] References Cited

U.S. PATENT DOCUMENTS 3,196,689 7/1965 Forrester et al. .................. 422/85 X Primary Examiner—Jill A. Johnston
Attorney, Agent, or Firm—Frank S. Ungemach; Jeffrey Sharp

[57] ABSTRACT

The present invention relates to methods and materials for the detection of ketone and aldehyde analytes in fluid samples by means of reacting analyte containing samples with a first solid matrix material to which a nitroprusside salt is coupled and a second solid matrix material to which an amine is covalently coupled. Methods and devices are also provided for ascertaining the fat catabolism effects of a weight loss dietary regimen comprising determining the breath acetone concentration of the subject.

15 Claims, 21 Drawing Sheets

WEIGHT, WATER AND FAT LOSS PROFILE OF
0-10 LBS. OVERWEIGHT DIETERS

WEIGHT, WATER AND FAT LOSS PROFILE OF 10-20 LBS. OVERWEIGHT DIETERS

WEIGHT, WATER AND FAT LOSS PROFILE OF 20-40 LBS. OVERWEIGHT DIETERS

WEIGHT, WATER AND FAT LOSS PROFILE OF 40-100 LBS. OVERWEIGHT DIETERS

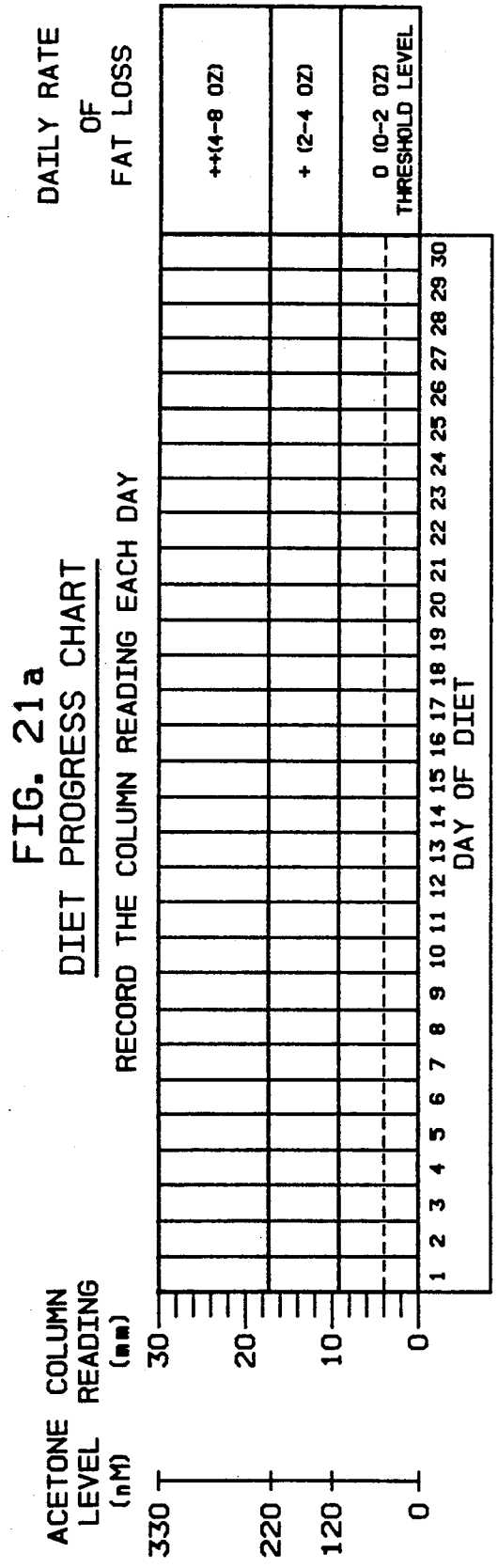
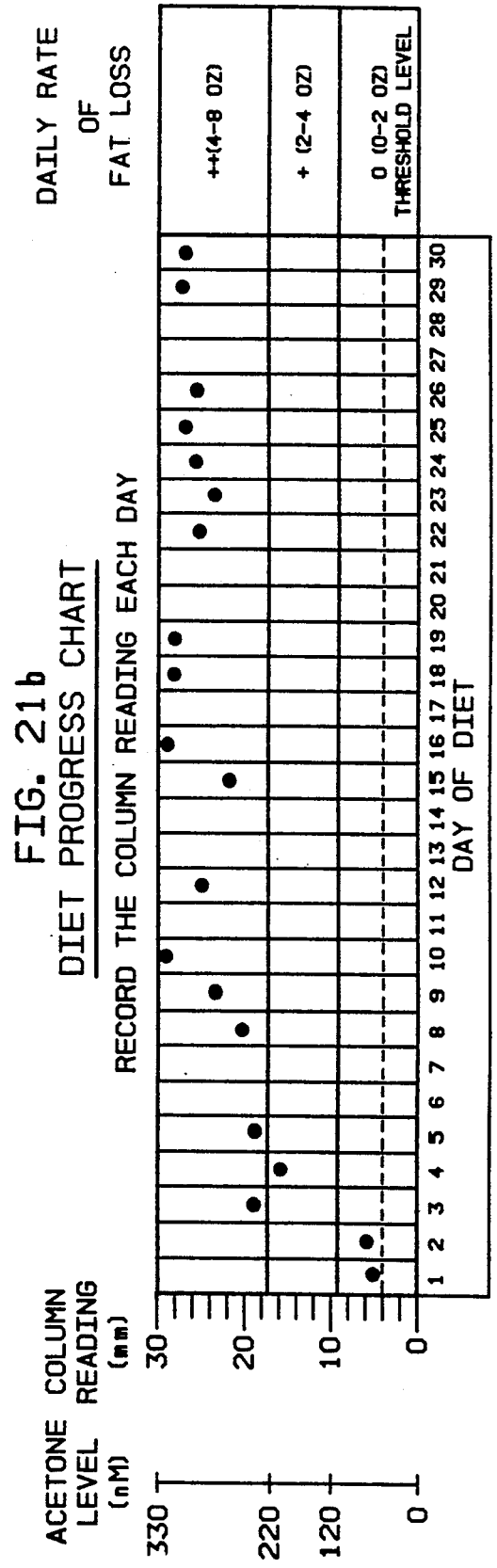

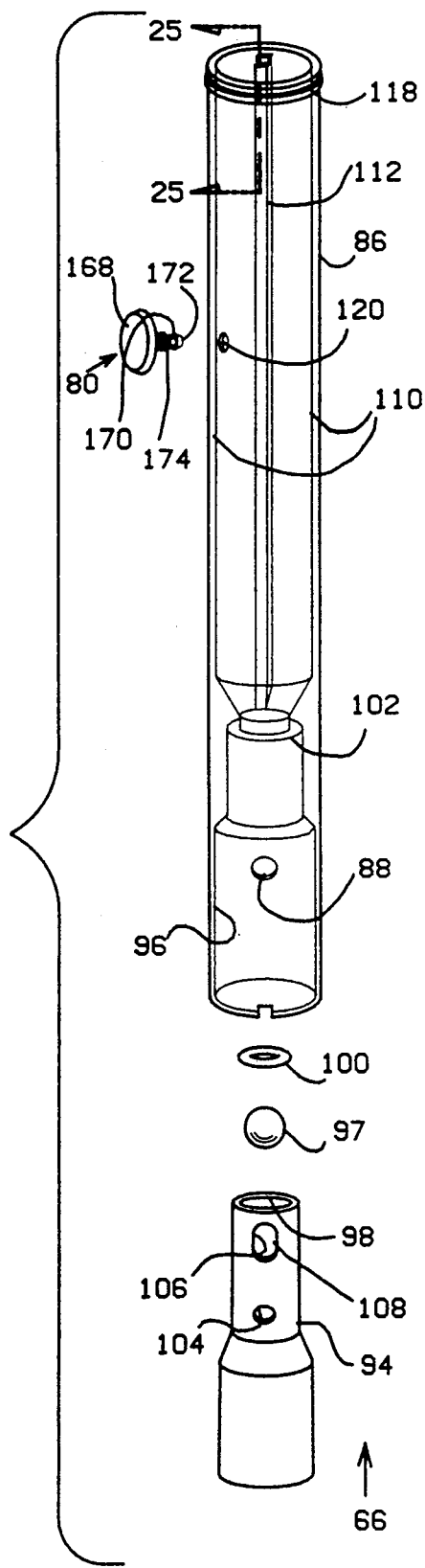
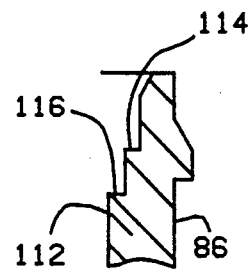
FIG. 25
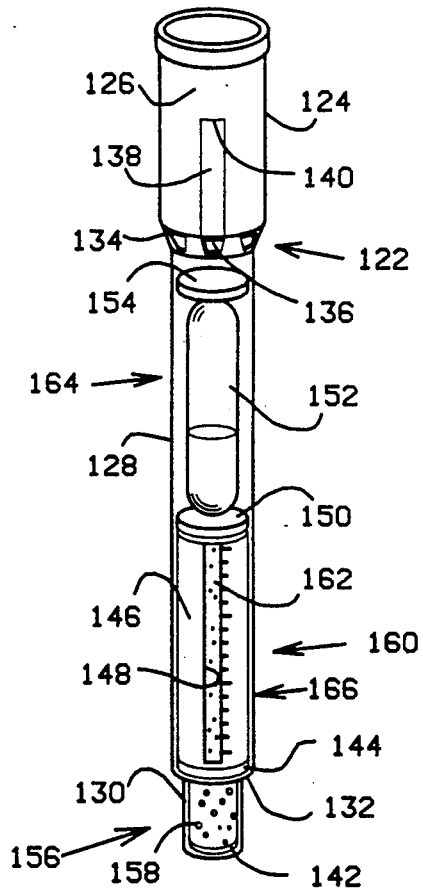
FIG. 26
FIG. 24

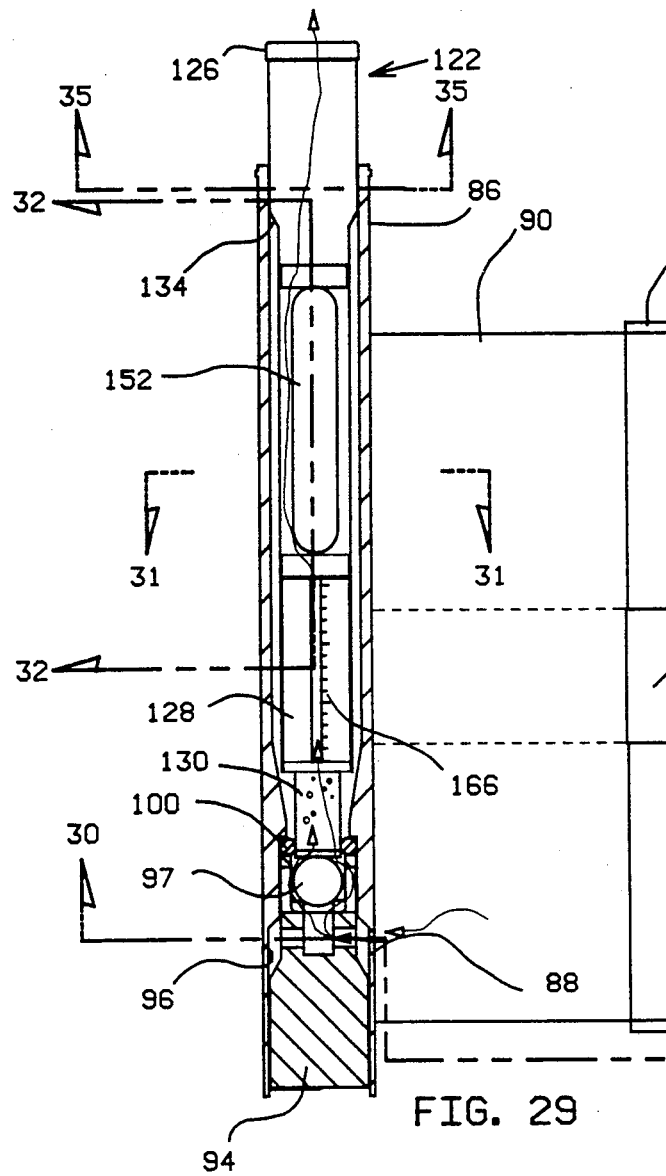
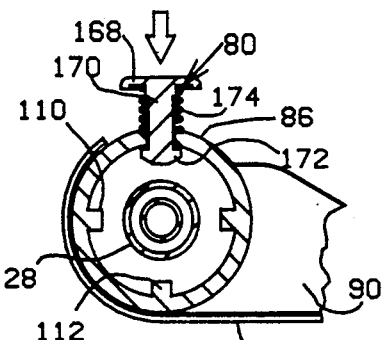
FIG. 31
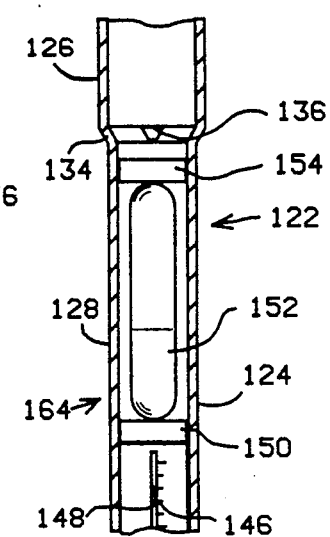
FIG. 32
FIG. 29
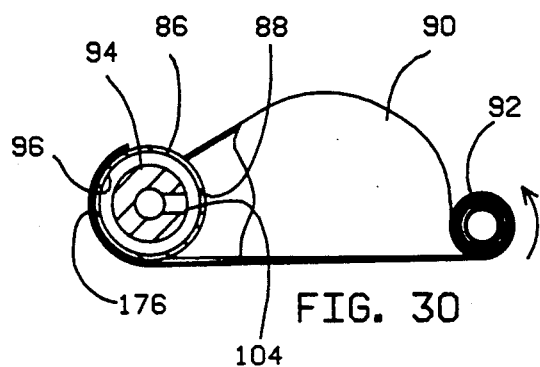
FIG. 30
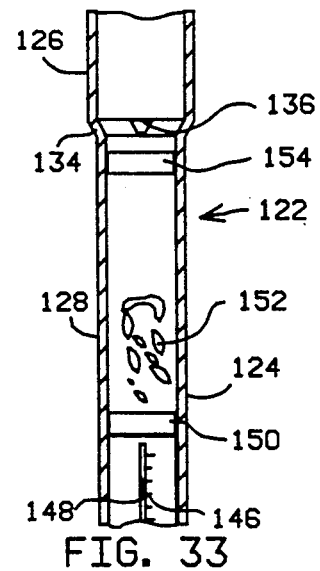
FIG. 33

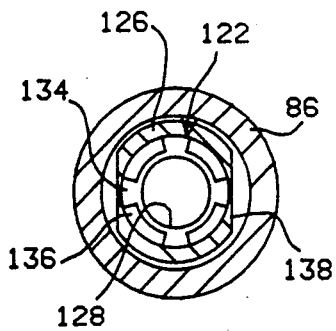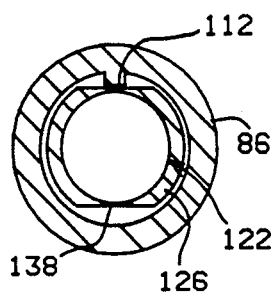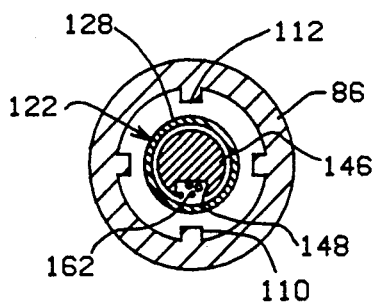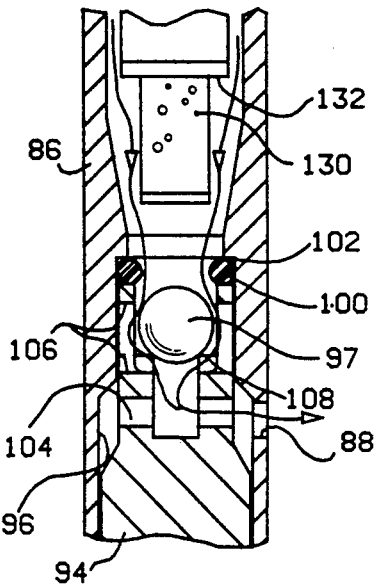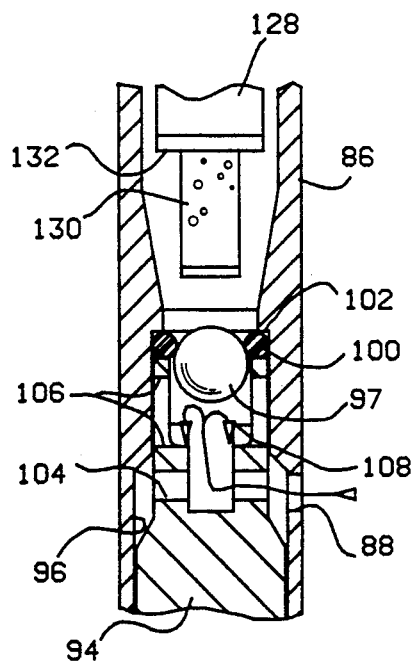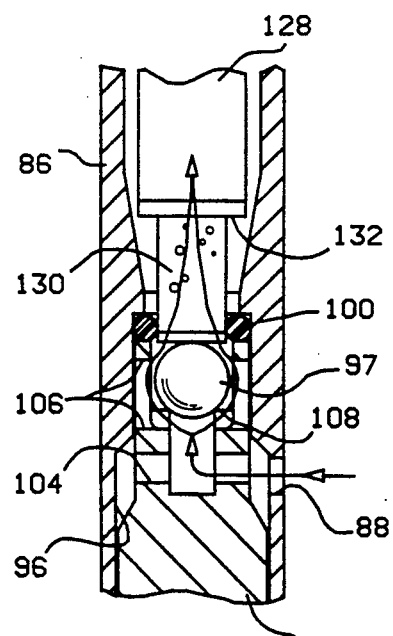

BREATH COMPONENT MONITORING DEVICE

This is a divisional of U.S. patent application Ser. No. 07/131,811, filed Dec. 17, 1987, now U.S. Pat. No. 5,071,769, issued Dec. 10, 1991 which is a continuation-in-part of U.S. patent application Ser. No. 06/944,083, filed on Dec. 22, 1986, now U.S. Pat. No. 4,970,172, issued Nov. 13, 1990.

BACKGROUND

The present invention relates generally to methods and materials for the detection of ketones and aldehydes in fluid (liquid or vapor) samples. The invention is particularly directed to the quantitative determination of ketone and aldehyde concentrations in physiological fluids including blood, urine and breath samples. The invention further relates to methods and materials for monitoring the effects of diet, exercise and diabetic conditions through the quantitative measurement of breath acetone levels.

It is known that "ketone bodies" by which term is generally meant acetone, acetoacetic acid and β-hydroxybutyric acid, tend to accumulate in the blood stream during periods of relative or absolute carbohydrate deprivation due to the breakdown of storage triglycerides. The process through which overproduction of ketone bodies occurs is not well defined but is related to increased oxidation of long chain fatty acids by the liver. Specifically, acetoacetic acid and β-hydroxybutyric acid are formed by the liver as intermediates during the oxidation of fatty acid molecules by acetoacetyl coenzyme A. Acetone is formed from the spontaneous decarboxylation of acetoacetic acid. Under normal conditions the intermediate products are further degraded to carbon dioxide and water and the ketone products do not appear at significant concentrations in the bloodstream. Nevertheless, certain metabolic and disease states interfere with the normal degradation of these intermediates which then accumulate in the bloodstream as a result.

The quantitative measurement of ketone concentrations in blood serum is important because of the relationship between elevated serum ketone levels and clinical conditions such as diabetes, disorders of the digestive organs, renal insufficiency, uremia and malignant carcinoma. In the course of these disorders, ketone bodies pass into the blood stream and a state of metabolic acidosis (ketosis) occurs. Monitoring for the onset of ketosis is of particular importance in the maintenance of diabetics because the occurrence of ketosis may indicate the need for modification of insulin dosage or other disease management.

The concentration and identity of various ketone and aldehyde components present in the serum may be determined by direct chemical or chromatographic analysis. While such direct analysis provides the most accurate determination of serum ketone and aldehyde concentrations it suffers from numerous deficiencies including the requirement that blood be drawn to provide serum for analysis. Moreover, the analysis must be carried out promptly due to decomposition of acetoacetic acid to acetone during storage. In addition, the analysis of blood serum for ketones and aldehydes by chemical means requires the use of various reagents and procedures which can be complex and inconvenient for consumer use. Further, the use of certain chromatographic techniques such as gas chromatography is often impractical for consumer and many types of professional use.

As a consequence of the limitations of measuring serum ketone levels directly, a large body of art has developed directed to the testing of urine for the presence of ketone bodies. It is known that the concentration of ketone bodies in urine bears an imperfect relationship to serum ketone concentrations. While urine ketone concentrations depend on numerous factors and are not always directly proportional to serum ketone concentrations, testing of urine for ketones is a simple and relatively inexpensive means of monitoring serum ketone concentrations. Such methods are in widespread use by diabetics in both home and clinical settings.

A number of test devices and methods for the determination of urine ketone concentrations are known to the art. Some assays utilize the reaction of acetone with salicylaldehyde in alkaline solution to give the deeply colored orange to red compound salicylalacetone. Any acetoacetic acid in such solutions is converted by the alkali to acetone which further contributes to the color reaction.

Kamlet, U.S. Pat. No. 2,283,262 discloses compositions for the detection of acetone and acetoacetic acid in solutions such as urine. The materials comprise a dry mixture of a member of the group consisting of the alkali metal and alkali-earth metal bisulfite addition products of salicylaldehyde and a member of the group consisting of the alkali metal and alkali-earth metal oxides and hydroxides.

Many assays take advantage of the "Legal" method which utilizes the reaction of a carbonyl group containing compound such as a ketone or an aldehyde with a nitroprusside (nitroferricyanide) salt in the presence of an amine to form a colored complex. While acetone will react, albeit slowly, with nitroprusside under aqueous conditions, the reaction of acetoacetic acid is some 100 to 200 times faster with the result that "Legal" reactions under aqueous conditions whether detecting "acetone," "acetone bodies" or "ketone bodies" primarily detect acetoacetic acid. The color reaction is believed to occur as a result of a coupling reaction through the nitroso group of the nitroprusside with the analyte to form an intermediate which then complexes with the amine to produce a color characteristic of the specific amine. In forming the complex, the trivalent iron of the nitroprusside is reduced to its divalent state. The color complex, however, is unstable because nitroprusside decomposes rapidly in alkaline solutions. Further, nitroprusside salts are subject to decomposition in the presence of moisture and high pH. Frequently during storage, a brown decomposition product is formed which can interfere with sensitive detection during assays. These limitations have led to numerous attempts to stabilize the color complex by utilizing mixtures of nitroprussides and amines or amino acids in combination with a variety of buffers, metal salts, organic salts, organic stabilizers and polymers. Numerous combinations of reagents have been shown to be suitable for detection of a variety of ketone bodies in liquid samples although the analyte predominantly detected in physiological fluids is acetoacetic acid.

Fortune, U.S. Pat. No. 2,186,902 discloses the use of soluble nitroprusside chromogens in the presence of ammonia and soluble carbonates for the detection of what was termed "acetone" (actually acetoacetic acid) in urine samples. Varying colorations are observable for the quantitative determination of "acetone" levels.

Galat, U.S. Pat. No. 2,362,478 discloses a solid reagent for the detection of "acetone" (actually acetoacetic acid) in liquid samples. The reagent comprises a dry mixture of a powdered anhydrous soluble nitroprusside, granular anhydrous soluble nitroprusside and granular anhydrous ammonium sulfate. The reagent signals the presence of "acetone" by producing a color reaction when a drop of sample is added thereto.

Free, U.S. Pat. No. 2,509,140 discloses improvements on the materials of Fortune comprising solid dry formulations which may be in the form of tablets for the detection of "acetone bodies" or "ketone bodies" in liquids. The materials comprise a nitroprusside salt, glycine and an alkaline salt.

Nicholls, et al., U.S. Pat. No. 2,577,978 discloses improvements on the dry formulations of Free for the detection of "acetone bodies" or "ketone bodies" in bodily fluids. Such compositions comprise alkali metal nitroprussides and alkali metal glycinates combined with sugars such as lactose, dextrose and sucrose.

While many assay devices of the prior art utilize dry tablets or powders in performing an assay, other assay devices utilize adsorbant carriers upon which some or all of the reagents have been dried. The adsorbant carriers may be in the form of strips which can be immersed in a sample of the liquid to be analyzed with the color reaction taking place in solution on the carrier. These assay devices, like those utilizing tablets or powders, suffer from decomposition of the nitroprusside indicator. In addition, indicator materials which are merely adsorbed onto the adsorbant carriers tend to suffer from diffusion of reagents away from the strip which affects the strength of the color signals. Further, the strips exhibit a certain amount of "bleeding" of color product in the aqueous environment which limits the stability of the color indicator signal of the reacted device.

Magers, et al., U.S. Pat. No. 4,147,514 discloses test strips for the detection of ketone bodies such as acetoacetic acid in bodily fluids utilizing a solution comprising nitroprusside in combination with at least one inorganic metal salt where the metal is selected from the group of magnesium and calcium. The solution optionally comprises at least one primary amine combined therewith. Test strips are dipped in the solution and are dried. They may be immersed in fluid samples and the occurrence of a color reaction observed.

U.K. Patent No. 1,012,542 discloses methods for the detection of ketone bodies in bodily fluids wherein alkaline components, in an aqueous solution are impregnated onto a carrier to which, sodium nitroprusside salt in an organic carrier also containing large amounts of an organic film-forming polymer is later applied. The carrier material is said to be very stable and is used for the detection of ketone bodies (acetoacetic acid) in liquid samples.

U.K. Patent No. 1,369,138 discloses improved methods for the detection of ketones in bodily fluids wherein an absorbant carrier is first impregnated with a solution consisting of an amino acid, tetrasodium ethylenediamine-tetraacetate buffer and water which is then dried. The carrier is then impregnated with a solution of sodium nitroprusside in dimethyl formaldehyde and optionally an alcohol containing one to four carbons and is dried.

Smeby, U.S. Pat. No. 2,990,253 discloses a device for the detection of ketone bodies in fluid samples comprising a bibulous carrier onto which nitroprusside is first applied in an aqueous acidic media and to which is subsequently applied a non-aqueous solution of organic bases such as amines or amino alcohols to achieve the alkalinity necessary for the assay reaction.

Mast, et al., U.S. Pat. No. 3,212,855 discloses an improved method for the production of a "dipstick" device for the detection of ketone bodies in fluids in which a bibulous carrier is first impregnated with an aqueous solution comprising an alkaline buffer and a water soluble amino acid. The carrier is then dried and impregnated with a solution in an organic solvent comprising an alkali metal nitroprusside and an organic film producing polymer.

Takasaka, Japanese Patent Application No. 1980-45270 discloses methods for the detection of ketones in body fluids utilizing test strips impregnated with alkali metal salts of nitroprusside and yttrium metal salts. The strips indicate a color reaction in acidic pHs in the presence of acetoacetic acid.

Federal Republic of Germany Patent No. 3,029,865 discloses improved test strips for the detection of ketones in bodily fluids comprising absorbant carriers impregnated with sodium nitroprusside, a water-soluble amino acid, an alkaline buffer compound and phosphoric acid trimorpholide as a stabilizer.

Kikuchi, Japanese Patent Application No. 1982-10208 discloses test strips for the detection of ketones in bodily fluids which are produced by immersion of absorbant carrier material in a solution comprising an amino acid, sodium triphosphate and sodium hydroxide and distilled water. The carrier strips are then dried and are immersed in a solution comprising a nitroprusside salt dissolved in dimethylformamide. They are then dried again and are ready for use.

Hirsch, U.S. Pat. No. 4,097,240 discloses a process for the production of dipstick devices for the detection of ketones in fluids such as urine. The process comprises the impregnation of an absorbant carrier with sodium nitroprusside, an alkaline buffer substance and a water soluble amino acid. The carrier is first impregnated with an aqueous solution of amino acid and tetrasodium ethylenediamine tetraacetate buffer and dried. It is then impregnated with a solution of sodium nitroprusside in a solvent mixture consisting of methanol and an organic solvent miscible with methanol such as a linear or branched aliphatic alcohol with two to six carbon atoms.

Habenstein, U.S. Pat. No. 4,184,850 discloses a dipstick device for the detection of ketone bodies in fluids comprising an absorbant carrier medium impregnated with sodium nitroprusside, a water-soluble lower amino acid, an alkaline buffer substance, and at least one organic acid which serves to form a stabilizing environment around the nitroprusside salt.

Kohl, U.S. Pat. No. 4,405,721 discloses devices for the detection of ketone bodies in bodily fluids comprising a carrier impregnated with a buffer, an amino acid, sodium nitroprusside and a heterocyclic stabilizing compound.

Tabb, et al., U.S. Pat. No. 4,440,724 discloses devices for the detection of ketone bodies in bodily fluids and methods for their preparation. The devices may be constructed according to steps comprising; impregnating a carrier with an aqueous solution of a soluble nitroprusside chromogen, drying the carrier, impregnating the carrier with an aqueous solution including a metal salt, a primary amine, TAPS (N-Tris (hydroxymethyl) 3-aminopropane sulfonic acid) and TRIS (tris-hydroxymethyl aminomethane) and drying the carrier, the pH of the finished test device being no greater than 7.0.

Of interest to the present application is the disclosure of Ogawa, et al., U.S. Pat. No. 3,880,590 which discloses a dipstick device for the semiquantitative detection of acetoacetic acid in liquids such as urine. The Ogawa, et al. strip is said to be incapable of detecting other ketone bodies, such as acetone and δ-hydroxybutyric acid. The device comprises an absorbant material, a nitroprusside salt and a heavy metal salt such as nickel or ferric chloride. The absorbant materials include silica gel paper, diethylaminoethyl (DEAE) cellulose paper and amino ethyl cellulose paper with which the nitroprusside salt is associated. The absorbant strips are impregnated with a solution of a nitroprusside salt and a heavy metal salt in water or organic solvents including dimethyl formamide, dimethyl sulfonate methanol and ethanol or mixtures thereof. Solvents disclosed to be useful in forming the devices include dimethylformamide, dimethylsulfoxide, methanol and ethanol and mixtures thereof. According to one example, dimethyl formamide solution is used to impregnate DEAE cellulose paper along with nickel chloride and sodium nitroprusside. The strips were dried and later used to detect the presence of acetoacetic acid in urine. It is disclosed that the impregnating solution itself may be useful for the detection of ketone bodies but that the dried test strips are preferred in view of preservation, stability and handling considerations.

While references variously refer to the use of nitroprusside and amine compositions for the detection of "acetone", "acetone bodies" and "ketone bodies", the assays primarily detect acetoacetic acid and are generally incapable of distinguishing between reaction products formed from reaction of acetone and reaction products formed from reaction of other ketone bodies including acetoacetic acid. Other assays, such as those of Ogawa, et al. are disclosed to be incapable of detecting acetone at all. While numerous advances have been made with respect to "Legal" assays for the detection of ketones and aldehydes, such assays are still limited by the instability of nitroprusside at pHs greater than 7. Finally, such assays still measure only the concentrations of ketone bodies in urine and fail to necessarily provide accurate measurements of ketone bodies present in the blood serum.

It is well known in the art that breath samples may be assayed for the presence of acetone in order to determine serum acetone levels. Acetone is a relatively volatile compound having a partition coefficient of approximately 330. It readily diffuses from the blood into the alveolar air of the lungs according to an equilibrium relationship. As a consequence of this equilibrium state, concentrations of acetone in alveolar air are directly proportional to those in the blood and measurements of acetone in alveolar air can be used to determine the concentration of acetone in the serum. Crofford, et al., Trans. Amer. Clin. Climatol. Assoc. 88, 128 (1977). Crofford, et al. also discloses the use of head space analysis to determine the ketone concentration of liquid samples.

Current methods for the measurement of breath acetone levels include the use of gas chromatography. Rooth, et al., The Lancet, 1102 (1966) discloses the use of a gas chromatograph capable of detecting acetone at concentrations of 2 to 4 nM of air with 18 nM being the concentration for breath of normal individuals. Subjects breathe directly into the device and the acetone peak is read after 40 seconds. Reichard, et al., J. Clin. Invest. 63, 619 (1979) discloses gas chromatographic techniques for the determination of breath acetone concentrations wherein breath samples are collected through the use of a calibrated suction flask into which the test subject breathes through a glass inlet tube. These methods and the instruments required for their use are complicated and expensive and tend to be impractical for use by consumers.

Other methods for the measurement of breath acetone levels involve the use of mass spectrographic equipment. Krotosynski, J. Chrom. Sci., 15, 239 (1977) discloses the use of mass spectrographic equipment in evaluating the ketone content of alveolar air. Twelve ketone components of breath were identified with acetone comprising the major component. Mass spectrographic methods suffer from the same limitations, however, as relate to gas chromatographic techniques.

Methods utilizing color reactions for the detection of acetone in liquid or air have also been reported in the art. Greenberg, et al., J. Biol. Chem. Vol. 154–155, 177 (1944) discloses methods for the determination of acetone levels apart from those of other ketone bodies in solution. The methods involve reaction of acetone and other ketones with 2,4-dinitrophenylhydrazine, to form hydrazone products which may then be separated and isolated owing to differing solubilities.

Peden, J. Lab. Clin. Med. 63,332 (1964) discloses improvements over the methods of Greenberg, et al. utilizing salicylaldehyde as a coloring reagent. According to this method, $\beta$-hydroxybutyric acid is converted to acetone by oxidation with the amount of acetone formed measured by reaction with salicylaldehyde. Preformed acetone and acetoacetic acid are removed prior to the conversion of the $\beta$-hydroxybutyric acid by heating in the presence of acid. While these methods are useful for the determination of acetone concentrations apart from those of other ketone bodies they are complex and time consuming.

These various colorimetric methods known for detection of acetone in biological fluids are complex, time consuming and necessitate the use of a spectrophotometer or color charts. Moreover, the methods often require the use of high concentrations of alkali or acids. Alternative methods for the detection of acetone often require the use of complex and expensive apparatus. There thus continues to exist a need for methods for the quantitative determination of fluid acetone concentrations which are simple, accurate, inexpensive and do not require the use of high concentrations of hazardous reagents.

There exists a desire for methods for the measurement of the rate of fat catabolism. It is a particular problem that many individuals undergoing diets are unable to determine their rate of fat-loss because of daily variation in their body fluid content. Significantly, it is known that early in a diet individuals lose high proportions of fluid as compared to fat. Later in their diets, when individuals may still be catabolizing fat at a constant rate they may cease to lose fluids at the previous high rate or may, if only temporarily, regain fluid weight. The experience of hitting a plateau in weight loss or even regaining weight is psychologically damaging and weakens the subject's resolve to continue with the diet often with the effect that the subject discontinues the diet.

Recently, a method has been disclosed for the determination of daily rate of fat loss. Wynn, et al., Lancet, 482 (1985) discloses that daily fat-loss may be calculated by subtracting daily fluid and protein mass changes from daily weight changes. Changes in body water are estimated from the sum of external sodium and potassium balances and protein mass changes are calculated from nitrogen balances. Such a method is complex and time consuming thus making it inconvenient for the consumer.

One set of methods for measuring body fat is by quantitating total body water (TBW). A number of methods are available for determining TBW. These include isotopic dilution procedures using deuturiated water, tritiated water and $^{18}$O-labelled water. Urine, blood serum or saliva samples are collected after a 2 to 4 hour equilibration. The fluid samples are then vacuum sublimed and the concentration of tracer in the sublimate is determined by mass spectrometer, gas chromatography, or infrared or nuclear magnetic resonance spectroscopy. Body composition can also be measured by a bioelectrical impedence method using a body composition analyzer. These methods are well known in the literature and are readily performed by those of skill in the art. Equipment for performing such measurements is available commercially from medical instrument manufacturers such as RJL Systems, Inc. (Detroit, Mich.).

Hydrostatic weighing method is a well known method wherein the subject is completely submerged in a tank of water and the body fat is calculated by taking into account the average density of fat and the amount of water displaced. This method is inconvenient and is still not completely accurate because assumptions must be made relating to nonfat density, lung capacity and other factors. Another method for calculating the percentage of body fat utilizes skin calipers to measure the thickness of fat deposited directly beneath the skin. Pincers are used to measure the thickness of folds of skin and fat at various locations on the body. The results of these measurements are compared with standardized tables to arrive at a figure for percentage of body fat. This method, while more convenient than the use of hydrostatic weighing is less accurate. All methods for determination of body fat content suffer from the fact that they do not reveal the rate of fat loss but only the fat content of the body at a particular time. Because means for determining body fat content are of limited accuracy, means for the determination of the rate of fat loss are similarly limited. Nevertheless it is desired that a simple and convenient method be developed for the determination of the rate of fat-loss wherein such a method is capable of distinguishing weight loss due to loss of fat as opposed to weight loss from the elimination of bodily fluids.

Of interest to the present invention are observations that ketosis occurs in non-diabetic individuals undergoing weight loss through diet, fasting or exercise. Freund, Metabolism 14, 985–990 (1965) observes that breath acetone concentration increases on "fasting." It is disclosed that breath acetone concentrations increased gradually from the end of the first day of the fast to approximately 50 hours into the fast at which time the concentration rose sharply in a linear fashion and reached a plateau on the fourth day. The acetone concentration of the plateau was approximately 300 $\mu$g/liter (5,000 nM) a hundred-fold increase over the normal value of 3 $\mu$g/liter (50 nM). When, instead of fasting, the subject was placed on a "ketogenic" diet with a minimum of 92% of calories derived from fat, the subject suffered a lesser degree of ketosis wherein the plateau had an acetone concentration of approximately 150 $\mu$g/liter (2,500 nM).

Rooth, et al., The Lancet, 1102–1105 (1966) discloses studies relating to the breath acetone concentrations of a number of obese and diabetic subjects. When the caloric intake of three non-diabetic obese subjects was reduced, their breath acetone concentrations as measured by a gas chromatograph increased approximately threefold. On fasting, the subjects' breath acetone concentrations increased to one hundred times normal. Within 16 hours after a heavy meal the subjects' breath acetone concentrations dropped almost to normal. In a study of obese diabetic patients, the authors disclosed evidence that those obese patients who had lost weight in the last three months had higher breath acetone concentrations than those patients who had gained weight.

Walther, et al., Acta Biol. Med. Germ. 22, 117–121 (1969) discloses the results of a study on the effects of continued exercise of a well-trained cyclist. The authors disclose that breath acetone concentration, increases prior to, during and after the cessation of the physical load and reached a maximum 15 to 20 minutes after cessation of the physical load. Breath acetone concentrations approach a normal level one to two hours after the cessation of the physical load. It is suggested that the increased production of acetone is due to the increased utilization of plasma free fatty acids in liver and reduced utilization in peripheral tissue.

More recent studies have shown a correlation between fasting in normal and obese patients and increased blood acetone levels. Rooth, et al., Acta Med. Scand. 187, 455–463 (1970); Goschke, et al., Res. Exp. Med. 165, 233–244 (1975); and Reichard et al., J. Clin. Invest. 63, 619–626 (1979) all show the development of ketosis in both overweight and normal individuals during fasting. Rooth, et al., (1970) suggests the use of breath ketone measurements as a motivational tool to enforce against dietary cheating The studies disclose that development of ketosis is slower in overweight than in normal weight individuals. Reichard, et al., discloses that there is a better correlation between breath acetone and plasma ketone concentrations than between urine ketone and plasma ketone concentrations. In addition, Rooth, et al., (1970) discloses that certain urine ketone tests which detect the presence of acetoacetic acid are not entirely reliable because some individuals do not excrete acetoacetic acid in the urine despite increased blood serum concentrations.

Crofford, et al., (1977) discloses the use of breath acetone monitoring for monitoring of diabetic conditions and as a motivational tool in following patients on long-term weight reduction programs Such monitoring is said to be particularly effective as normalization of the breath acetone is disclosed to occur upon significant dietary indiscretion. Patients' breath samples were monitored using a gas chromatograph and it is suggested that patients be instructed to restrict their caloric input to that which will maintain breath acetone concentrations of approximately 500 nM. It is further suggested that if breath acetone is controlled at this level and the proper balance of carbohydrate, protein and fat are maintained in the diet that weight loss will occur at a rate of approximately one-half pound per week.

SUMMARY OF THE INVENTION

The present invention relates to methods and materials for the detection of ketones and aldehydes in fluid (liquid or vapor) samples. The invention is particularly directed to the quantitative determination of ketone and aldehyde concentrations in physiological fluids including serum, urine and breath samples The invention is particularly suited for the determination of acetone concentrations. According to one aspect of the invention, methods are disclosed for the quantitative determination of serum acetone concentrations through the measurement of breath acetone concentrations. The method of breath acetone measurement utilizing the methods and materials of this invention is also adoptable for monitoring the insulin dose requirement for Type 1 insulin-dependent diabetic patients and to distinguish between Type 1 (ketotic) and Type 2 (non-ketotic) diabetic patients. Alternatively, concentrations of acetone or other ketones or aldehydes in serum, urine or other liquids may be determined by head space analysis of vapors in equilibrium with a liquid sample. According to further aspects of the present invention, liquid samples may be analyzed quantitatively in a liquid phase reaction for the presence of aldehydes or ketone bodies such as acetoacetic acid. According to still further aspects of the invention, methods are disclosed for ascertaining the fat catabolism effects of a weight loss dietary regimen comprising diet, fasting or exercise through the quantitative determination of serum or alveolar air (breath) acetone concentrations. Preferred methods for determination of the rate of fat catabolism comprise measurement of breath acetone concentrations and may be readily determined by utilizing the devices of the invention. The present invention also provides kits for the determination of fluid ketone and aldehyde concentrations and for the determination of the rate of fat catabolism.

The present invention comprises methods and materials for the determination of fluid ketone and aldehyde analyte concentrations through the reaction of analytes present in the sample fluid with a nitroprusside compound in the presence of an amine and a solvent to produce a colored reaction product. Devices according to the invention comprise a first solid matrix material to which a nitroprusside salt such as sodium nitroprusside is coupled. The devices further comprise a second solid matrix material to which is covalently bound an amine. According to one aspect of the invention, the nitroprusside salt and the amine may be coupled with and covalently bound, respectively, to the same solid matrix material. Preferably, however, the first and second solid matrix materials are in the form of discrete particles which are treated accordingly with a nitroprusside salt or an amine and are intermixed so as to place nitroprusside and amine moieties in intimate contact with one another. The solid matrix materials may be selected from a variety of materials including cellulose and silica gel which present suitable coupling moieties or are susceptible to reaction with suitable coupling moieties.

While the various methods of the present invention vary according to their specifics, they share the common aspect wherein ketone or aldehyde analytes present in a sample are contacted in the presence of a solvent with a nitroprusside salt coupled to a first solid matrix material and an amine covalently bound to a second solid matrix material. These materials together react to form detectable reaction products of characteristic colors which may then be observed for a qualitative or quantitative determination of the presence of ketone or aldehyde analytes.

Specific methods and configurations of devices for carrying out those methods are known according to the identity of the analyte of interest and the nature of the sample material to be assayed. When the sample material is a vapor, a fixed quantity of the vapor may be collected by suitable means and the ketone or aldehyde analyte component preconcentrated on a preadsorbant material. The adsorbant for preconcentration of such analytes may be a material such as Tenax TA (a 2, 6-diphenyl-p-phenylene oxide polymer) or activated silica which may be maintained in the device in a preadsorbant zone separate from the first and second solid matrix materials associated with the nitroprusside salt and amine which are located in a reaction zone. After preconcentration, the ketone or aldehyde analytes are desorbed from the adsorbant by means of a solvent and contacted with the first and second solid matrix materials for reaction with the nitroprusside and amine reagents. According to a preferred embodiment, ketone and aldehyde components present in a vapor sample may be preconcentrated on the first and second solid matrix materials themselves. The analytes may then be solubilized by addition of a solvent to react with the nitroprusside and amine moieties present on the solid matrix materials. Where the analyte of interest is acetone methods for the assay of vapor samples, particularly breath samples, preferably utilize a desiccating bed for the preadsorption of water which can interfere with the quantitative detection of acetone.

In vapor sample devices wherein ketones and aldehydes are preconcentrated by adsorption onto the first and second solid matrix materials, a "linear reading system" for determination of analyte concentration may be utilized. The system provides a visual indication, in the form of a color bar of colored reaction products, indicating the quantity of ketone or aldehyde analytes adsorbed onto the first and second solid matrix materials. Because the adsorption sites on the matrix materials are limited, the extent to which ketone and aldehyde analytes will be adsorbed is dependent upon the quantity of analytes in the vapor sample. Analyte vapors will initially be adsorbed onto the solid matrix materials at the first portion of the reaction zone. As adsorption sites on those materials are saturated analyte vapors are adsorbed at more distant points within the reaction zone. Where the volume of the vapor sample is fixed, the distance from the first end of the reaction zone at which the analyte vapors are finally adsorbed is dependent upon the concentration of the analytes in the vapor sample. The extent to which the analytes are adsorbed, and hence the ketone or aldehyde concentration of the sample, is indicated by the extent of formation of colored reaction products.

When the sample material is a liquid such as urine or serum, head-space vapor assays may be carried out by analysis of vapor in equilibrium with the liquid for the presence of acetone and other volatile ketone and aldehyde components. After collection of a known volume of vapor in equilibrium with the liquid sample, the vapor is analyzed in the same way as breath and other vapor samples Such head-space analysis is particularly suitable for analysis of the more volatile ketone and aldehyde fractions of samples as "lighter" analytes such as acetone will be present in the head space vapor in higher proportions than other less volatile "heavy" analyte components.

Quantitative liquid phase colorimetric assays may also be conducted on samples such as serum or urine according to the methods of the present invention. Liquid assays are useful for detection of most ketones and aldehydes but are particularly useful for quantitative detection of less volatile analytes such as acetoacetic acid. According to such methods, liquid samples are applied to microcolumns packed with or dipsticks coated with the solid matrix materials of the invention. The presence of ketones or aldehydes in such samples produces a color reaction. Quantitative results can be obtained through use of ascending chromatography methods in microcolumns comprising the solid matrices of the invention The concentration of ketone and aldehyde analytes present in the sample may be determined by the height of color bar produced in the tube. Where a dipstick coated with the solid matrix materials of the invention is used, analyte concentrations may be determined by visual or spectrophotometric evaluation of the color signal.

These liquid phase methods for analysis of liquid samples are not particularly suitable for detection of acetone in aqueous solutions such as bodily fluids, however, because the presence of water in these solutions retards the reaction rate of acetone to less than one one-hundredth the reaction rate of acetoacetic acid. Nevertheless, if the concentration of acetone in an aqueous solution is sufficiently high, the liquid phase methods may be adopted.

One preferred device of the present invention utilizes a breath collection device into which a subject breaths and which can collect a selected amount of alveolar air. The breath sample is then passed through the analyzer device wherein an anhydrous calcium chloride desiccant bed removes water vapor from the breath sample. The sample is then passed through a bed filled with a mixture of first and second solid matrix materials comprising nitroprusside-DEAE silica gel and aminopropyl silica gel where acetone contained within the breath is adsorbed into the matrix. The distance to which the acetone is adsorbed is dependent upon the total amount of acetone present in the sample. A solvent mixture containing either methanol or methanol and dimethyl sulfoxide (DMSO) is then added to the matrix to activate the color reaction and form a blue color bar. The length of the color bar is proportional to the concentration of acetone in the fixed breath sample volume and may be compared with a table or calibration marks on the side of the matrix bed to determine the breath and serum acetone concentrations.

The methods and materials of the present invention may be utilized to monitor diabetic patients, to analyze for various metabolic abnormalities or may be utilized according to one aspect of the present invention for the monitoring of the rate of fat catabolism. It has been found that serum acetone concentrations and hence breath acetone concentrations which can be measured by the methods and devices of the present invention may be correlated directly with the rate of fat catabolism and fat-loss experienced by a subject undergoing a weight loss dietary regimen comprising fasting, dieting, exercise or a combination of the three. Serum and breath acetone concentrations may be determined by a variety of means and the rate of fat-loss calculated therefrom according to the invention. The methods and devices of the invention, however, are extremely convenient, are accurate within about 10% in determining serum acetone levels and are therefore particularly suitable for measuring fat catabolism and the rate of actual fat-loss as opposed to determining weight loss which is variable and often reflects variations in fluid losses. By measurement of breath acetone levels, a subject will be able to estimate with a high degree of accuracy his rate of fat-loss, the water-loss/fat-loss ratio and be able to adjust his diet and amount of exercise according to his desired weight loss goals.

BRIEF DESCRIPTION OF THE DRAWINGS

FIG. 21a depicts a diet progress chart for use in monitoring a diet program in conjunction with the present invention. FIG. 21b depicts the diet progress chart of FIG. 21a filled out to monitor a dietary weight loss program.

FIG. 24 is an exploded perspective view of the outer tubular member of blow tube of the kit shown in FIGS. 22 and 23.

FIG. 25 is an enlarged fragmentary longitudinal sectional view taken generally along line 25—25 of FIG. 24.

FIG. 26 is a perspective view of a disposable analyzer column which is usable with the breath-sampling kit of FIGS. 22 and 23.

FIG. 29 is a side elevational view of the assembly of FIG. 27 showing the position of the parts and the flow of air when the collected sample of air is being discharged from the bag through the analyzer column.

FIG. 30 is an end elevational view, partially in transverse section, of the assembly taken generally along the line 30—30 of FIG. 29.

FIG. 31 is a transverse sectional view taken generally along line 31—31 of FIG. 29

FIG. 32 is a fragmentary longitudinal sectional view taken generally along line 32—32 of FIG. 29 showing the unbroken ampule of reactant in the disposable analyzer column.

FIG. 33 is a fragmentary longitudinal sectional view similar to FIG. 32 but showing the ampule of reactant after same has been broken FIG. 34 is a transverse sectional view taken generally along line 34—34 of FIG. 27 with the analyzer column in its first rotary and axial position (breath-receiving mode) in the blow tube.

FIG. 35 is a transverse sectional view taken generally along line 35—35 of FIG. 29 with the analyzer column in its second rotary and axial position (breath-discharging mode) in the blow tube.

FIG. 36 is a transverse sectional view taken generally along line 36—36 of FIG. 27.

FIG. 37 is an enlarged fragmentary longitudinal sectional view showing the valve operation of the breath-sampling assembly when a user is blowing into the mouth piece as shown in FIG. 27.

FIG. 38 is an enlarged fragmentary longitudinal sectional view similar to FIG. 37 that is showing the valve operation after the user has completely filled the breath collection bag, a static condition during which the breath sample is retained in the collection bag.

FIG. 39 is an enlarged fragmentary longitudinal sectional view similar to FIGS. 37 and 38 but showing the valve operation after the analyzer column has been rotated 90 degrees from its initial position and then pushed further inwardly into the blow tube to the position shown in FIGS. 29 and 39 whereby the collected sample of breath is forced through the analyzer column and out through the mouth piece as a result of biased deflation of the collection bag.

DETAILED DESCRIPTION

Figure 1:
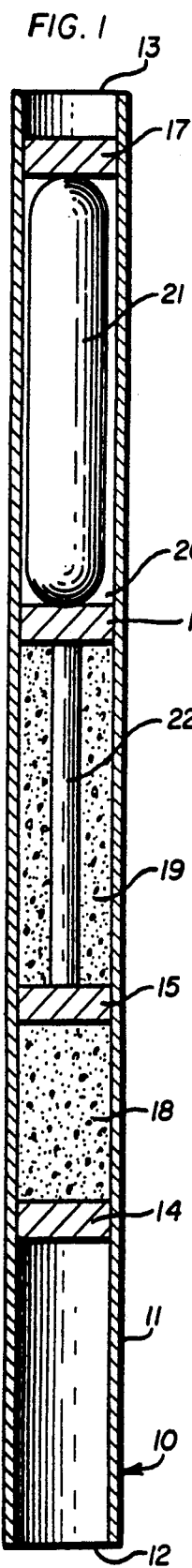
FIG. 1 is a view of a vapor test device of the present invention.

The present invention comprises methods and materials for the determination of fluid ketone and aldehyde concentrations through the reaction of such carbonyl group containing compounds with a nitroprusside compound in the presence of an amine and a suitable solvent to produce a color reaction Devices according to the invention comprise a first solid matrix material to which a nitroprusside salt is coupled and a second solid matrix material to which an amine is covalently bound. The addition of magnesium or calcium salts in the test composition promotes chelate formation thus stabilizing the color product and enhancing the kinetics of the reaction between the carbonyl compound, the amine and the nitroprusside.

Specifically, the first solid matrix material may be coupled to the nitroprusside salt by means of a suitable secondary or tertiary amine compound. The secondary or tertiary amine compound is itself coupled either directly to the first solid matrix material or to a coupling agent or coupling moiety which is attached to the first solid matrix material Such coupling moieties include silane epoxides such as 3'-glycidoxypropyltrimethoxysilane having a first functionality reactive with materials such as silica gel and a second epoxide functionality reactive with an aspect of a secondary or tertiary amine compound. Matrix materials presenting suitable coupling moieties include gels, ion exchange resins, glasses and cellulosic materials which may be obtained commercially. Such matrix materials include diethylaminoethyl (DEAE) silica gels, DEAE cellulose, diethylamino (DEA) silica gel, aminoethyl (AE) silica gel, quarternary aminoethyl (QAE) silica gel as well as other weakly or strongly basic ion exchange materials.

Matrix materials comprising suitable coupling moieties for coupling of nitroprusside salts need not be obtained commercially, but may be produced according to known procedures in the art. In Kundu, et al., J. Lipid Res. 19, pp 390-394 (1978) the disclosure of which is hereby incorporated by reference applicant discloses methods for the preparation of DEAE-silica gel. In Kundu, et al., J. Chrom. 170, pp. 65-72 (1979) the disclosure of which is hereby incorporated by reference applicant discloses methods for the preparation of DEAE-silica gel as well as DEAE-controlled porous glass.

The second solid matrix material is covalently bound to an amine by means of a coupling moiety which may be initially coupled to either the solid matrix material or to the amine. Illustrative of suitable chemistry is the reaction between 3'-aminopropyltrimethoxysilane and silica gel to produce aminopropyl silica gel. Lower alkyl amine silica gels such as aminopropyl silica gel are available commercially but may readily produced according to methods known to the art. In Kundu, et al., J Lipid Res., 20, pp. 825-833 (1979) hereby incorporated by reference, applicant discloses suitable methods for the preparation of aminopropyl silica gel.

Nitroprusside Salts

Nitroprusside salts suitable for coupling with the first solid matrix material of the present invention include those salts capable of reacting with ketone and aldehyde analytes in the presence of an amine and a solvent to produce a detectable color complex. Suitable nitroprusside salts include elemental metals and preferably alkali metal and alkali earth metal salts of nitroprusside. Preferred alkali metal salts of nitroprusside include sodium nitroprusside, while preferred alkali earth metal salts include salts of magnesium and calcium.

Secondary and Tertiary Amines

Secondary and tertiary amines suitable for coupling the nitroprusside salt to the first solid matrix material include those amines capable of forming an ionic complex with the nitroprusside salt and immobilizing it on the first solid matrix material. A preferred material is N,N-diethylethanolamine the hydroxy group of which can react with the epoxide moiety of a silane epoxide such as 3'-glycidoxypropyltrimethoxysilane to form diethylaminoethyl substituted materials such as DEAE silica gel and DEAE cellulose.

Coupling Agents

Coupling agents suitable for use with the present invention include those agents having a first group reactive to form a bond with the first matrix material and a second group reactive to form a bond to a secondary or tertiary amine compound. Particularly preferred is the use of silane coupling agents having an alkoxy silane group. Preferred coupling agents include those such as α-aminopropyltriethoxy silane, N-β-(aminoethyl)-γ-aminopropyl-trimethoxy silane and α-chloropropyl triethoxy silane. Particularly preferred are silane coupling agents such as 3'-glycidoxypropyl trimethoxy silane having a first alkoxy silane group and a second epoxide group

Amines

Amines suitable for covalent binding to the second solid matrix materials of the present invention include those amines capable of reacting with ketones or aldehydes and nitroprusside materials in the presence of a solvent to produce a detectable color complex Suitable amines include primary and secondary polyamines and primary and secondary lower alkyl amines with from 1 to 10 carbons. Primary amines are preferred although secondary amines are also suitable for methods and procedures of the present invention Amines are coupled to the second solid matrix materials of the invention by means of coupling moieties Typically the matrix materials are reacted with silane substituted amine-coupling agent conjugates such as 3'-aminopropyltrimethoxysilane. This material will react with a suitable matrix material such as silica gel or cellulose to produce aminopropyl silica gel or aminopropyl cellulose although the invention is not limited to aminopropyl moieties and other materials are equally suitable.

Solid Matrix Materials

Suitable solid matrix materials for coupling with nitroprusside salts and for covalent binding to amines include high surface area materials such as silica gels, glass materials such as controlled porous glass, granular cellulosic or agarose based materials, cross-linked dextran polymers, inorganic or organic ion exchanger materials, kieselsur and other silicate materials. Preferred first and second solid matrix materials for the vapor phase devices of the present invention are the high surface area gel materials such as silica gels which are characterized by their high surface area, high flow properties and exceptional dimensional stability. While silica gels of varying sizes and porosities may be used, materials with pore diameters between about 60 and about 1000 angstroms and particle sizes between about 40 and about 400 microns are preferred. Particularly preferred are silica gel particles with pore diameters between about 100 and about 200 angstroms and particle sizes ranging between about 200 and about 400 microns. Most preferred for use as the first solid matrix materials for coupling with nitroprusside salts are diethyl amino (DEA) silica gel particles obtained from Diagnostic Specialties/Separation Industries, (Metuchen, N.J.). The particles are characterized by having particle sizes ranging from about 250 to about 400 microns, mean pore diameters of 130 angstroms; mean surface area of 194 $m^2/g$; mean settle volumes of 1.9 cc/g; and an elemental composition comprising 10.90% C, 0.85% N, and 2.17% H. Other suitable first solid matrix materials include diethylaminoethyl (DEAE), aminoethyl (AE), quaternary aminoethyl (QAE) and other weakly or strongly basic ion exchangers on different organic or inorganic supports First and second solid matrix materials suitable for the liquid phase detection devices of the present invention include those gel materials generally suitable for the vapor phase detection devices, although preferably with smaller diameters. A preferred DEA-silica gel for use as the first and second matrix materials in the liquid phase assays according to the invention may be obtained from Diagnostic Specialties/Separation Industries (Metuchen, N.J.). The material is characterized by having particle sizes ranging from about 40 to about 60 microns in diameter, mean pore diameters of 200 angstroms, mean surface area of 180 $m^2/g$, mean settle volume of 1.8 cc/g; and an elemental composition of 10.57% C, 0.82% N and 2.10% H. Suitable materials additionally include a number of materials less suited for the vapor phase devices of the present invention such as cellulosic materials. Preferred celluosic materials to be coupled with a nitroprusside salt include diethylaminoethyl (DEAE) cellulose and diethylamino (DEA) cellulose. A preferred material for the second matrix material is aminopropyl cellulose.

Numerous other appropriately substituted materials are suitable as the matrix materials of the present invention. These include:

(A) Natural polymeric carbohydrates and their synthetically modified, cross-linked or substituted derivatives, such as agar, agarose and cross-linked dextran polymers (B) Synthetic polymers which can be prepared with suitably porous structures, such as (a) vinyl polymers, such as polyethylene, polypropylene, polystyrene, polyvinylchloride, polyvinylacetate and its partially hydrolysed derivatives, polyacrylates, polyacrylamides, polymethacrylates; (b) copolymers and terpolymers of the above vinyl monomers among themselves and with other monomers; (c) polycondensates, such as polyesters, polyamides and (d) addition polymers, such as polyurethanes or polyepoxides.

(C) Inorganic materials which can be prepared in a suitably porous form, such as sulfates or carbonates of alkaline earth metals and magnesium, e.g., barium sulfate, calcium sulfate, calcium carbonate, magnesium carbonate, or silicates of alkali and alkaline earth metals and/or aluminum and/or magnesium, and aluminum or silicon oxides or hydrates, such as clays, alumina, talc, kaolin, zeolite, silica gels and glass such as controlled porous glass These materials can be used as such or as fillers in one of the above polymeric materials.

(D) Mixtures or copolymers of the above classes, such as graft copolymers obtained by initiating polymerization of synthetic polymers on a pre-existing natural polymer.

The following examples disclose methods for the production of the solid matrix materials of the invention.

EXAMPLE 1

In this example, DEAE silica gel was prepared according to the procedure described by Kundu, et al., J. Lipid Res., 19, 390–395 (1978). According to this procedure 100 grams of silica gel which was obtained from Diagnostic Specialties/Separation Industries (Metuchen, N.J.) was deareated under vacuum for 30 min. and then heated at 45° C. for 20 hours with a mixture containing 1000 ml of 10% 3'-glycidoxypropyltrimethoxysilane (Polyscience, Inc., Warrington, Pa.) and 100 ml of N,N-diethanolamine (Aldrich Chemical Co., Milwaukee, Wis.). The reaction mixture was allowed to cool to room temperature. It was filtered through a coarse-porosity sintered glass funnel and washed with 2 liters of methanol to remove unbound reactants and by-products. The silica matrix was then converted to the chloride form by treatment with hydrochloric acid until the pH became 4.5.

According to an alternative procedure described by Roy and Kundu, Anal. Biochem., 98, 238–241 (1979), 100 grams of silica gel is heated with 1000 ml of 10% 3'-glycidoxypropyltriethoxysilane in toluene at 60° C. for 15 hours. After cooling to room temperature, the reaction mixture is filtered and washed with 2 liter of acetone and dried under vacuum to yield epoxy silica gel. The epoxy silica gel (100 g) is heated with 1000 ml of 10% diethylamine (Sigma Chemical Company, St. Louis, Mo.) in toluene at 50° C. for 20 hours. Diethylamino (DEA) silica gel thus obtained is processed to the chloride form as described above for DEAE-silica gel).

The DEA-silica or DEAE-silica gel prepared according to the above procedure is then treated with sodium nitroprusside alone or sodium nitroprusside mixed with magnesium or calcium sulfate to form nitroprusside DEA or DEAE-silica. According to one procedure, one hundred gram aliquots of DEAE silica gel were then taken in dark bottles and each mixed with one liter of aqueous solution of sodium nitroprusside at concentrations of 2 g/liter, 4 g/liter, 5 g liter, 6 g liter, 8 g/liter and 10 g/liter. The mixtures were rotated in the dark for 5 minutes, filtered on coarse-porosity sintered glass funnels and dried thoroughly under vacuum. Alternatively, the DEA or DEAE-silica materials were additionally treated with nitroprusside at concentrations of 2 g/liter, 4 g/liter, 5 g/liter, 6 g/liter, 8 g/liter and 10 g/liter mixed with equimolar amounts of magnesium sulfate. The mixtures were then rotated in the dark for 5 minutes, filtered on coarse-porosity sintered glass funnels and dried thoroughly under vacuum.

The total binding capacity of this preferred DEA silica gel matrix was 100 mg nitroprusside per gram of matrix. The binding efficiency of sodium nitroprusside alone or when mixed with equimolar amounts of magnesium sulfate was 100% for materials treated with nitroprusside at concentrations of 2 to 5 g/liter, 98% for materials treated with 6 g/liter, 96% for 8 g/liter and 90% for 10 g/liter. Because the nitroprusside-DEA or DEAE silica gel matrix is sensitive to light these operations were performed so as to avoid direct exposure to light. Nevertheless, the matrix is stable at room temperature for extended periods if protected from the light.

EXAMPLE 2

In this example, aminopropyl silica gel was prepared according to the procedure described by Kundu, et al., J. Lipid, Res., 20, 825–833 (1979). In this method, 100 grams of silica gel was deareated under vacuum for 30 min. and then shaken at 50° C. for 20 hours with 600 ml of a solution comprising 10% (by weight) 3'-aminopropyltriethoxysilane (Polyscience, Inc., Warrington, Pa.) in toluene. The reaction mixture was allowed to cool to room temperature and filtered through a coarse-porosity sintered glass funnel The gel was washed with 2 liters of methanol to remove unreacted materials and other by-products and then with water. The material was then vacuum dried and stored at room temperature. The aminopropyl silica in the basic form is stable for a extended periods at room temperature. Similar procedures may be carried with other silanes containing an amino function. It could be a short chain ($C_1$–$C_{10}$) or polymeric type amine containing a silane function.

The aminopropyl silica matrix most preferred for use as the second solid matrix material for vapor phase detection devices according to the invention may be obtained from Diagnostic Specialties/Separation Industries (Metuchen, N.J.) and is characterized by having a mean particle size ranging from about 250 to about 400 microns; mean pore diameter of 130 angstroms; mean surface area of 194 $m^2$/g; mean pore volume of 0.63 $m^3$/g; and an elemental composition comprising 6.67% C, 2.42% N and 1.64% H.

EXAMPLE 3

In this example, aminobutyl silica gel was prepared utilizing epoxy silica gel prepared according to Example 2. One hundred grams of epoxy silica gel was deareated under vacuum for 30 min. and then shaken at 50° C. for 20 hours with 600 ml of a solution comprising 10% (by weight) 1,4-diaminobutane (Aldrich Chemical Company, Milwaukee, Wis.) in toluene. The reaction mixture was allowed to cool to room temperature, was filtered through a coarse-porosity sintered glass funnel and washed successively with 1 liter of toluene, 2 liters of methanol and 2 liters of water. The mixture was then vacuum dried and was stored at room temperature.

Similar procedures comprising opening of an epoxy silica matrix with diamines may be carried out with any short chain ($C_1$–$C_{10}$) or polymeric amines The opening of epoxy silica can also be extended by ammoniacal toluene or aqueous ammonia to generate a primary amine. In addition, the epoxy silica gel may be used as an intermediate to form secondary amine function with any short chain or polymeric secondary amine. Similarly, short chain or polymeric compounds containing tertiary amine functionalities may be used to produce a silica matrix with a tertiary amine structure.

EXAMPLE 4

In this example, test matrices were formed by mixing varying amounts of nitroprusside-DEAE silica produced according to the methods of Example 1 with aminopropyl silica produced according to the methods of Example 2. The matrices comprised varying amounts of nitroprusside ranging from 20 to 90 mg nitroprusside per gram of matrix. The matrices were prepared using DEA-silica, characterized by particle sizes ranging from 200 to 400 microns and average pore diameters of 130 angstroms obtained from Diagnostic Specialties/Separation Industries as described in Example 1. Numerous materials were evaluated including those with varying ratios of nitroprusside-DEA silica as described in Example 1 as well as a preferred aminopropyl silica material with particle sizes from 200-400 microns and average pore diameters of 130 Å (angstroms) obtained from Diagnostic Specialties/Separation as described in Example 2.

Materials suitable for a vapor assay devices according to the invention include various commercially available DEA or DEAE silica matrices of particle sizes ranging from 40 to 60, 60 to 100 and 100 to 200 microns with average pore diameters of 200 angstroms (Diagnostic Specialties/Separation Industries, Metuchen, N.J.) as well as those prepared as described in Example 1. These materials were evaluated by mixing with different ratios with aminopropyl silica matrices of the same particle size, i.e., 40 to 60, 60 to 100 and 100 to 200 microns and same pore diameter, 200 angstroms obtained from the same commercial source as well as alkyl silica matrices prepared as according to Examples 2 and 3. Evaluation of materials with varying matrix ratios of DEA or DEAE-silica and aminoalkyl silica showed that the most preferred composition for detection of acetone vapor samples comprised a first solid matrix material of porous DEA-silica gel particles with diameters ranging from 250 to 400 microns and average pore diameters of 130 angstroms. The preferred matrix comprised DEA silica particles containing 50 mg nitroprusside per gram of matrix (optionally associated with magnesium) and aminopropyl silica at a ratio of 1:2 (by weight).

The preferred composition for detection of ketones and aldehydes in aqueous media utilizes porous DEA- or DEAE-silica gel particles with diameters ranging from about 40 to about 100 microns with average pore diameters of about 200 angstroms. The preferred first solid matrix material utilizes DEA-silica materials with particle diameters of from about 40 to about 60 microns and average pore diameters of about 200 angstroms and may be obtained from Diagnostic Specialties/Separation Industries (Metuchen, N.J.) Aminopropyl silica particles with diameters ranging from about 40 to about 60 microns and having average pore diameters of about 200 angstroms may be obtained from Diagnostic Specialties/Separation Industries and are the most preferred second solid matrix materials. The most preferred reaction matrix for detection of acetoacetic acid in aqueous solutions comprises the above described nitroprusside DEA silica and aminopropyl silica materials at weight ratios of 1:1 with the DEA silica containing 20 mg nitroprusside per gram of matrix.

EXAMPLE 5

In this example, nitroprusside-DEAE cellulose was formed according to the following procedure. Ten grams of DEAE cellulose powder (Sigma Chemical Company, St. Louis, Mo., Cat. #D-8632) was reacted with 100 ml of aqueous sodium nitroprusside solution at a concentration of 10 g/liter. After mixing for 10 minutes in the dark at room temperature, the mixture was filtered on a sintered glass funnel, washed with 500 ml of water and dried thoroughly under vacuum. The nitroprusside-DEAE-cellulose powder was then stored at room temperature, protected from light and was stable for an extended period of time.

EXAMPLE 6

In this example, aminopropyl cellulose was formed according to the general procedure described in Example 2. Ten grams of cellulose powder (Whatman Chemical Separation Ltd., U.K.; Microgranular CC 41, Cat. #4061-050) was deareated under vacuum for 30 minutes. The material was shaken at 50° C. for 20 hours with 100 ml of a solution comprising 10% 3'-aminopropyltriethoxysilane (Polyscience Inc , Warrington, Pa.) in toluene. The reaction mixture was then allowed to cool to room temperature, was filtered, washed successively with 400 ml of methanol and water and was vacuum dried. It was stored at room temperature and is stable for an extended period of time.

EXAMPLE 7

In this example, test matrices were formed by mixing varying amounts of nitroprusside-DEAE cellulose produced according to the method of Example 5 with aminopropyl cellulose produced according to the method of Example 6 or aminopropyl silica produced according to the method of Example 2. The matrices so formed were tested by treatment with urine samples to which specific concentrations of acetoacetic acid had been added. Acetoacetic acid present in the test samples reacted with the nitroprusside salt and the amine present on the solid matrix materials to form a color product. The results indicating the sensitivity of the various materials are shown in Table 1 below.

TABLE 1

OPTIMIZATION OF NITROPRUSSIDE-DEA/DEAE AND AMINOPROPYL SILICA AND CELLULOSE MIXTURES FOR URINE ACETOACETIC ACID TEST

| Test Device | NPR-Matrix and Aminopropyl Matrix Weight Ratio | Urine Acetoacetic Acid Conc. Mg/DL | Readability of Purple Color (Background Color) |
|---|---|---|---|
| NPR-DEA Silica*: Aminopropyl Silica** | 1:1 | 5 | Good (Light Tan) |
|  | 1:2 | 5 | Excellent (Light Tan) |
| NPR-DEAE Cellulose***: Aminopropyl Silica** | 1:4 | 5 | Good (Very Light Tan) |
|  | 2:1 | 5 | Good (Tan) |
| NPR-DEAE Cellulose***: Aminopropyl Cellulose**** | 1.2 | 5 | Poor (Light Tan) |
|  |  | 10 | Poor (Light Tan) |
|  | 1:4 | 5 | Poor (Light Tan) |
|  |  | 10 | Fair (Light Tan) |
|  | 1:8 | 5 | Poor (Light Tan) |

TABLE 1-continued
OPTIMIZATION OF NITROPRUSSIDE-DEA/DEAE AND AMINOPROPYL SILICA AND CELLULOSE MIXTURES FOR URINE ACETOACETIC ACID TEST

| Test Device | NPR-Matrix and Aminopropyl Matrix Weight Ratio | Urine Acetoacetic Acid Conc. Mg/DL | Readability of Purple Color (Background Color) |
|---|---|---|---|
| | | 10 | Fair (Light Tan) |

*DEA-Silica used was obtained from Diagnostic Specialties/Separation Industries, Metuchen, NJ having the following properties: particle size, 40-60 microns, pore diameter, 200 angstroms; surface area 180 m²/g; mean settle volume, 1.8 cc/g and elemental composition comprising 11.37% C, 2.69% N and 2.00% H. The amount of nitroprusside bound to DEA silica was 50 mg/g of matrix.
**Aminopropyl silica was obtained from the same commercial source as DEA-silica having the particle size, porosity characteristics.
***NPR-DEAE cellulose was as described in Example 5.
****Aminopropyl cellulose was as described in Example 6.

Analysis of the test results indicates that the combination of nitroprusside DEA silica with aminopropyl silica at a weight ratio of 1:2 provides the best sensitivity. The combination of nitroprusside-DEAE-cellulose and aminopropyl silica provided good results. It was observed, however, that the mixture of nitroprusside-DEAE cellulose and aminopropyl cellulose had relatively poor sensitivity, possibly due to lower reactivity of aminopropyl cellulose. With less than a 5 mg/dl urine acetoacetic acid concentration, it was found difficult to read the color.

Sensitivity of the matrix can be enhanced by increasing the number of amino groups present. This may be accomplished by reaction of cellulose based matrix with epichlorohydrin to form the intermediate "epoxy cellulose." The epoxy ring present in the intermediate may then be opened with alkyl diamino compounds as disclosed in Example 3, with the result that the sensitivity can be enhanced. To illustrate this, nitroprusside-DEAE cellulose matrix was mixed with aminopropyl silica (the number of amino groups in aminopropyl silica was at least 5 times less compared to aminopropyl cellulose) and 5 mg/dl of urine acetoacetic acid could be easily detected, the sensitivity being as good as that of the silica matrices. The preferred composition for detection of urine acetoacetic acid comprised nitroprusside-DEAE cellulose and aminopropyl silica at a weight ratio of 1:4 with DEAE cellulose containing approximately 5 mg nitroprusside per gram of matrix as shown in Table 1.

EXAMPLE 8

In this example a nitroprusside-DEAE-aminopropyl-silica bifunctional gel matrix was prepared wherein both the nitroprusside and amine functionalities were coupled to a single solid matrix material. Epoxy silica gel was prepared by reaction of 3'-glycidoxypropyl triethoxy silane according to the method of Example 1. The epoxy silica gel was then reacted with a mixture comprising 1,4-diaminobutane and diethylamine at a molar ratio of 20:1, in toluene at 50° C. for 20 hours. The reaction mixture was then cooled to room temperature and filtered on a coarse-porosity glass funnel, exhaustively washed with toluene and methanol and dried under vacuum for 4 hours.

It was then necessary (because nitroprusside reacts with free amine) to protect the amino group by reaction with trifluroacetic anhydride and ethylamine at a 1:1 volume ratio at room temperature for 24 hours. The matrix was washed exhaustively with ethylacetate and methanol and dried in air. Nitroprusside was then incorporated onto the DEAE functionality by treatment of 10 grams of matrix with 100 ml of 10 g/liter sodium nitroprusside in water in the dark for 5 minutes as described according to Example 1.

The matrix was then filtered, washed thoroughly with water and dried under vacuum for 4 hours. The trifluroacetyl group was removed from the amino function by reaction with solid anhydrous potassium carbonate suspended in dry methanol while the pH of the reaction medium was maintained between 8.0 and 8.5 to prevent cleavage of the nitroprusside group from the DEAE functionality. The reaction mixture was mixed at room temperature in the dark for 8 hours with the pH monitored each hour and potassium carbonate added as needed to maintain the pH. The matrix was then filtered on a coarse porosity glass funnel in the dark, washed exhaustively with water and dried under vacuum for 12 hours.

The bifunctional gel demonstrated a sensitivity limit of 10 ng of liquid acetone or 0.17 nM. Because the partition coefficient of liquid and vapor state of acetone is approximately 330, 10 ng of liquid acetone would be equivalent to 3300 ng (58 nM) of acetone vapor. While the bifunctional matrix may not be suitable for detection of very low levels of acetone, it can be used to measure acetone vapor concentration of highly ketotic individuals (dieting or fasting) or monitoring breath acetone of insulin dependent type 1 diabetic patients whose breath acetone concentrations can be as high as 100-200 nM.

VAPOR TEST DEVICES

The devices of the present invention are suitable for the detection of ketone and aldehyde analytes in both liquid and gaseous (vapor) forms. Vapors which may be analyzed for the presence of such analyes include atmospheric air, laboratory and industrial vapors, breath and other vapors for which the quantitative analysis of ketone or aldehyde content is desired. A particular aspect of the present invention comprises methods and devices for the quantitative detection of acetone in human breath. Such detection is useful for the monitoring of serum acetone levels which is of value to diabetics in monitoring the onset of ketosis. Such detection is also useful according to a further aspect of the present invention relating to the quantitative monitoring of fat catabolism.

Referring to the drawing, FIG. 1 depicts a vapor test device (10) for the detection of ketone or aldehyde analytes present in a vapor sample comprising a length of inert cylinder (11) having a first end (12) at which a vapor sample may be introduced to the device by a sample means and a second end (13) at which vapor is exhausted from the device. Within the inert cylinder

(11) and progressing from the first end (12) to the second end (13) are a first porous barrier (14), a second porous barrier (15), a third porous barrier (16) and a fourth porous barrier (17) The first porous barrier (14) and the second porous barrier (15) define a pretreatment zone (18) filled with desiccant means. The second (15) and third (16) porous barriers define a reaction zone (19) filled with a first solid matrix material to which a nitroprusside salt is coupled and a second solid matrix material to which an amine is covalently bound. The reaction zone (19) may also comprise an axially aligned filler rod (22) which fills space within the reaction zone (19) and increases the length of the device over which a fixed volume of the first and second solid matrix materials are spread. Said third porous barrier (16) and said fourth porous barrier (17) define a solvent zone (20) in which is located a solvent ampule (21)

According to a procedure for use of the device, a fixed volume of sample vapor is introduced to the first end (12) of the device by suitable sample means and is allowed to flow through the length of the device before it is exhausted from the second end (13). As sample vapor flows through the device, water vapor present in the sample is adsorbed by desiccant means present in the pretreatment zone (18). Dehydrated vapor then flows through the reaction zone (19) where ketones and aldehydes present in the vapor are adsorbed by the first and second solid matrix materials. Analytes are first adsorbed at the end of the reaction zone (19) adjacent to the first porous barrier (14) closest the first end (12) but as the volume of vapor sample is passed through the device the solid matrix materials closest the first end become saturated and additional analytes are adsorbed onto the solid matrix materials progressively farther from the first end (12). Where the volume of the sample is fixed the distance to which the analytes are adsorbed into the reaction zone (19) may be directly correlated with the concentration of analytes present in the sample When the volume of sample vapor has been passed through the device, the solvent ampule (21) is broken allowing a volume of solvent to pass downward through the third porous barrier (16) into the reaction zone (19) where the first and second solid matrix materials are thoroughly wetted with the solvent. The nitroprusside salt which has been coupled to the first solid matrix material and the amine which has been covalently bound to the second solid matrix material then react in the presence of solvent with ketones and aldehydes adsorbed onto the solid matrix materials to form colored reaction products which form a colored bar in the device. These reaction products provide a visual signal indicating the areas of the reaction zone where vapor ketones were adsorbed and thus the concentration of analytes present in the sample.

Figure 2:
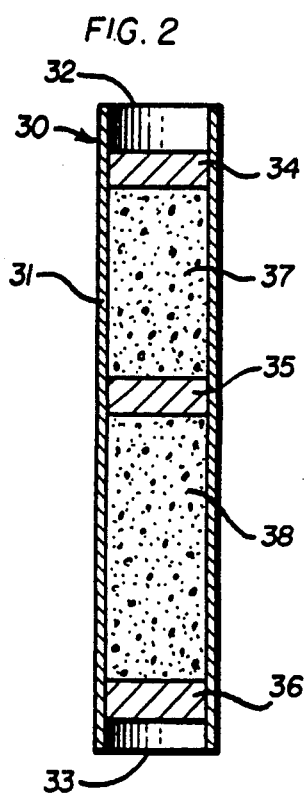
FIG. 2 is a view of an alternative vapor test device of the present invention.

Referring to the drawing, FIG. 2 depicts an alternative vapor test device (30) for the detection of ketones and aldehydes in a vapor sample comprising a length of inert cylinder (31) having a first end (32) at which a vapor sample may be introduced and a second end (33) at which vapor is exhausted from the device. Within the inert cylinder (31) and progressing from the first end (32) to the second end (33) are a first porous barrier (34), a second porous barrier (35) and a third porous barrier (36). The first porous barrier (34) and the second porous barrier (35) define a preadsorbant zone (37) which is filled with an adsorbant material capable of selectively adsorbing ketone and aldehyde analytes. The second porous barrier (35) and third porous barrier (36) define a reaction zone (38) filled with a first solid matrix material to which a nitroprusside salt is coupled and a second solid matrix material to which an amine is covalently bound.

According to a procedure for use of the device, a fixed volume of sample vapor is introduced to the first end (32) of the device by suitable sample means and is allowed to flow through the length of the device before it is exhausted from the second end (33) Ketones and aldehydes present in the sample vapor are selectively adsorbed on the adsorbant material present in the preadsorbant zone (37) When the volume of sample vapor has been passed through the device a quantity of solvent is introduced to the first end (32) of the device which then desorbs analytes adsorbed in the preadsorbant zone (37) and transports them to the reaction zone (38) There the analytes react in the presence of the solvent with the nitroprusside salts coupled to the first solid matrix material and the amine covalently bound to the second solid matrix material to form a colored reaction product.

Analyzer Column

The analyzer column comprises an inert cylinder fabricated from a material which will neither react with nor adsorb ketones or aldehydes and which is nonreactive with the reagents utilized in the assay The column materials are preferably transparent in order that the presence of a color reaction product may be detected and evaluated. Preferred materials include transparent plastics such as polystyrene and polyethylene terephthalate Glass tubes are acceptable but columns fabricated from polyethylene terephthalate are particularly preferred. Where the device is one according to FIG. 1, the cylinder is preferably somewhat flexible in order that pressure may be applied to rupture the solvent ampule Alternatively, where the solvent ampule comprises a readily puncturable end such as one of metal foil, means such as a plunger means may be incorporated with the device to free solvent from the ampule. The analyzer column may be of generally any size and geometry selected to contain sufficient reagents to analyze a sample of a selected size. According to one embodiment the column comprises a polyethylene terephthalate cylinder 13 cm long with an inner diameter of 0.8 cm. The cylinder is divided by means of three 0.5 cm porous barriers defining pretreatment zone 1.3 cm long, a reaction zone, 3.0 cm long and a 4.0 cm long solvent zone containing a solvent ampule. Optionally present in the reaction zone is filler means which may be an axially centered rod which can be used to fill a portion of the volume of the reaction zone and thereby elongate the length of the zone filled by a fixed volume of the first and second solid matrix materials. The rod itself may be transparent or opaque and should be inert to the analytes and reagents of the invention. It is preferably fabricated from polystyrene, being polyethylene terephthalate, or polypropylene with polypropylene being particularly preferred.

Porous Barriers

Porous barrier materials suitable for use with devices of the present invention include those materials which are inert to and nonreactive with the analytes and reagents of the invention and are porous with respect to the passage of vapor samples and solvents utilized in such devices. Suitable materials include various porous materials such as nylon fabric, glass wool, sponge, styrofoam and other ceramic and plastic materials. Preferred materials for use with the vapor phase devices of the present invention are porous polyethylene frits with a pore size of 100 microns (Porex Technologies, Fairburn, Ga.).

Preadsorbant Materials

Preadsorbant materials suitable for use with the present invention include those materials which are capable of selectively adsorbing ketone and aldehyde analytes from vapor samples. Such materials should also readily and completely desorb such analytes in the presence of preferred solvents of the invention such as methanol and methanol with dimethylsulfoxide (DMSO) Suitable materials include activated silica gel. A particularly preferred material is Tenax TA (a trademark of Enka N.V., Arnham, Netherlands) a 2,6-diphenyl-p-phenylene oxide polymer.

Desiccant Means

Vapor analyzer devices according to the present invention which are designed for the analysis of vapors containing water vapor, particularly breath, require means for the removal of water from the vapor sample prior to reaction with the assay matrix. This is particularly so where the material analyzed for is acetone, as the presence of water substantially reduces the rate of reaction of acetone with the nitroprusside and amine reagents of the invention. While a variety of desiccant materials are available which are capable of pre-drying vapor samples, it is desired to utilize a material which is inexpensive, safe and will not adsorb or react adversely with the ketone or aldehyde components of the vapor samples. Materials such as granular silica, anhydrous calcium sulfate, molecular sieve type 3A or 4A (W. R. Grace, Baltimore, Md.), magnesium perchlorate, activated charcoal, Bio-beads SM-2 and SM-4 (styrene-divinyl copolymers obtained from Bio-Rad Laboratories, Richmond, Va.) are generally undesirable materials because of their tendency to adsorb acetone. Ascarite II (16-20 mesh) (obtained from Thomas Scientific Swedesboro, N.J.) is an excellent desiccant and does not adsorb acetone but comprises sodium hydroxide silica particles and is corrosive and unsuitable from a handling standpoint.

A preferred material is anhydrous calcium chloride in pellet form. Various commercially available materials are suitable, although a particularly preferred material may be obtained in pellet form from Dow Chemicals, Ludington, Mich. as type 94 XFS 43284. The material may be fractured using a Fritzmill size reduction instrument (Fritzpatrick Company, Elmhurst, Ill.) and sized to between 16 and 24 mesh. The preferred calcium chloride granules are then heated at 200° C. for 20 hours and are stored in a closed bottle The amount of moisture permitted for the preferred calcium chloride is between 0-0.5%. The amount of calcium chloride needed for removal of moisture vapor samples may readily be determined by one of skill in the art. The amount of calcium chloride required for removal of moisture from a 450 cc breath sample is between 120 and 180 mg.

It has been established that 150 mg of calcium chloride (Dow 94 XFS, 16F-24 mesh, 0-0.4% moisture) adsorbs 100% of moisture from a 450 cc breath sample The amount of moisture in a 450 cc breath sample is 4.90 ±0.99 (SD, n=56). The recovery of acetone vapor from 450 cc breath samples (n=20) using same amount calcium chloride is also 100%. It is important to note that if the amount of anhydrous calcium chloride exceeds about 200 mg, there is a tendency to adsorb acetone from 450 cc breath samples Other types of calcium chloride such as Type P 90 (Dow Chemical) obtained in pellet form and fractured to the desired 16-24 mesh size can also be used to remove moisture from breath and other vapor samples. To reduce the moisture content of P 90 calcium chloride to less than 0.5%, it must be heated at 200° C. for at least 48 hours. The material may then be stored in a closed container until needed.

Sample Means

The devices of the present invention for the quantitative detection of ketones and aldehydes in vapor samples require means for the introduction of a fixed quantity of vapor sample to the detection column. Suitable means are those which comprise materials which are inert with respect to the ketone samples and are capable of reproducibly delivering a fixed volume of sample vapor to the device. It is desired that vapor samples be introduced to the devices of the invention at a relatively steady rate in order that analytes present in the sample be reproducibly adsorbed on the first and second solid matrix materials of the reaction zone. Unsteady vapor flow into the devices may cause analytes to be unevenly adsorbed onto the matrix materials of the device with the consequence that inconsistent and unreproducible analyte concentrations would be indicated by the assay devices.

Balloons and bags are particularly suitable for such applications although it is necessary that the material from which the bag or balloon is constructed be inert to the ketone and aldehyde materials of the sample. It was found that rubberized films and polyvinyl films adsorbed greater than 25% of acetone present in a breath sample in ten minutes Films found to be suitable included those fashioned from nylon, teflon, very low density density polyethylene, and a copolymer of polyester with polyvinyl chloride/vinylidene chloride (Saran) Bolton, et al., U.S. Pat. No. 4,579,826 herein incorporated by reference, describes methods and devices for sampling of predominantly alveolar breath. Bolton, et al. specifically discloses one device comprising a non-self-supporting polymeric tube and a spring means effective to roll the tube upon itself in spiral fashion toward the mouthpiece unit.

Particularly preferred due to high permeability of water vapor and its durability and low cost is the use of bags of 1 mil thick nylon. According to one embodiment, a nylon bag with a capacity of 450 cubic centimeters is attached to a valve device comprising a column, a mouthpiece, and a plunger. With the plunger set in one position the test subject takes a deep breath, holds it for five seconds and blows a breath sample into the device at a steady rate until the sample bag is completely inflated. The plunger is then pushed down to an alternate position and the sample bag is steadily deflated by a spring means blowing the sample vapor through the device and contacting analytes with either the preadsorbant bed or the nitroprusside and amine treated first and second matrix materials. Where the material to be sampled is atmospheric air or an industrial or laboratory vapor sample, a sample port may be substituted for the mouthpiece. Vapor samples may be collected by a bellows or other suitable means and appropriate volumes of material introduced to the device.

Figure 22:
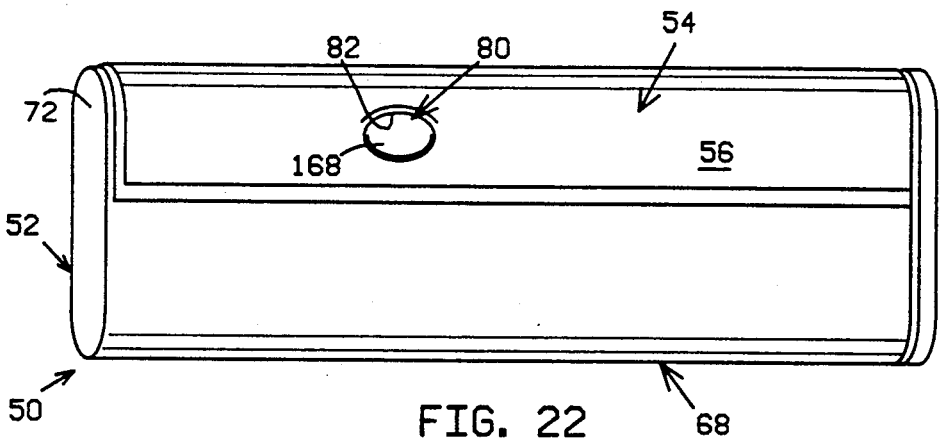
FIG. 22 is a perspective view of a breath-sampling kit of the present invention.
Figure 23:
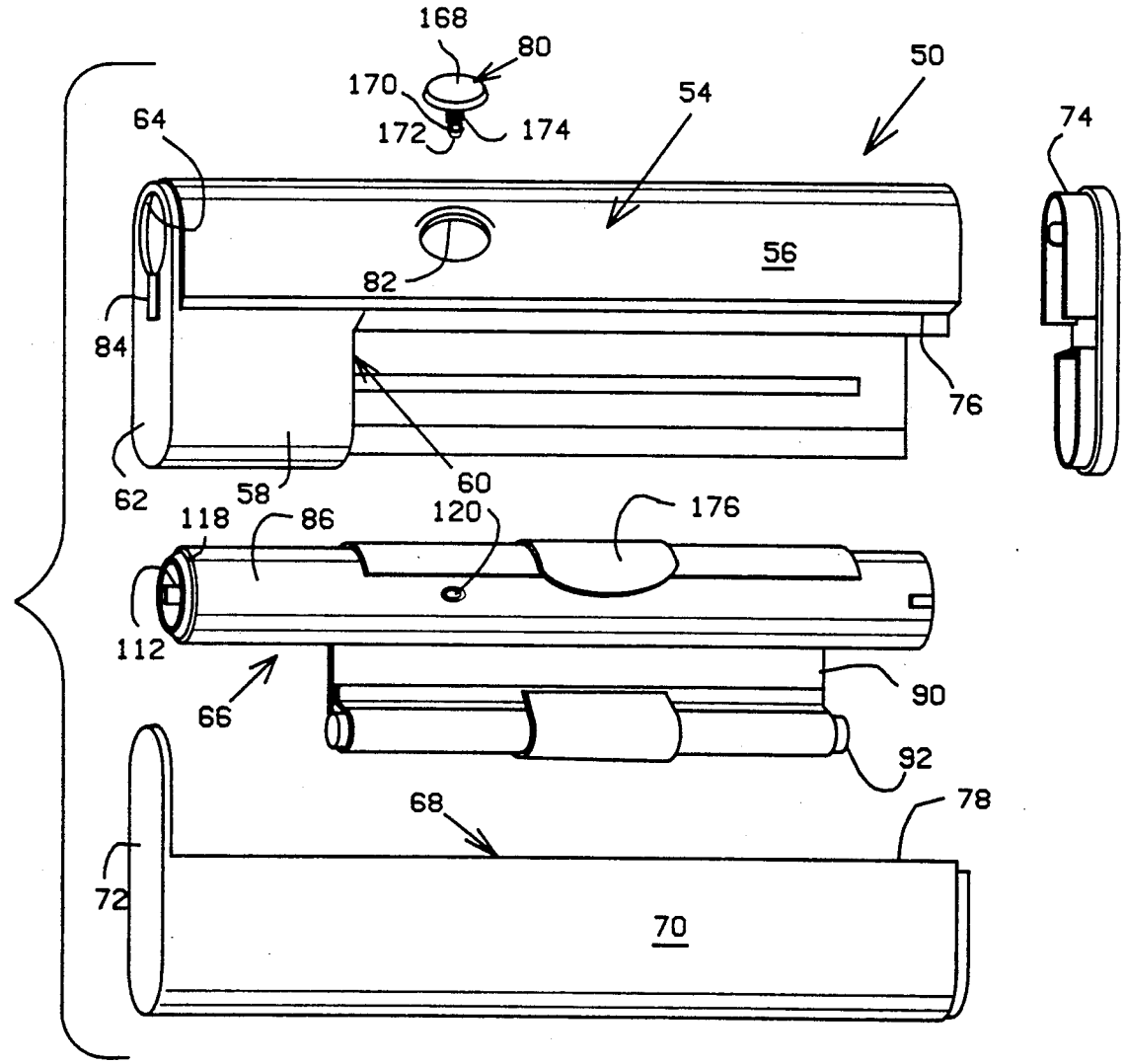
FIG. 23 is an exploded perspective view of the kit shown in FIG. 22.

With reference now to FIGS. 22-39, one embodiment of a breath-sampling kit for practicing a method of the present invention will now be described. As best illustrated in FIGS. 22, 23 and 26, a breath-sampling kit

(50) includes a portable housing (52) characterized by: an elongated base (54) having an inverted U-shaped portion (56) open at its right end (as viewed in FIG. 23) and having an integral depending but upwardly opening U-shaped portion (58) at its left end, defining a vertically disposed compartment (60) open at its right end but including an end wall (62) at its left end having a circular opening (64) provided therein; a breath-sampling assembly (66) which is fitted in the base (54) and retained therein by a cover (68) which is characterized by an elongated U-shaped portion (70) having a vertically disposed end wall (72) at its left end (as viewed in FIG. 23) which is adapted to overlay the end wall (62) of the base (54); and an end cap (74) which fits over the closes the right end of the housing (52) in a suitable manner. The meeting edges (76) and (78) of the U-shaped portions (56) and (70) of the base (54) and the cover (68), respectively, are designed for interfitting engagement in a known manner. The kit (50) also includes a breaker button (80) which is disposed in an opening (82) provided in a side wall of the housing base (54) for a purpose which will be described in detail hereinafter. A slightly raised marker (84) depends from the bottom of an opening (64) on the outer surface of the end wall (62) of the compartment (60) for a purpose which will also be described hereinafter.

As best illustrated in FIGS. 23, 24, 27 and 28, the breath-sampling assembly (66) is characterized by: an elongated outer tubular member or blow tube (86) which is formed of a transparent inert plastic material and which has an opening (88) formed in the side wall thereof toward the bottom of the tube (86); an inflatable/deflatable air or breath collecting plastic bag (90) having a specific volumetric capacity and having an open end secured to the outer surface of the tube (86) and in communication with the opening (88) provided therein, the opposite end of the bag (90) being closed and secured to a rigid support member (92) which is disposed generally parallel to the tube (86); a valve housing (94) which is secured in a valve housing recess (96) provided in the lower end of the tube (86); a ball valve (97) which may be formed of polypropylene and which is disposed in an axial recess (98) provided in the inner end of the valve housing (94) and; an O-ring (100) which is retained against downwardly facing O-ring seating means (102) provided in the tube (86) by the inner end of the valve housing (94) As best illustrated in FIGS. 37, 38 and 39, the inner end of the valve housing (94), which is reduced in diameter relative to the outer end, is provided with a diametrically extending bore (104) which is axially aligned with the opening (88) in the blow tube (86) to the bag (90) and with a pair of diametrically opposite vertically extending slots (106) adjacent to but spaced from the inner end of the valve housing (94) with a lower valve seat (108) for the ball valve (97) being defined in the recess (98) above the lower end of the slots (106) for a reason which will be made clear hereinafter. It is also noted that the diameter of the ball valve (97) is somewhat greater than the inner diameter of the O-ring (100)

With reference to FIGS. 24, 25, 35, 36, 37, 38 and 39, it is noted that the inner surface of the blow tube (86) is provided with four equidistantly spaced, longitudinally extending ribs (110) and (112). Three of the ribs (110) terminate short of the upper end of the blow tube (86) by a distance approximately equal to 1/5 of the overall length of the tube (86). The fourth rib (112) terminates almost at the upper end of converge inwardly at their lower ends to define the O-ring seating means (102). As shown in FIG. 25, the upper end of the rib (112) is provided with a stepped configuration to define a first holding surface (114) for the analyzer column and a second positive stop surface (116). An external annular rib (118) at the upper end of the tube (86) limits insertion of the blow tube (86) into the opening (64) provided in the end wall (52) of the housing compartment (60). The blow tube (86) is also provided with a button hole (120) which is adapted to be radially aligned with the breaker button opening (82) in the housing base (54) when the breath-sampling assembly (66) is fitted in the housing base (54).

A disposable analyzer column (122) is provided for use with the breath-sampling assembly (66) described herein. As best illustrated in FIGS. 26, 27, 29 and 32–39, the disposable analyzer column (122), which is formed of a transparent inert plastic having a degree of flexibility as previously noted herein, is characterized by a tubular member (124) having a series of axially spaced zones which will be defined hereinafter The tubular member (124) has an upper mouth piece portion (126) of a diameter which is receivable in the open end of the blow tube (86) seated in the opening (64) in the housing base (54), which opening is exposed upon the removal of the cover (68). The tubular member also has a first reduced-diameter portion (128), which comprises a major portion of the length of a column (122), and a second further reduced-diameter end portion (130) of a relatively short length. An annular shoulder (132) is defined between the two reduced-diameter portions (128) and (130) and an inclined or frusto-conical wall segment (134) is defined between the mouth piece portion (126) and the first reduced-diameter portion (128). For a purpose which will be discussed hereinafter, a series of air or breath openings (136) are provided in the inclined wall segment (134) The openings (136) preferably are equidistantly, circumferentially spaced around the wall segment (134) as illustrated in FIG. 34. Further, as illustrated in FIGS. 26, 27, 34 and 35, a pair of diametrically opposite longitudinally extending flats (138) are provided on the outer surface of the mouth piece portion (126), which flats (138) extend from the inclined wall segment (134) for a distance approximately equal to ½ of the length of the mouth piece portion (126), at which point inwardly facing shoulders (140) are defined.

Within the analyzer column (122), from the lower end to the upper end as viewed in FIG. 26, there is provided a first porous barrier or frit filter (142) which is secured in the end of the second reduced-diameter end portion (130); a second porous barrier or frit filter (144) which is seated against the annular shoulder (132) defined between the two reduced-diameter portions (128) and (130); an inert filler rod (146) having a longitudinal slot (148) formed therein which is seated against the filter (144) in the first reduced-diameter portion (128); a third porous barrier or frit filter (150) which is seated against the opposite upper end of the filler rod (146); a breakable ampule (152) containing liquid solvent or reactant disposed in the first reduced-diameter portion (128) above the third filter (150); and a fourth porous barrier or frit filter (154) which is provided in the first reduced-diameter portion (128) above the ampule (152). Each of the porous filters or frits is held in place by friction or raised projections on the inner surface of the analyzer column (122).

With reference again to the axially spaced zones of the analyzer column (122), a pretreatment zone (156) is defined in the second reduced diameter end portion (130) between the first and second porous barriers or filters (142) and (143). The pretreatment zone (156) is filled with a suitable desiccant means (158) such as $CaCl_2$. A reaction zone (160) is defined between the second and third filters (144) and (150) in that the longitudinal slot (148) in the filler rod (146) is filled with one or more solid reactive materials (162) as described elsewhere. A solvent zone (164) in which the ampule (152) is disposed is defined between the third and fourth filters (150) and (154). As previously noted, herein the filler rod (146) fills a substantial portion of the space within the reaction zone (160) and thus increases the length of the zone (160) over which a fixed volume of a solid reactive material or materials (162) is spread. As best shown in FIGS. 27, 29, 32 and 33, indicia markings (166) may be provided on the filler rod (146) adjacent to slot (148)

Before describing how the breath-sampling kit (50) is used to collect and test a sample of a person's breath, reference is first made to FIGS. 22, 23, 24 and 31, showing the breaker button (80), and to FIGS. 32 and 33. The breaker button (80) is characterized by: a manually depressable head portion (168) which is freely receivable in the opening (82) provided in the housing base (54); an inwardly projecting stem portion (170) which extends through the opening (120) provided in the blow tube (86) and which is retained therein by an enlarged head (172) on the end thereof; and a coil spring (174) which is disposed about the stem portion (170) between the underside of the breaker button head (168) and the outer surface of the blow tube (86), whereby the breaker button (80) is normally biased away from the blow tube (86). As shown in the drawings, the breaker button (80) is longitudinally positioned on the blow tube (86) such that the stem head (172) is aligned with the solvent zone (164) of the analyzer column (122) when the analyzer column (122) is inserted into the blow tube (86) during a collection and testing procedure. Thus, sufficient inward pressure on the breaker button (80) forces the stem head (172) against the flexible solvent zone portion (164) of the analyzer column (122) with sufficient pressure to break the ampule (152) and permit the reactant solvent to flow downwardly through the "exposed" reactive material or materials (162) in the longitudinal slot (148) of the filler rod (146) Obviously, the ampule (152) should preferably be broken at the end most closely adjacent to the reaction zone (160) as shown in the drawings, to ensure a maximum flow of the reactant/solvent If the ampule (152) were broken at an upper end, it is possible that part of the reactant/solvent would be retained in the unbroken lower portion of the ampule (152) with unreliable test results possibly resulting therefrom.

Figure 27:
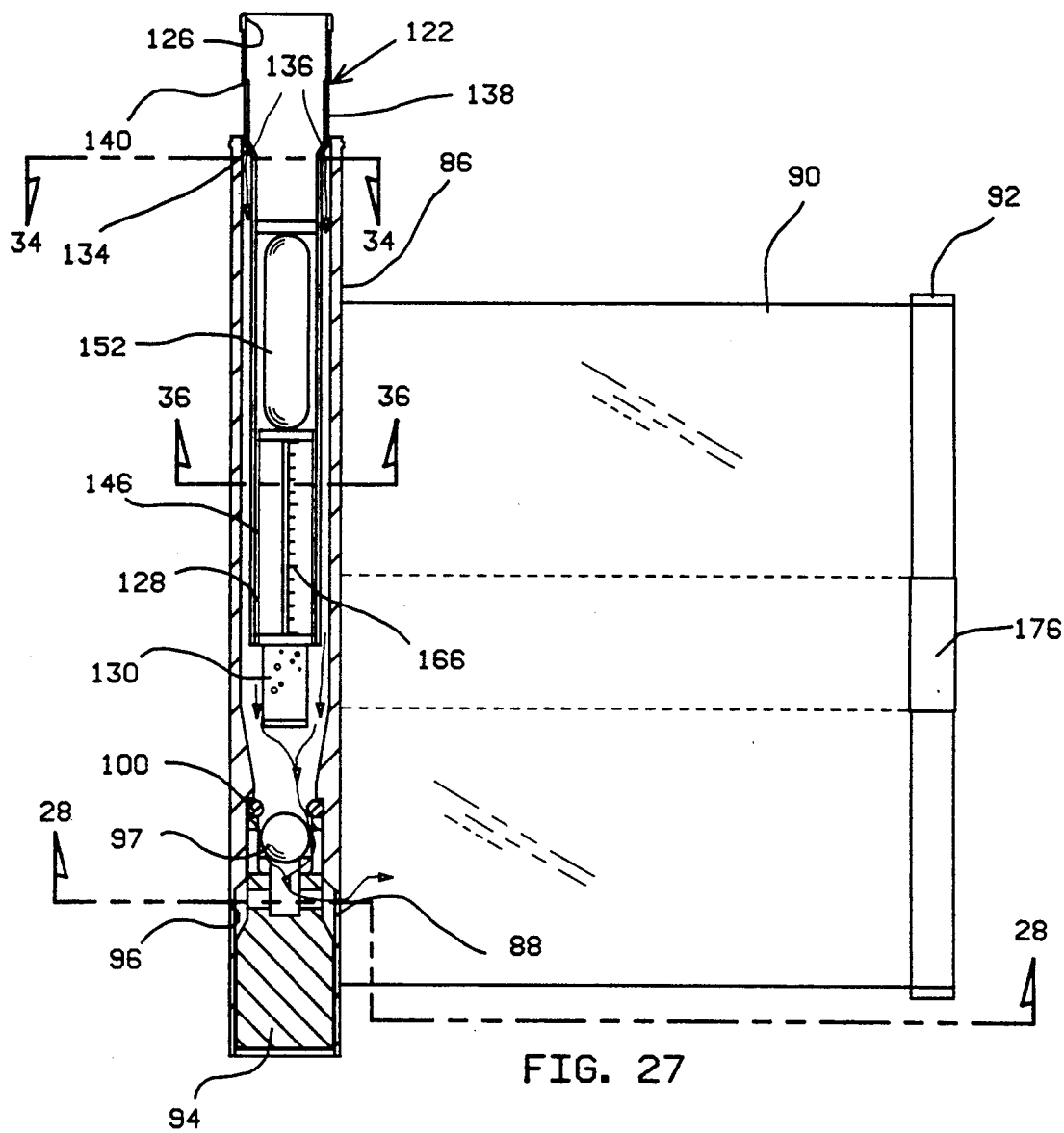
FIG. 27 is a side elevational view of the breath-sampling assembly of the present invention with the housing portions of the kit removed and showing the position of the parts and the flow of air when a user is blowing into the mouth piece to expand the inflatable bag and provide a known-volume of breath to be analyzed.
Figure 28:
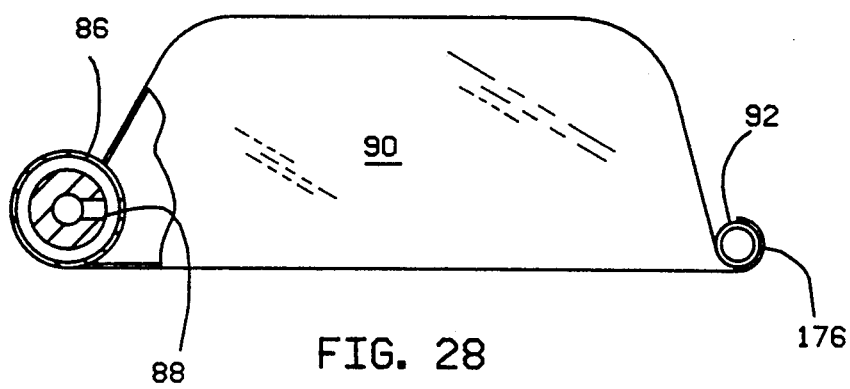
FIG. 28 is an end elevational view, partially in transverse section, of the assembly taken generally along the line 28—28 of FIG. 27.

To collect and test a sample of a person's breath using the breath-sampling kit disclosed herein, the cover (68) is first removed from the portable housing (52) to provide access to the open end of the blow tube (86) and also to permit inflation of the collection bag (90). When one of the disposable analyzer columns (122) is first inserted into the blow tube (86), it is important that one of the flats (138) on the mouth piece portion (126) be aligned with the raised marker (84) provided on the end wall (72) of the housing base (54). This ensures that neither of the flats (138) will be in initial alignment with the fourth rib (112) which, as can be seen in FIG. 23, is positioned 90° from the raised marker (84). Therefore, the inclined wall segment (134) engages the second or positive stop surface (116) on the rib (112) to limit further inward movement of the analyzer column (122). In this rotational and axial position of the analyzer column (122), the breath-sampling assembly (66) is in its breath-collecting mode wherein the parts are positioned as shown in FIGS. 27, 28, 34 and 37. In this mode, as best illustrated by the arrows in FIGS. 27, 28 and 37, the person whose breath is to be tested or monitored blows into the mouth piece (126) with the blown breath passing through the mouth piece (126), through the air openings (136) in the inclined wall segment (134) and longitudinally through the space defined between the inner surface of the blow tube (86) and the outer surface of the first reduced-diameter portion (128) of the analyzer column (122). This is the path of least resistance due to the frit filters (154, 150, 144 and 142) disposed within the analyzer column (122) The blown breath proceeds through the O-ring (100) and into the recess (98) provided in the valve housing (94), through the slots (106) around the ball valve (97), through the aligned valve housing bore (104) and the blow tube opening (88) into the inflatable/deflatable collection bag (90) As illustrated in FIGS. 27 and 28, the bag (90) is fully inflated against the force of a flat coil spring (176) which is adhesively secured to the outer surface of the bag (90) approximately midway between the opposite side edges thereof to provide a known volume of a user's breath. The spring (176) normally biases the bag (90) into the deflated rolled-up condition as shown in FIG. 23.

Once the bag (90) has been filled to its capacity, the user stops blowing and the bag (90) remains in its fully inflated condition inasmuch as the back pressure of the filled bag (90) forces the ball valve (97) into sealing engagement against the underside of the O-ring (100), as is clearly illustrated in the static mode of FIG. 38.

To discharge the collected sample of breath or air past the reactive material (162), the analyzer column (122) is first rotated 90° (in either direction) to align one of the flats (138) with the longest rib (112) (see FIG. 35) whereby the analyzer column (122) may now be advanced further into the blow tube (86) to its second rotational and axial position, best illustrated in FIGS. 29 and 39. In this deflation mode, the second reduced-diameter end portion (130) of the analyzer column (122) passes through and engages the O-ring (100) to seal off the external passage of lesser resistance, as well as forcing the ball valve (97) downwardly against its lower valve seat (108) This action permits the bag (90) to deflate, at a substantially constant rate due to the spring (176) with the discharged air passing from the bag (90) through the blow tube opening (88), the aligned valve housing bore (104), the slots (106) around the seated ball valve (97), and finally through the first frit filter (142) into the analyzer column (122). It then passes through the pretreatment zone (156), the reactive zone (160), the solvent zone (164), and out through the mouth piece (126), since the lesser resistance passage is blocked. The ampule (152) may then be broken by applying inward pressure on the breaker button (80) as previously described herein.

It is noted that the ball check valve (97) described herein could be replaced by other known type valve arrangements such as a flapper valve. To provide for air flow through the analyzer column (122) in the bag deflation mode when a flapper valve is used, transverse notches are provided in the inner end of the analyzer column (122).

The testing procedure has been thoroughly discussed previously herein in connection with the testing device of FIG. 1 and therefore will not be repeated herein.

After the breath-sampling test has been completed, the used analyzer column (122) is disposed of and a new analyzer column (122) can be used with the same kit (50) for a further test

Solvents

Suitable solvents must provide an environment in which ketone and aldehyde analytes may react with the nitroprusside and amine reagents of the invention. In embodiments of the invention where analytes are adsorbed onto preadsorbant materials suitable solvents must be capable of desorbing the analytes and transporting them to the reaction zone. Such solvents include methanol although a preferred solvent mixture comprises dimethyl sulfoxide (DMSO) and methanol at a 1:3 ratio by volume containing 30 mg/ml TRISMA-base. A particularly preferred solvent mixture is that comprising DMSO and methanol at a 1:3 ratio by volume containing 5 μl/ml N,N-diethanolamine (DEA).

EXAMPLE 9

In this example, the composition of the color developing solvent was optimized to provide for a dark blue (for acetone) color signal having a high background contrast. According to this example, vapor test devices were constructed according to the general details of FIG. 1 comprising test matrices according to Example 4. The matrices comprised nitroprusside-DEA and aminopropyl silica particles 250 to 400 microns in diameter with average pore diameters of 130 angstroms wherein the particles were present at a weight ratio of 1:2 and wherein the DEA-silica contained 50 mg of nitroprusside per gram of matrix. The devices were tested by administration of a test vapor comprising a 20 nM concentration of acetone in air. Various solvents were tested each comprising DMSO and methanol at a 1:3 (v/v) ratio in the presence of optionally substituted ingredients. Two-tenths of a milliliter of each of the test solvents was applied to the reaction zone and after five minutes, the height, color and degree of contrast of the color bar was judged with the results presented in Table 2 below. Use of the DMSO and methanol solvent alone gives generally poor results while incorporation of diethyl amine (Et$_2$NH) and triethylamine (Et$_3$N) improves the color and degree of background contrast Incorporation of TRIS buffer also results in improved color and background contrast with a preferred solvent mixture comprising DMSO and methanol at a 1:3 (v/v) ratio containing 30 mg/ml TRISMA-base. Most preferably, the solvent mixture comprises DMSO and methanol at a 1:3 (v/v) ratio containing 5 μl/ml DEA.

TABLE 2

OPTIMIZATION OF BLUE COLOR BAR PRODUCING DEVELOPING SOLVENT FOR BREATH ACETONE TEST IN ANALYZER COLUMN

| Developing solvent [DMSO-MEOH, 1:3 (v/v)] Plus Added | Breath Acetone Concentration (Nanomolar) | Height (mm) | Color | Background Contrast |
|---|---|---|---|---|
| None | 20 | 2 mm | Grey | Poor |
| 10 mg/ml TRIS | 20 | 3 mm | Purple | Fair |
| 20-30 mg/ml TRIS | 20 | 3 mm | Blue | Excellent |
| 30 mg/ml TRIS with 10 mg/ml Mg(OAc)$_2$ | 20 | 3 mm | Blue | Excellent |
| 30 mg/ml TRIS with 10 mg/ml Glycine | 20 | 3 mm | Blue | Excellent |
| 2-5 mg/ml Et$_3$N | 20 | 3 mm | Blue | Fair |
| 10-20 mg/ml Et$_3$N | 20 | 2 mm | Blue | Good |
| 2-5 mg/ml Et$_2$NH | 20 | 2 mm | Grey | Poor |
| 10-20 mg/ml Et$_2$NH | 20 | 3 mm | Blue-Grey | Fair |
| 2 μl/ml DEA | 20 | 3 mm | Blue | Good |
| 5 μl/ml DEA | 20 | 3 mm | Blue | Excellent |
| 10-20 μl/ml DEA | 20 | 3 mm | Blue | Good |

EXAMPLE 10

According to this example, vapor test devices were constructed according to the general details of FIG. 1 comprising test matrices according to Example 9. Alternatively, vapor detection devices were formed wherein DEA-silica contained 50 mg of nitroprusside per gram of matrix and was additionally treated with a solution of magnesium sulfate such that the matrix contained 20 mg of magnesium sulfate per gram of matrix.

The devices were then tested utilizing vapor samples containing calibrated concentrations of acetone. Acetone vapor samples ranging in concentration from 15 nM to 500 nM were tested in the devices of the invention as well as against a gas chromatograph (Shimadzu Model GC-8A, equipped with a heated gas sampler HGS-2 with a flame ionization detector and a chromosorb 102 3% 80-100 mesh). Results of the tests are shown on Table 3 below which confirm the existence of a relationship between acetone concentrations and the lengths of color bars. The results are highly reproducible and the height of the color bar may be read by an untrained consumer within an accuracy of 1 to 2 millimeters. At lower acetone concentrations, the results show production of darker, easier to read color with the magnesium treated matrices At acetone concentrations of 200 nM or greater, however, treated and untreated reaction matrices provide similar results

TABLE 3

RELATIONSHIP BETWEEN HEIGHT OF COLOR BAR AND ACETONE VAPOR CONCENTRATION

| | Height of Color Bar in 5 Min. (Millimeter) | | |
|---|---|---|---|
| Acetone Concentration (Nanomolar) | Untreated* | Magnesium Sulfate** Treated | Comments |
| 15 | 2.0 ± 0.6 (SD, n = 3) [Light Grey] | 2.5 ± 0.5 (SD, n = 3) [Dark Grey] | Darker color, easier to read in Mg treated |
| 30 | 4.7 ± 0.6 (SD, n = 3) | 4.6 ± 0.5 (SD, n = 3) | Darker color, easier to read |

TABLE 3-continued

RELATIONSHIP BETWEEN HEIGHT OF COLOR BAR AND ACETONE VAPOR CONCENTRATION

| Acetone Concentration (Nanomolar) | Height of Color Bar in 5 Min. (Millimeter) | | Comments |
|---|---|---|---|
| | Untreated* | Magnesium Sulfate** Treated | |
| 50 | [Light Blue] 5.5 ± 0.45 (SD, n = 3) | [Light Blue] 6.8 ± 0.3 (SD, n = 3) | Darker color, easier to read in Mg treated |
| 100 | [Light Blue] 11.7 ± 0.60 (SD, n = 3) | [Blue] 11.5 ± 0.50 (SD, n = 3) | Darker color, easier to read in Mg treated |
| 200 | [Blue] 17.2 ± 0.42 (SD, n = 6) | [Blue] 16.2 ± 0.30 (SD, n = 3) | Darker color, easier to read in Mg treated |
| 300 | [Dark Blue] 21.2 ± 0.48 (SD, n = 4) | [Dark Blue] 20.6 ± 0.76 (SD, n = 3) | Darker color, easier to read in Mg treated |
| 400 | [Dark Blue] 25.25 ± 0.87 (SD, n = 4) | [Dark Blue] 25.83 ± 0.41 (SD, n = 3) | Darker color, easier to read in Mg treated |
| 500 | [Dark Blue] 30.00 ± 0 (SD, n = 3) | [Dark Blue] 29.4 ± 1.1 (SD, n = 3) | Darker color, easier to read in Mg treated |

*Untreated matrix means DEA-silica, pore diameter 130A°, particle size 250-400 micron derivatized with 5 g/liter aqueous sodium nitroprusside solution and mixed with aminopropyl silica, pore diameter 130A°, particle size 250-400 microns in a weight ratio of 1:2.
**Magnesium sulfate treated matrix means same DEA-silica as above but derivatized with 5 g/liter aqueous sodium nitroprusside mixed with 2 g/liter of anhydrous magnesium sulfate, i.e., in equimolar amounts and then mixed with aminopropyl silica in a weight ratio of 1:2.

EXAMPLE 11

According to this example, vapor test devices were constructed according to the general details of FIG. 1 comprising various combinations of nitroprusside and amine-treated solid matrix materials. Concentrations of nitroprusside associated with the first solid matrix material were varied from 30 to 100 mg/gram of material while the weight ratio of nitroprusside-DEA silica to aminopropyl silica was varied.

According to the results (shown in Table 4, below), optimum results occurred with nitroprusside concentrations of 40 to 50 mg per gram of matrix. A particularly preferred combination was nitroprusside at a concentration of 50 mg/g with a nitroprusside DEA to aminopropyl silica ratio of 1 to 2 by weight.

TABLE 4

OPTIMIZATION OF NITROPRUSSIDE-DEA SILICA* AND AMINOPROPYL SILICA** MIXTURES FOR BREATH ACETONE TEST IN ANALYZER COLUMN

| Nitroprusside Concentration (mg/g of Matrix) | Nitroprusside-DEA and Aminopropyl Silica Weight Ratio | Breath Acetone Concentration (Nanomolar) | Readability of Blue Color Bar (Background Color) |
|---|---|---|---|
| 100 | 1:1 | 20 | Difficult (Dark Grey) |
| 100 | 1:1.5 | 20 | Difficult (Dark Grey) |
| 100 | 1:2 | 20 | Difficult (Dark Grey) |
| 80 | 1:1 | 20 | Difficult (Dark Grey) |
| 80 | 1:1.5 | 20 | Difficult (Dark Grey) |
| 80 | 1:2 | 20 | Difficult (Dark Grey) |
| 60 | 1:1 | 20 | Fair (Light Grey) |
| 60 | 1:1.5 | 20 | Fair (Light Grey) |
| 60 | 1:2 | 20 | Fair (Light Grey) |
| 50 | 1:1 | 20 | Fair (Light Grey) |
| 50 | 1:1.5 | 20 | Good (Light Grey) |
| 50 | 1:2 | 20 | Excellent (Tan) |
| 40 | 1:1 | 20 | Good (Light Tan) |
| 40 | 1:1.5 | 20 | Good (Light Grey) |
| 40 | 1:2 | 20 | Good (Tan) |
| 30 | 1:1 | 20 | Difficult (Light Tan) |
| 30 | 1:1.5 | 20 | Difficult (Light Tan) |
| 30 | 1:2 | 20 | Difficult (Light Tan) |

*DEA silica used was obtained from Diagnostic Specialties/Separation Industries, having the following properties: particle size, 250-400 microns; pore diameter, 130 angstroms; surface area, 194 m²/g; settle volume, 1.8 cc/g; 10.90% C; 0.85% N and 2.17% H.
**Aminopropyl silica was obtained from Diagnostic Specialties/Separation Industries, having the following properties: particle size, 250-400 microns; pore diameter, 130 angstroms; surface area 194 m²/g; settle volume, 1.8 cc/g; 6.67% C; 1.64% H and 2.42% N.

Ketones and aldehydes other than acetone will react with the materials of the present invention While acetone reacts with the nitroprusside and aminopropyl silica materials in the present of suitable solvents to produce a blue reaction product, other ketones and aldehydes in the presence of these materials and in the presence of alternative amine materials will react to produce reaction products with differing colors. The color of a reaction product thus produced is therefore indicative of the type of ketone or aldehyde present while the length of the color bar produced provides a quantitative determination of the concentration of the ketone or acetone

Head Space Analysis

Concentrations of ketones and aldehydes present in liquid samples may be determined utilizing the same methods and materials of the invention used for analysis of vapor. According to well known procedures, however, head space vapor in equilibrium with the liquid sample to be analyzed is collected and analyzed according to procedures for analyzing vapor samples Ketone and aldehyde vapor concentrations may be related to liquid sample concentrations through use of known vapor pressure and partition coefficient relationships. Head space analysis is useful for the determination of concentrations of more volatile ketone and aldehyde sample components and is particularly useful for the determination of acetone concentrations in aqueous samples. Detection of acetone in such aqueous samples is otherwise hampered by the interference of water with the nitroprusside/amine color reaction. Vapor collected by head-space analysis may be desiccated according to the methods disclosed above in order to prevent the adverse effects of water on the color reaction.

LIQUID ASSAY DEVICES

The present invention also provides methods and devices for the direct quantitative and semiquantitative analysis of ketones and aldehydes present in liquid samples. Assay devices suitable for direct analysis of liquid samples are particularly useful as head space vapor analysis according to the invention tends to be primarily suitable for analysis of more volatile analytes. Direct liquid assay devices according to the invention include microcolumns for capillary adsorption of liquid samples and dipsticks for dipping into liquid samples. Suitable sample materials for testing according to the present invention include various laboratory and industrial reagents as well as physiological fluids including urine, serum and other materials. Devices according to the invention include a first solid matrix material to which a nitroprusside salt has been coupled and a second solid matrix material to which an amine is covalently bound. This allows the stable formation of color complexes after reaction of the matrix with analytes such as acetoacetic acid. Such stable color formation in turn facilitates the semiquantitative analysis of ketones and aldehydes through colorimetric methods including comparisons with color charts and use of spectrophotometers.

Figure 4:
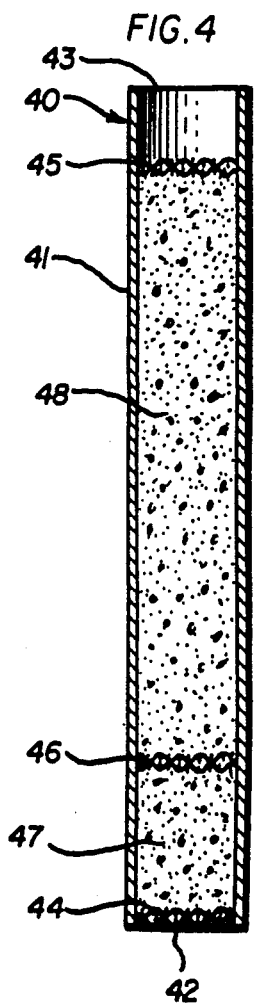
FIG. 4 is a view of a liquid test device of the present invention.

FIG. 4 depicts a "microcolumn" assay device (40) suitable for ascending chromatographic analysis of liquid samples according to the invention. The device comprises an inert microcylinder (41) having a first end (42) and a second end (43). Flush with the first end (42) is a first porous barrier (44). A second porous barrier (45) is flush with or spaced from the second end (43) of the device, while an optional third porous barrier (46) is located in the interior of the device spaced from the first end (42). The first porous barrier (44) and third porous barrier (46) define a diffusion zone, the purpose of which is to slow down the rapid infusion of sample material. The diffusion zone is filled with an inert substance such as cellulose powder which is capable of promoting liquid diffusion The second (45) and third (46) porous barriers define a reaction zone (48) which comprises a mixture of the first solid matrix material to which a nitroprusside salt is coupled and a second solid matrix material to which an amine is covalently bound.

According to a procedure for use of device (40) of FIG. 4, the device is dipped at its first end (44) in a sample of a liquid to be assayed. The liquid rises through capillary action through the first porous barrier (44) into the diffusion zone (47) and then continues through the third porous barrier (46) into the reaction zone (48). Ketones and aldehydes present in the sample liquid there react with the nitroprusside salt and the amine presented by the first and second solid matrix materials to form a colored reaction product. The sample liquid continues to diffuse into the device (40) and into the reaction zone (48) until the liquid reaches the second porous barrier (45) and capillary transport ceases. After a suitable waiting period for formation of color, the colored reaction product is observed and the concentration of analytes present in the sample liquid is determined spectrophotometrically or by comparison with color charts.

Microcylinders

The microcylinders from which the microcolumn devices of the invention are fabricated preferably comprise a material which will neither adsorb nor react with the analytes or reagents of the assay. The microcylinder materials are preferably transparent in order that the presence of a color reaction product may be detected and evaluated. Preferred materials include transparent plastics such as polystyrene and polyethylene terephthalate. Glass tubes are acceptable but columns fabricated from polyethylene terephthalate are particularly preferred.

The microcylinders may generally be of any size and geometry selected to contain sufficient reagents to analyze a sample of a selected size. Column diameters preferably range from about 1.0 mm to about 3.0 mm with preferred column lengths ranging from about 10 mm to about 40 mm.

Porous Barriers

Porous barriers suitable for the liquid assay devices of the present invention include those porous barrier material suitable for conducting vapor assays including materials such as nylon fabric, glass wool, sponge and styrofoam. A particularly preferred porous barrier material for use with the liquid assay devices of the present invention is nylon fabric.

EXAMPLE 12

According to this example, microcolumn devices of the invention were fabricated by covering microcylinders (1.5 mm by 50 mm) with a piece of nylon fabric at one end. The cylinders were each then filled with an amount of cellulose powder sufficient to fill a 5 mm length of the tube (Whatman Chemical Separation, Ltd., U.K.; microgranular cc 41, Cat. #4061-050). The columns were then filled to a height of 40 mm with a mixture of nitroprusside-DEA and aminopropyl silica (1:2 by weight), with a pore diameter of 200 Å (angstroms), and average particle size of 40 to 60 microns as described in Example 4. The top of the silica matrix was then covered with 1 mm thick nylon fabric as before. A vibrator (Vibrograver, Supelco, Inc. Bellefonte, Pa.) was used to pack each of the microcolumns uniformly. After packing, the columns were stored in a dark bottle at room temperature. The devices may not only be used for semiquantitative analysis through spectrophotometric techniques or reference to color charts, but is particularly useful for the quantitative detection of ketone and aldehydes through the use of ascending chromatographic techniques

EXAMPLE 13

According to another aspect of the invention, "dipstick" devices may be fashioned wherein the solid matrix material of the invention is used in suitable shapes such as films, strips or sheets. The materials may also be coated onto, or bonded or laminated to appropriate inert carriers by using glue or adhesive by mixing with binders or by heat treatment and the compression of the particles onto plastic surfaces Suitable materials include paper, glass, plastic, metal or fabrics. The matrix material is preferably in the form of strips of thickness in the range from about 0.10 mm to about 1 mm, and most preferably of about 0.25 mm. The strips preferably range from 2 mm to 4 mm wide and from 2 mm to 4 mm long, but may be virtually any dimension consistent with economy and sample size According to one procedure, polystyrene sheets, 0.025 mm thick, were obtained (Vinyl Plastics, Inc., Milwaukee, Wis., Cat. #1045), and were sprayed uniformly with an adhesive (Scotch 3M Spray Mount Adhesive, Cat. #6065). The sheets were then sprayed with a mixture of nitroprusside-DEA-silica and aminopropyl silica (1:2 by weight) with a pore diameter of 200 Å and particle size of 40–60 microns. Alternatively, the sheets were treated with a mixture of nitroprusside-DEAE-cellulose and aminopropyl silica (1:4 and 2:1 by weight) as described in Example 7. Excess particles which did not stick to the glued surface were removed by tapping.

The coated strips were then cut in small pieces (4 mm×2 mm size) attached to double-faced adhesive tape and used to measure acetoacetic acid concentration in urine samples. According to an alternative procedure, dipsticks were fashioned from Gel Bond Strips (FMC Corp., Rockland, Me.). According to this method, 100 mg of nitroprusside-DEA silica and aminopropyl silica at a 1:2 ratio by weight and 100 mg nitroprusside-DEAE cellulose and aminopropyl silica at 1:4 and 2:1 ratios by weight were each mixed with 80 μl hydroxyethyl cellulose agarose (5%) (FMC Corp., Rockland, Me.) and 50 microliters hydroxy propyl cellulose (0.5%) obtained from Hercules, Hercules, Del. taken in 470 microliters of water at 50° C. Twenty microliters of the resulting slurry was pipetted onto each Gel Bond Strip (4 mm×2 mm size). After allowing the strip to air-dry in the dark at room temperature for roughly two to three hours, the strips were used to measure the acetoacetic acid concentration in urine samples.

EXAMPLE 14

In this example, a solid matrix comprising nitroprusside-DEA silica according to Example 1 and aminopropyl silica according to Example 2 in a weight ratio of 1:1 or 1:2 was incorporated in a microcolumn as described in Example 12. In order to test the devices, known amounts of acetoacetic acid were added to various buffers and to fresh urine samples from normal subjects whose acetoacetic concentrations were determined to be less than 1 mg/dl. Urine solutions were discarded after being stored for 2 hours at 4° C.

TABLE 5

| Sample | Concentration of Acetoacetic Acid (mg/dl) | | | | | |
|---|---|---|---|---|---|---|
| Urine pH 5.0–7.0 | 100 | 50 | 25 | 10 | 5 | 1 |
| Acetate buffer pH 4.0 | " | " | " | " | " | " |
| Borate buffer pH 8.0 | " | " | " | " | " | " |
| Tris buffer pH 9.5 | " | " | " | " | " | " |

The devices gave positive color results for the urine samples within one minute. The colors varied according to the concentration of the sample and ranged from dark purple/magenta for the 100 mg/dl sample to light pink for the 1 mg/dl sample. Urine samples not spiked with acetoacetic acid gave a slightly yellowish-tan color. The sensitivity threshold in all cases was 1 mg/dl. The colors were stable for a period of 72 hours and the amount of acetoacetic acid could be accurately determined over that period by comparison with a color chart.

EXAMPLE 15

In this example, the devices of Example 12 were tested against buffer solutions at pHs 4.0, 7.3, 8.0 and 9.5 to which varying amounts of acetoacetic acid has been added as shown in Example 14, Table 5. The test columns gave positive colors within one minute with colors being very similar to those observed with the urine samples as in Example 14. Control buffers not spiked with acetoacetic acid gave a slightly yellowish color. The sensitivity threshold in all cases was 1 mg/dl. The colors were stable for a period of 72 hours and the amount of acetoacetic acid could accurately be determined over that period by comparison with a color chart.

EXAMPLE 16

In this example, a solid matrix comprising nitroprusside-DEAE-silica according to Example 1 and aminopropylsilica according to Example 2 in a 1:2 (by weight) ratio was incorporated onto a polystyrene sheet or Gel Bond Strip as described in Example 13. The device was tested against the urine samples of Table 5 and gave positive color results for all samples within one minute. The colors varied according to the concentration of the sample and ranged from dark purple/magenta for the 100 mg/dl sample to light pink for the 1 mg/dl sample. Urine samples not spiked with acetoacetic acid gave a slightly yellowish-tan color. The sensitivity threshold in all cases was 1 mg/dl. The colors were stable for a period of 72 hours and the amount of acetoacetic acid in the samples could accurately be determined over that period by comparison with a color chart.

EXAMPLE 17

In this example, the dipstick devices of Example 13 were tested against the buffer solutions of Table 5 at pHs 4.0, 7.3, 8.0 and 9.5 to which varying amounts of acetoacetic acid had been added according to Example 15 (Table V). The test strips gave positive colors within 1 minute with the colors very similar to those observed with the urine samples of Examples 14 and 16. Control buffers not spiked with acetoacetic acid gave a slightly yellowish color. The sensitivity threshold in all cases was 1 mg/dl. The colors were stable for a period of 72 hours and the amount of acetoacetic acid in the samples could accurately be determined by comparison with a color chart.

EXAMPLE 18

In this example, dipstick devices according to Example 13 were constructed wherein the solid matrix comprised nitroprusside-DEAE-cellulose and aminopropylsilica in weight ratios of 1:2 and 1:4. These devices were tested against the urine and buffer solutions (at pHs 4.0, 7.3, 8.0 and 9.5) to which varying amounts of acetoacetic acid had been added according to Table 5. These devices gave the same results as the devices of Examples 14, 15, 16 and 17.

EXAMPLE 19

In this example, dipstick devices according to Example 12 were constructed wherein the solid matrix comprised nitroprusside-DEAE-cellulose and aminopropylcellulose in weight ratios of 1:4 and 1:8. The dipsticks were constructed of polystyrene sheets or of Gel Bond and tested against the urine and buffer solutions (at pHs 4.0, 7.3, 8.0 and 9.5) of Table 5. The devices were sensitive to acetoacetic acid and gave colors ranging from light purple to faint purple which were visible for 48 hours. The sensitivity limit ranged from between 5 to 10 mg/dl

EXAMPLE 20

In this example, microcolumn chromatography devices were constructed according to Example 12. The devices were packed with solid matrix material comprising nitroprusside-DEAE-silica and aminopropyl silica at a ratio of 1:2 by weight. The devices were immersed in 300 μl of a standard solution comprising acetoacetic acid in 0.2 molar phosphate buffer (pH 6.8) containing 0.9% sodium chloride which rose through the columns by capillary action. In rising through the device, acetoacetic acid within solution reacted with the matrix materials to produce a purple reaction product which was stable for 24 hours. The amount of acetoacetic acid could therefore be determined by measuring the length of the color bar. The elution took approximately ten minutes but it would be possible to shorten this time as may be desired. Table 6 below shows the relationship between acetoacetic acid concentration and the height of the color bar.

TABLE 6

| Acetoacetic Acid Concentration (mg/dl) | Height of Color Bar* (Millimeter) | Color |
| --- | --- | --- |
| 100 | 30 | Dark Violet |
| 50 | 22 | Dark Violet |
| 25 | 16 | Dark Violet |
| 10 | 7 | Medium Violet |
| 5 | 4 | Medium Violet |
| 1 | 2 | Light Violet |

*Average of two experiments.

EXAMPLE 21

In this example, the devices of Example 20 were used to detect the presence of acetoacetic acid in urine samples to which acetoacetic acid had been added. Seven samples were tested with linear color bars detected in four of the samples. The color bar heights in four samples were very similar to those depicted in Example 20, Table 6. The other three samples did not produce linear color bars but rather produced color bars which were more elongated and diffused. It is believed that the failure of certain of the samples to produce elongated color bars is a consequence of the presence of high salt concentrations in the urine.

EXAMPLE 22

In this example, urine samples were diluted to one-tenth their original concentration with water in order to prevent interference of the salt solutions with the chromatography. Various samples were tested with the micro column capillary devices of Example 14. The results are shown in Table 7 below.

TABLE 7

| RELATIONSHIP BETWEEN HEIGHT OF COLOR BAR AND TEN-FOLD DILUTED URINE SAMPLES | |
| --- | --- |
| Acetoacetic Acid Concentration (MG/DL) | Height of Color Bar* (Millimeter) |
| 100 | 11 ± 3 |
| 50 | 9 ± 2 |
| 25 | 7 ± 2 |
| 10 | 5 ± 2 |

*Average of seven experiments.

EXAMPLE 23

In this example, the bifunctional solid matrix material of Example 8 comprising both nitroprusside and aminopropyl functions coupled and bound to the same matrix was tested according to the procedure of Example 16 for the detection of acetoacetic acid in aqueous solutions. The materials were only slightly sensitive to acetoacetic acid in buffers (pH 6.8). Only a faint purple color was detected at 100 mg/dl of acetoacetic acid. The sensitivity was increased by addition of Trisma base (pH 10.0) to about 20 mg/ml of acetoacetic acid. When aminopropyl silica was added to the matrix material, this increased sensitivity to about 20 mg/ml of acetoacetic acid. The device of Example 16 was also tested for sensitivity to acetone in the presence of dimethylsulfoxide and methanol (v/v, 1:3) containing 30 mg/ml Trisma base. The sensitivity limit was approximately 7 nm of acetone in solution. A faint blue was detected which could be slightly enhanced by addition of aminopropyl silica to the mixed matrix material.

MONITORING OF WEIGHT LOSS

In the course of development of the devices of the present invention it was discovered that serum acetone concentrations and hence breath acetone concentrations as measured by the methods and devices of the present invention may be correlated directly with the rate of fat-metabolism (fat-loss) experienced by a subject undergoing a weight loss dietary regimen comprising fasting, dieting, exercise or a combination of the aforesaid.

The invention comprises methods for ascertaining the fat catabolism effects of a weight loss dietary regimen comprising (a) periodically assaying breath for acetone content and (b) correlating breath acetone to a standard reflecting the effect on breath acetone of fixed rates of fat catabolism. A direct correlation between alveolar air (breath) concentrations and the rate of fat-loss has been established. Because breath acetone concentrations are directly proportional to serum acetone concentrations, the correlation between acetone and the rate of fat-loss also holds for serum acetone. References to breath acetone concentrations will therefore, unless otherwise stated, also refer to the serum acetone concentrations which are specifically associated therewith.

Methods for determining the fat catabolism effects of a weight loss dietary program involve the collection of alveolar air (breath) samples and assaying for acetone content. Various methods may be utilized for determination of sample acetone concentrations including mass spectrometry and gas chromatography with preferred methods utilizing the ketone assay devices of the invention. Such assay devices may be provided in which tabular color charts are calibrated to indicate a rate of fat catabolism expressed in suitable units such as pounds of fat catabolized per week. Assay devices comprising a linear reading system may comprise a graphic adjunct such that a color bar scale may be calibrated to indicate a rate of fat catabolism expressed in units such as pounds of fat catabolized per week. Breath may be sampled on a periodic basis such as once daily with samples preferably collected before breakfast in the morning. Breath samples may be taken more frequently than once daily, although samples taken soon after consumption of a meal or after the completion of exercise may indicate lower or higher rates of fat catabolism, respectively, than would be expected to be maintained over a 24 hour period.

EXAMPLE 24

In this example, breath acetone concentrations were measured for a group of dieting individuals and controls utilizing a Shimadzu gas chromatograph (Model GC-8A, Columbia, Md.) equipped with a heated gas sampler HGS-2 and a flame ionization detector The chromatographic consisted of a 2 meter stainless steel coil, 1/8 inch OD packed with chromosorb 102 3% 80-100 mesh (Supelco, Inc.). The column temperature was maintained at 120° C. with ultrapure helium as a carrier gas (5 kg/cm² pressure). Hydrogen and air pressures were 0.5 kg/cm² and 0.2 kg/cm², respectively. The retention time of acetone was 4.2 minutes and the acetone peak was well separated from the methanol, ethanol, isopropanol and acetaldehyde peaks Calibrations were made by preparing acetone vapor in glass gas jars or from commercially available cylinders containing a compressed air-acetone mixture (Linde Div., Union Carbide). Calibration standards ranging from 4-1000 nanomole/liter were used to demonstrate a linear relationship between the height of the acetone peak and the concentration of acetone in a sample. A Shimadzu C-3RA integrator was used for calibration purposes In order that breath samples taken from different individuals at different times provide accurate and reproducible results, several types of expired breath specimens were tested for acetone concentration. Several types of expired breath samples are suitable for chemical analysis including (1) expired alveolar air; (2) end-tidal air; (3) end-expiratory air and (4) re-breathed air. Mixed expired air is not suitable for breath analysis because it contains variable proportions of alveolar air and dead-space air.

Various types of breath samples were collected from a number of volunteers by methods including (a) end-tidal air by collection of the last part of a big breath; (b) end-expiratory breath specimen by means of a device (Intoximeter, Inc., St. Louis, Mo.) according to the method of Dubowski, Clin. Chem. 20, 966 (1974) and (c) equilibrated vital capacity air by holding a deep breath for 5 seconds and expelling various fractions of the breath according to the method of Erikson, New Scientist, 381, 608 (1964), the disclosure of which is hereby incorporated by reference. The acetone content of all collected specimens showed differences of less than 2% between the various methods It was thus concluded that diagnostically useful samples could be obtained simply by holding a deep breath for 5 seconds and expelling the entire breath to obtain a sample of equilibrated vital capacity air. For analysis of breath acetone by gas chromatography, volunteers were asked to take a deep breath, hold for 5 seconds and blow into a silicone coated balloon (1 liter capacity) via a one-way valve and T-connection connected to the gas inlet of a gas chromatograph. After the gas-loop was purged for 10 seconds with a breath sample, a constant volume of 1 cc was allowed to be swept into the chromatographic column for analysis.

EXAMPLE 25

In this example, a diet study was conducted with 170 normal volunteers who were between 0 and 100 pounds above desirable body weight for height according to the Metropolitan Life Height/Weight table. The criteria for selection of volunteers were that they were normal in other respects, had completed a physical examination within the previous 12 months and did not fall into one or more of the following categories: (1) pregnant women; (2) individuals taking lithium salts for depression; (3) individuals with renal or hepatic disease requiring protein restriction; (4) individuals with arteriosclerotic heart disease; (5) diabetics receiving insulin or oral hypoglycimic agents; and (6) individuals with cardiac arrythmias.

The diet program continued for two weeks and the diet included fish, poultry, lean beef, eggs, vegetables, salad, cottage cheese, coffee, tea, sugar free gelatin, and not more than 2 cans of diet soda. Each volunteer was allowed to plan his own daily diet plan, none of which exceeded the limits of 1200 calorie, 40 grams of fat and 40 grams of carbohydrate on any day. Each volunteer also took one multivitamin plus mineral tablet and at least 1500 ml fluid per day.

Breath acetone concentrations of each individual were measured early in the morning before breakfast by gas chromatography according to the procedure of Example 24 as well as by the colorimetric method according to Example 11. Urine concentrations of acetoacetic acid were measured by Ketostix (Miles Laboratories, Elkhart, Ind.) as well as by the method according to Example 14. The body weight of each volunteer was also recorded prior to breakfast.

All subjects participating in the program lost between five and ten pounds of body weight in the first week of the diet. The specific amount of weight loss depended on the obesity, gender and level of physical activity of the individual. While it is generally accepted that women in general have lower metabolic rates than men, Wynn, et al., Lancet, 482 (1985), this was confirmed by the study. It was also found that the rate of fat-loss, and hence development of ketosis is dependent on the extent of obesity of an individual, with severely obese individuals losing fat and becoming ketotic at a slower rate than less obese individuals.

It was noted that the rate of fat-loss and increase in breath acetone also depends on individual's physical activity, e.g., a person on a diet and additionally performing physical activity such as aerobics, bicycling or jogging, has a higher breath acetone concentration and rate of fat-loss than one who is on a diet only and not doing any physical exercise.

Figure 5:
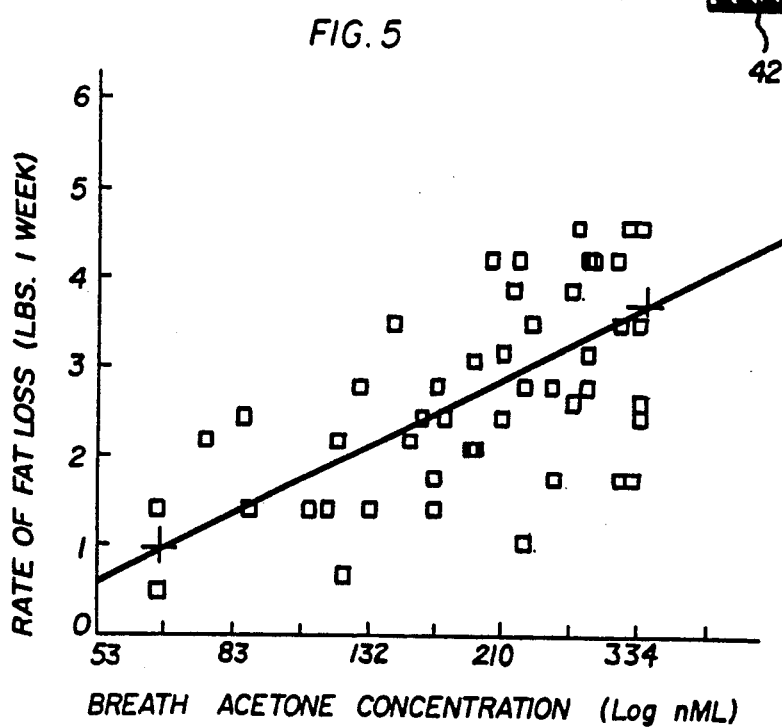
FIG. 5 is a graph illustrating the relationship between breath acetone concentrations and the rate of fat loss corresponding thereto.
Figure 3:
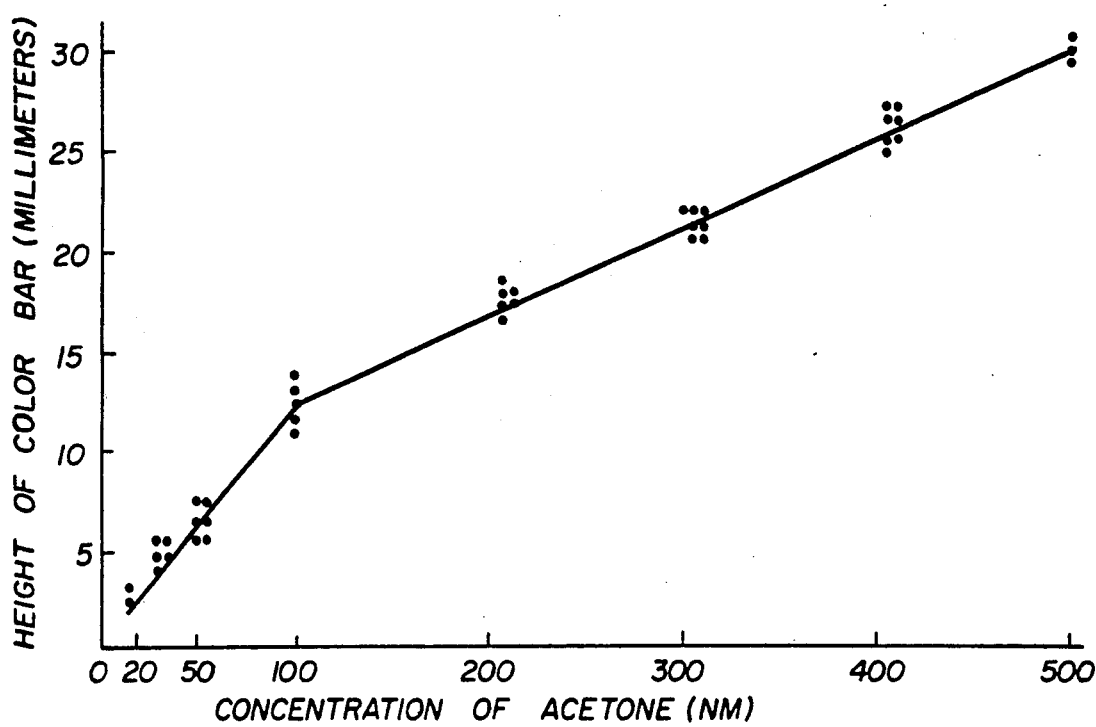
FIG. 3 is a graph illustrating the relationship between the height of the color bar in a vapor test device of the present invention and the concentration of acetone present in a vapor sample.
Figure 6:
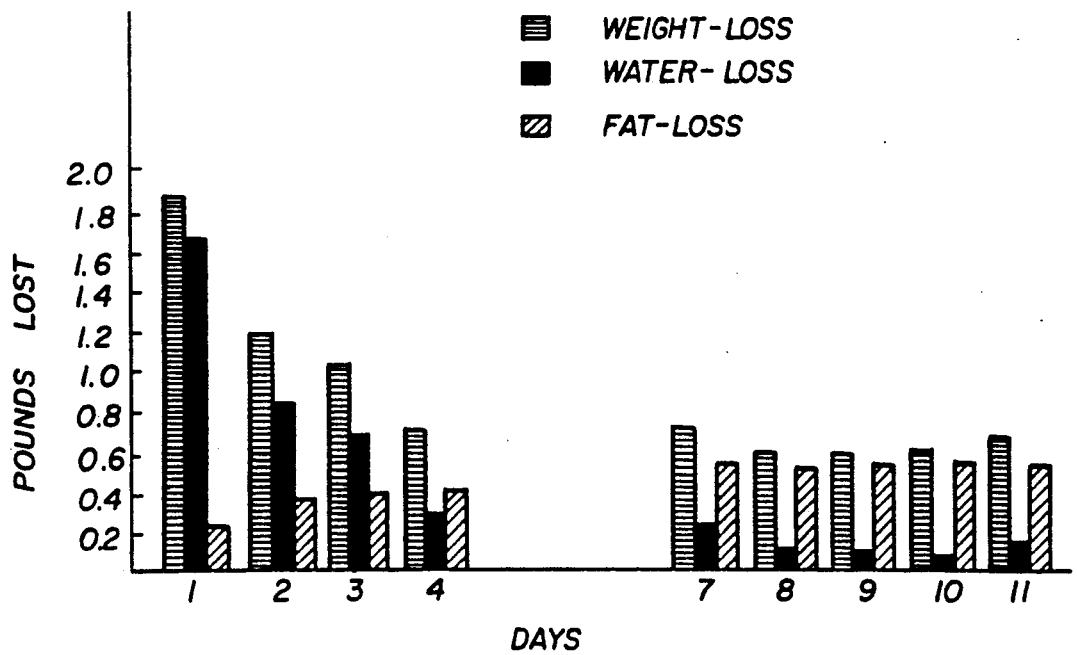
FIG. 6 is a graph illustrating the degree of water and fat loss for dieters 0 to 10 pounds overweight over a period of days.
Figure 7:
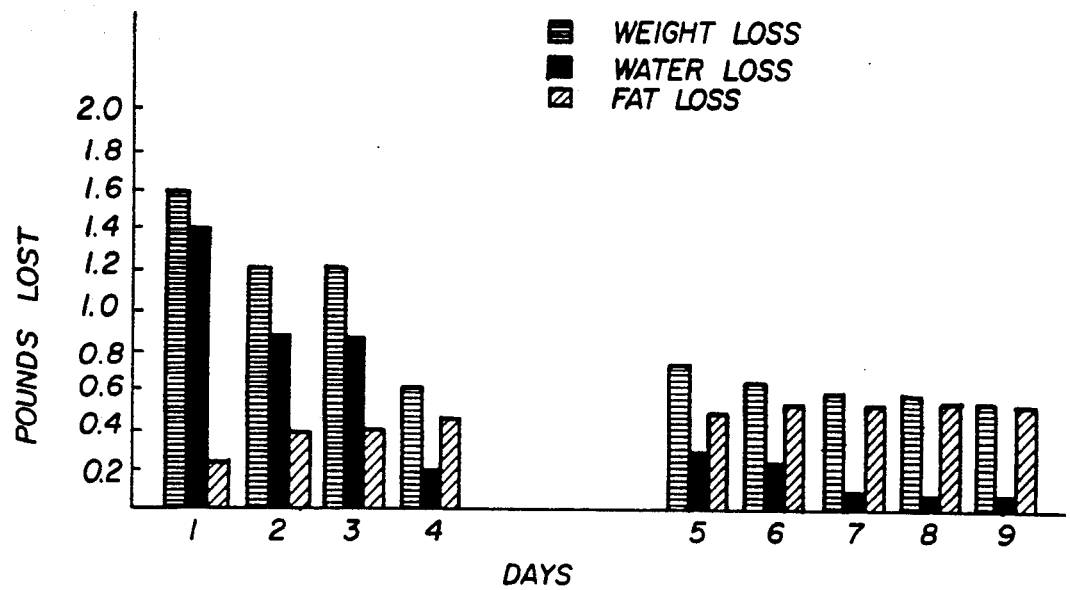
FIG. 7 is a graph illustrating the degree of water and fat loss for dieters 10 to 20 pounds overweight over a period of days.
Figure 8:
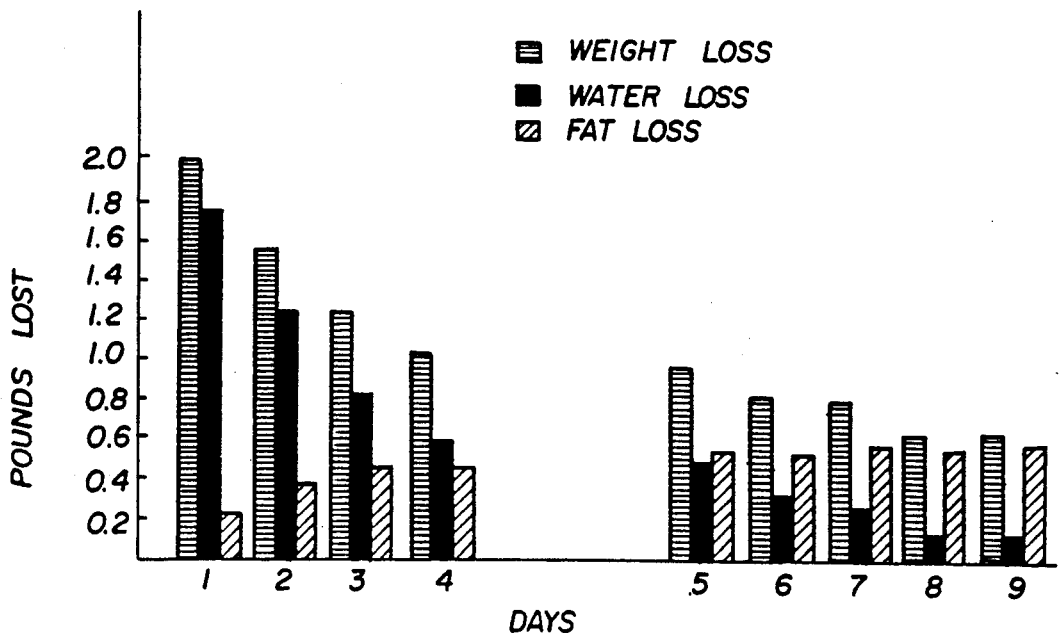
FIG. 8 is a graph illustrating the degree of water and fat loss for dieters 20 to 40 pounds overweight over a period of days.
Figure 9:
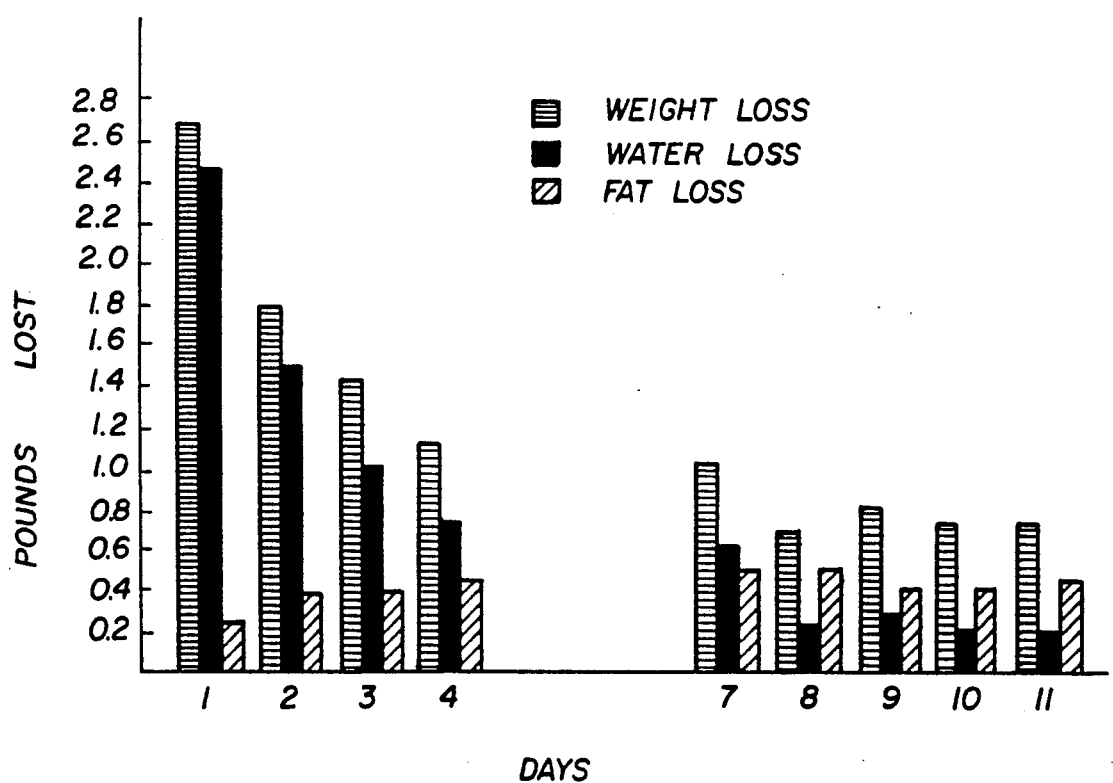
FIG. 9 is a graph illustrating the degree of water and fat loss for dieters 40 to 100 pounds overweight over a period of days.

The relationship between rate of fat-loss and serum/breath acetone concentration was determined by analysis of the subjects of the example during their second week of dieting. More than 50% of the weight lost in the first week of the diet was due to water loss. By comparison, in the second week of dieting, the amount of water loss for those subjects between 0 and 20 pounds overweight became minimal, approaching 10 to 15% of weight loss, and the loss in body weight was primarily due to fat catabolism. FIG. 5 illustrates the data from individuals between 0 and 20 pounds overweight during the second week of the diet. The "straight line", calculated by linear regression, gives the statistical value of the relation between breath acetone concentration and rate of fat-loss in pounds per week. The relation between breath acetone, fat-loss and calories burned is shown in Table 8 below.

TABLE 8

RELATIONSHIP BETWEEN BREATH ACETONE CONCENTRATION, FAT LOSS AND CALORIE BURNED DURING DIETING

| Breath Acetone[a] Concn. (NM) | Fat-Loss[b] | | Calories Burned[c] Per Day |
|---|---|---|---|
| | Per Day (lbs) | Per Week (lbs) | |
| 8–30 | — | — | — |
| 50 | 0.07 | 0.5 | 286 |
| 67 | 0.14 | 1.0 | 572 |
| 120 | 0.28 | 2.0 | 1144 |
| 212 | 0.43 | 3.0 | 1757 |

TABLE 8-continued
RELATIONSHIP BETWEEN BREATH ACETONE CONCENTRATION, FAT LOSS AND CALORIE BURNED DURING DIETING

| Breath Acetone[a] Concn. (NM) | Fat-Loss[b] Per Day (lbs) | Per Week (lbs) | Calories Burned[c] Per Day |
|---|---|---|---|
| 330 | 0.5 | 3.5 | 2043 |

[a]Breath acetone concentration was calculated by gas chromatography and colorimetric method of Example 10.
[b]Fat-loss was calculated from the slope of the straight line (shown in FIG. 5)
[c]Calorie burned was devised from the relationship between calories and fat consumption: 1 g fat burned = 9 calorie.

The weight, water and fat-loss profiles of dieters are shown in FIGS. 6 through 9. The values for fat-loss were calculated from the breath acetone measurement and the standard obtained by determination of the slope of the straight line in FIG. 5. The values for water-loss were calculated by subtracting from the actual body weight. It should also be noted that in the first week of dieting, the fat-loss figure accounts for the loss of glycogen carbohydrate stores in addition to loss of body fat.

It was found that urine acetoacetic acid has no direct relationship with fat-loss Although an increase was clearly noted with all dieters after 2 to 3 days of dieting, the increase was not quantitatively related to breath acetone concentrations or to the rate of fat-loss. The blood sugar levels of the dieters did not change during the dieting period.

EXAMPLE 26

In this example, a diet program was conducted for one month with 30 otherwise normal 40-100 pound overweight volunteers. This established that the direct linear relationship between breath acetone and fat-loss exists beyond two weeks using the same low-fat/low carbohydrate diet. The selection of the subjects was the same as in the two-week program except all the subjects had to undergo complete physical examination, laboratory tests including complete blood count, serum chemistries (SMCC 12 or 20) and urinalysis before participation. Breath acetone, urine ketone and body weight of each individual were measured daily and blood sugar level determined weekly. It was noted that volunteers in this group tend to lose water for a longer period of time than less obese people It was found that for this group, the water-loss becomes minimum (10-15%) in the third week (FIG. 9) It was also found that breath acetone concentrations of subjects in this group were directly proportional to their fat-loss in the third and fourth week as well as in the second week. Although urine acetoacetic acid concentrations of each individual were elevated, there was no direct relationship to the rate of fat-loss. No changes in blood sugar levels were noted.

It is interesting to note that more obese people tend to lose water for a longer period of time. For the group who are between 0-10 pounds overweight, the water-loss becomes minimal (<15%) on day 8, for 10-20 pounds overweight the day shifts to day 9 and for 20-40 pounds overweight it shifts to day 10. People who are between 40-100 pounds overweight, the water-loss continues in the second week of dieting and becomes minimal (<15%) on day 14.

The program also indicated that water-loss in four very obese subjects (100-200 pounds overweight) continues for a much longer time and fluctuates even in the week 4. This group developed ketosis at a slower rate than the other less obese groups and also experienced a lower rate of fat loss.

EXAMPLE 27

In this example, a group of subjects enhanced the extent of their ketosis by participating in physical exercise without decreasing their daily calorie intake. An increase of 20-40% in breath acetone was observed after burning 400-500 calories by physical exercise (bicycle or jogging) Immediately after physical exercise, there was a drop in breath acetone level which then slowly rose after 1 hour and plateaued after 4 to 5 hours.

It was found that ketosis (breath acetone) drops considerably for volunteers when they don't perform exercise on any given day. As a typical illustration, a male subject with a daily intake of 1000 calorie, 30 to 40 grams of fat, and 30 to 40 grams of carbohydrate plateaued at a breath acetone level of 100 nM from the 8th day onwards. He did not perform any rigorous physical exercise. On day 11, he rode on a bicycle for 10 miles at a rate of 10 miles/hr. (500 calorie burned.) It was observed that his breath acetone increased to 200 nM on the next day (day 12) It was found that his breath acetone dropped again to 100 nM when he stopped his physical exercise. This increase in breath acetone in conjunction with exercise suggests that it may be possible to correlate the number of calories burned by exercise with increased breath acetone levels. It has been found that excessive coffee or tea intake also enhances breath acetone production during dieting.

EXAMPLE 28

In this example, the antiketotic effect of dietary "cheating" was measured It was observed that dieters consuming a high carbohydrate meal by mistake lowered their breath acetone levels appreciably within a few hours. Subjects participating on the diet of Example 27 for 2 weeks or fasting for 12 hours consumed an 8 ounce can of ENSURE (Ross Laboratories, Columbus, Ohio) containing 250 calories and 36 grams of carbohydrate. The breath acetone of those consuming the product dropped by about 20% after one hour and by about 30% after 3 hours. Similarly, when the test subjects discontinued the diet program and ate a high calorie diet (800 calorie, 100 grams of carbohydrate and 20 to 40 grams fat), a drop of approximately 40% in breath acetone was observed in 5 hours. Within 24 hours, the breath acetone concentration dropped to the pre-diet level.

EXAMPLE 29

In this example, the relationship between development of ketosis (breath acetone) and caloric intake was studied. The results are shown in Table 9 below. As may be observed, the increase in breath acetone is directly proportional to the intake of calorie.

TABLE 9
EFFECT OF CALORIE INTAKE ON KETOSIS DEVELOPMENT

| Calorie Intake[a] | Breath Acetone Level (times normal x) | | |
|---|---|---|---|
| | Day 1 | Day 2 | Day 3 |
| 0 | 4x | 16x | — |
| 600-700 | 1.5x | 6x | 13x |
| 1100-1300 | 1.5x | 4x | 8-10x |
| 2000 | 1.1x | 2.4x | 4x |

[a]Diet comprised of high-protein and less than 20 gm carbohydrates/day was used in this study.

EXAMPLE 30

In this example, a diet study was conducted wherein breath acetone concentrations were measured for a group of dieting individuals utilizing the devices produced according to the methods of Examples 10 and 11 as well as by a gas chromatograph. A gas chromatograph was also utilized to measure blood head-space acetone concentrations. Weight, total body water and total body fat were periodically determined for the subjects of the study.

The study was limited to normal, healthy male and female subjects, between the ages of 24 and 54, with no chronic medical disorder except obesity Fifty-eight volunteers, (20 male and 38 female) participated in the diet study in three groups. Each study period was for 30 consecutive days, excluding weekends and holidays. Twenty volunteers, (10 male and 10 female) were included in the non-dieting control group. This study continued for 19 days excluding weekends and holidays. The participants were between 10% and 30% above their ideal body weight as determined by age/sex/frame/height/weight and Metropolitan Life Insurance Company tables. The participants had complete physical examinations including blood and urine analysis before entering the study, in the middle of and at the end of the study period.

Two diet plans, one providing 1,000 calories per day and another providing 1,200 calories per day were developed for this study by a physician and a consulting dietician. The 1,000 calorie diet included 60-80 gm protein, 90-130 gm carbohydrate and 22-24 gm fat per day. The 1,200 calorie diet included 80-110 gm protein, 113-147 gm carbohydrate and 25-47 gm fat per day. The Harris-Benedict equation was employed to determine the basal energy expenditure (BEE) of each participant before entering the study and the selection of the diet plan was made by the resident dietician according to their BEE requirements The volunteers refrained from any strenuous physical activity during the entire study period and pedometer was provided to each dieter to record the daily number of steps taken.

Data collected during the diet study allowed correlation of blood and breath acetone concentrations. In addition, the data allowed comparison of breath acetone concentrations as measured by a gas chromatograph and by devices prepared according to the methods of Examples 10 and 11.

According to the procedure, blood acetone measurements of the dieting population were performed on days 1, 2, 16, 23 and 30, and for the non-dieting group, the measurements were made on days 3, 10 and 17. Gas chromatographic head-space analysis was carried out according to the method of Van Stekelenburg and Koorevaar, Clin. Chim. Acta, 34, 305-310, 1971 to measure blood acetone concentrations. Breath acetone concentrations were determined by using a gas chromatograph and by means of breath acetone devices produced according to the methods of Examples 10 and 11.

Figure 10:
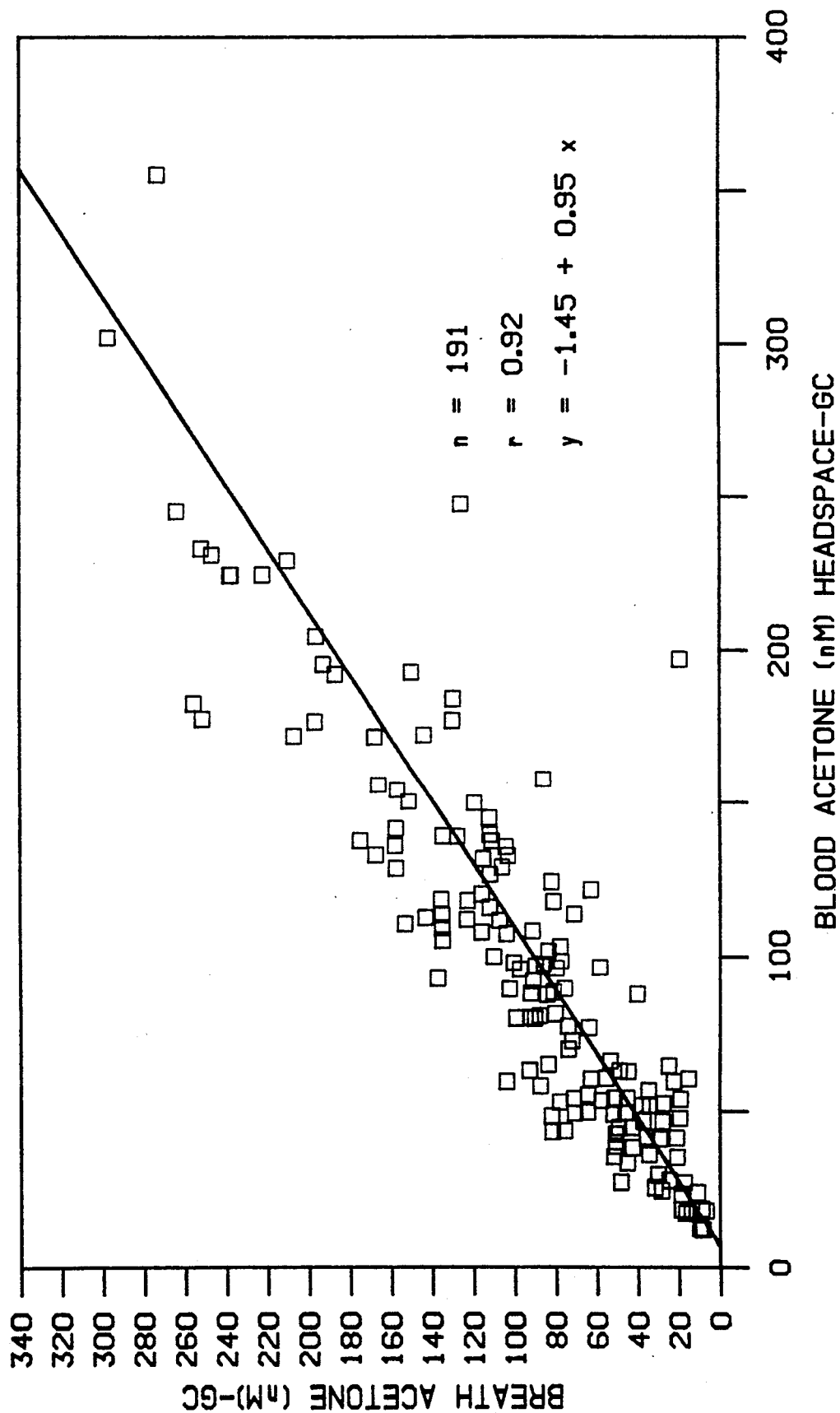
FIG. 10 is a graph illustrating the relationship between breath acetone concentrations and blood headspace acetone concentrations measured by gas chromatograph.

FIG. 10 shows the comparison of breath acetone concentrations (y-axis) to acetone concentrations of blood head-space (x-axis) in dieting and non-dieting groups. Analysis of this data by linear regression techniques provides a formula of $y = 1.45(x) + 0.954$, where x=blood acetone head-space concentration (nm) and y=breath acetone concentrations (nM). The data has a correlation coefficient (r) of 0.92.

Figure 11:
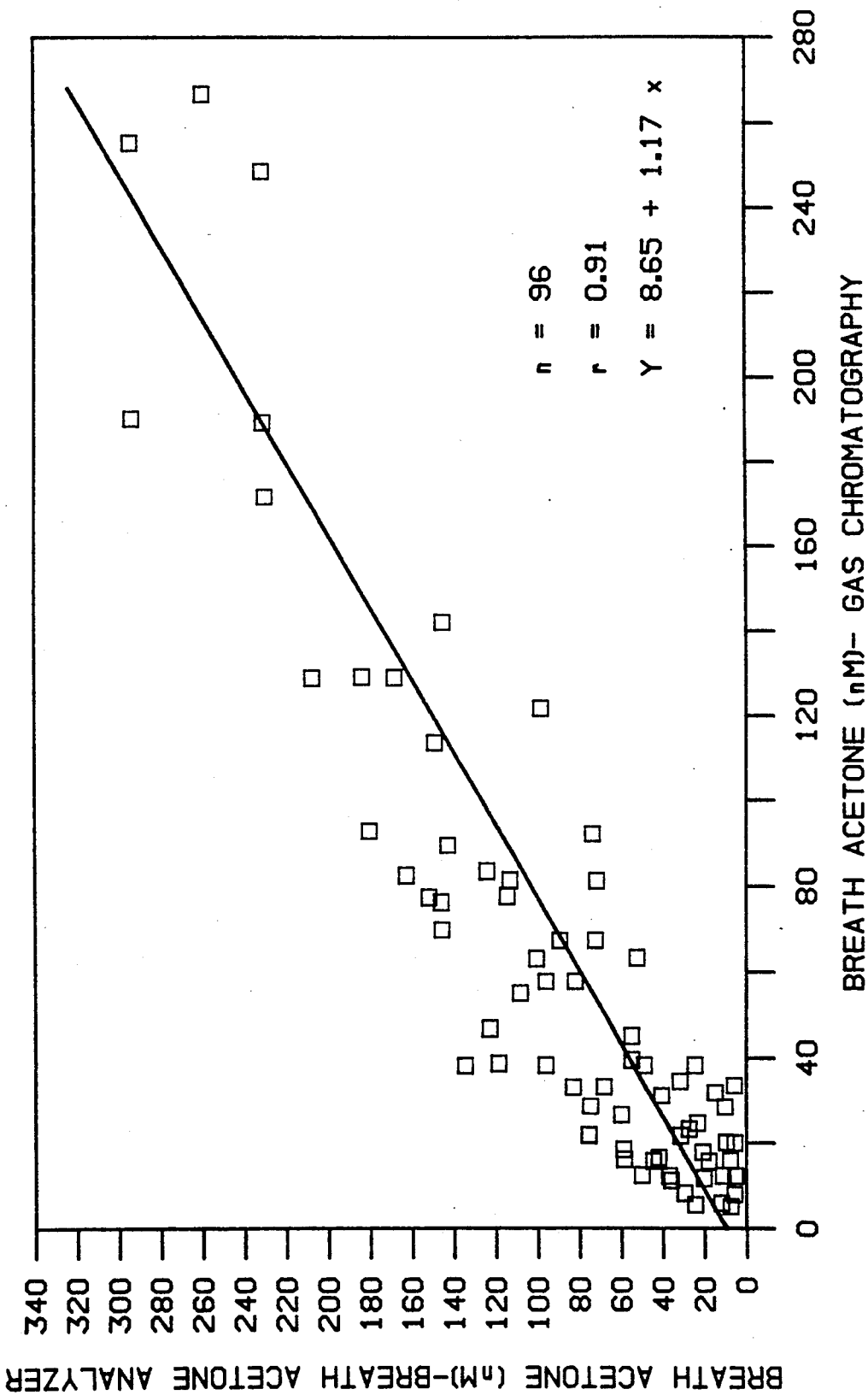
FIG. 11 is a graph illustrating the relationship between breath acetone concentrations as measured by a gas chromatograph and by devices according to the invention.

FIG. 11 shows the comparison of breath acetone concentration of dieting and non-dieting volunteers determined by gas chromatography (x-axis) and by devices prepared according to Examples 10 and 11 (y-axis). The column heights obtained from the breath analyzer devices of the invention were converted to nM acetone concentrations using the standard curve specific for that lot of analyzer columns. Analysis of the data by linear regression techniques provides a formula of $y = 1.173(x) + 8.65$, where x=breath acetone concentration (nM) as calculated by gas chromatography and y=breath acetone concentration (nM) as calculated by devices prepared according to Examples 10 and 11. The data has a correlation coefficient (r) of 0.91.

Data collected during the diet study also allowed improved correlations to be made between the rate of fat loss and breath acetone concentrations. According to this example, total body water and body fat determinations were made by means of bioelectrical impedance instrumentation. According to the experimental procedure, five breath samples were collected from each experimental subject each day immediately upon awakening. Three of the samples were promptly assayed for breath acetone by each volunteer using a breath acetone analyzer prepared according to the methods of Examples 10 and 11. The remaining two samples were analyzed by trained personnel. One was used to measure breath acetone concentration with a breath acetone analyzer device of the invention performed by a trained technician and the other assayed by gas chromatography. Whole body weights were measured by the volunteers daily immediately upon awakening, after defecation and urination. For each determination, the volunteers weighed themselves in their own home with a precision scale five consecutive times. The scales were calibrated at the beginning and end of each study period. Total body water and body fat determinations were performed on each volunteer, five days a week (Monday-Friday) in the morning before breakfast, with a Bioelectrical Impedance Analyzer Model BIA-101 (RJL Systems, Inc., Detroit, Mich.).

Figure 12:
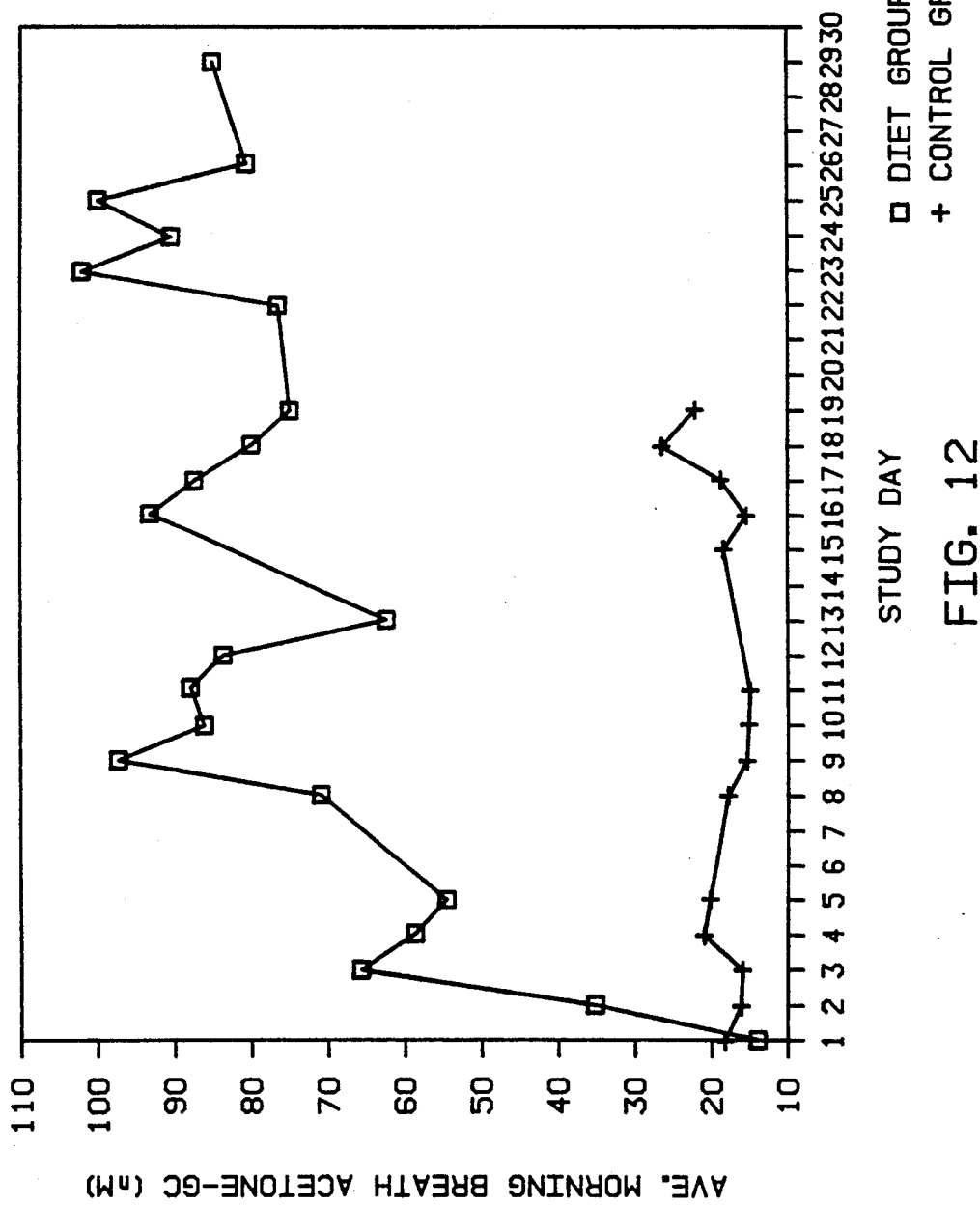
FIG. 12 is a graph illustrating the average morning breath acetone concentration for a dieting and a non-dieting population.
Figure 13:
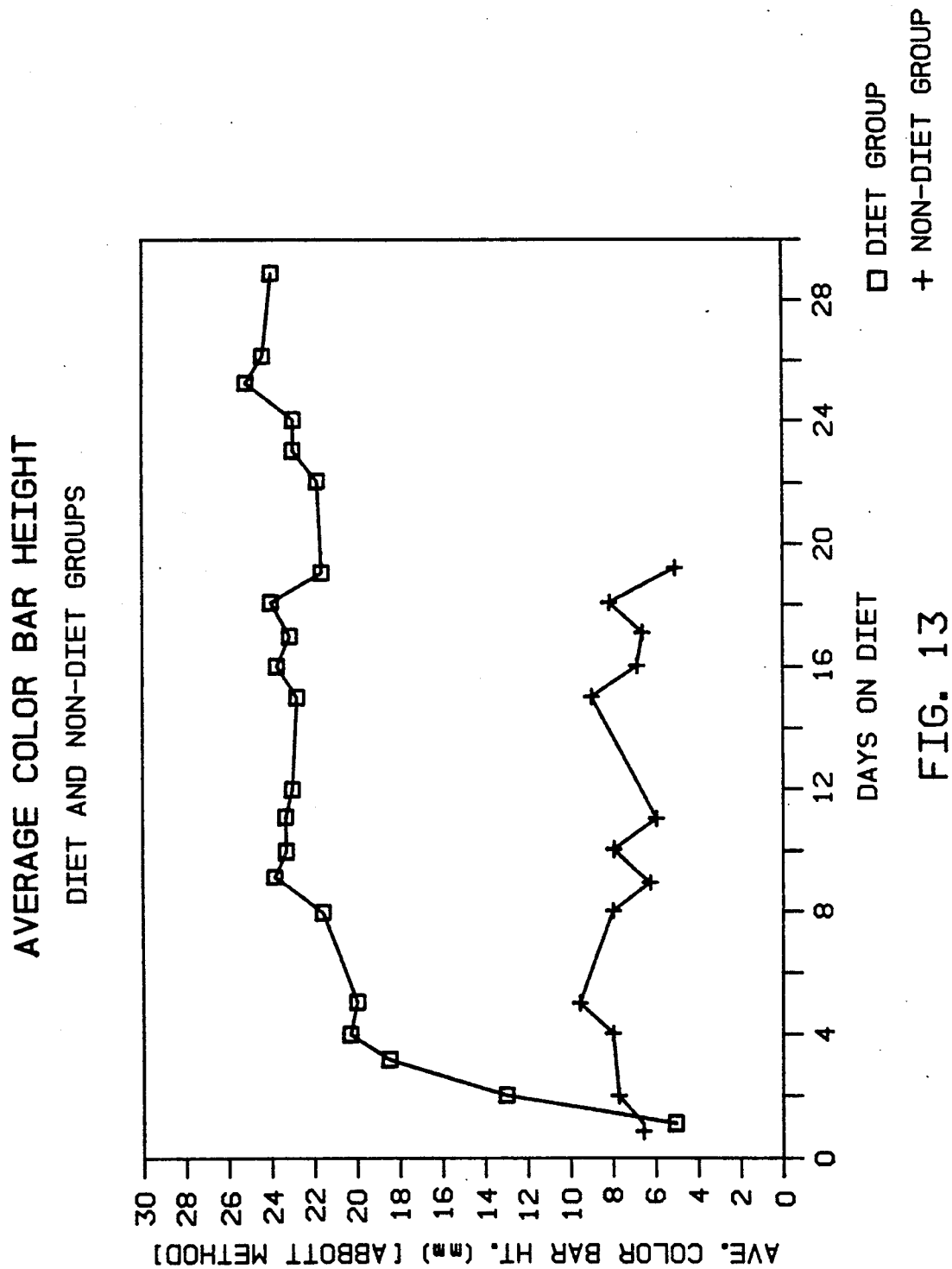
FIG. 13 is a graph illustrating the average height of an indicator color bar in breath acetone measurement devices according to the invention for a dieting and for a non-dieting population.

During the course of this study, the breath acetone concentration of all subjects increased during the first few days of the diet, reached a plateau after approximately seven days and remained elevated during the course of the 30 day study. FIGS. 12 and 13, respectively, show the average cumulative breath acetone concentration and column color bar height during the 30 day study for the 58 dieting volunteers and the 20 non-dieting (control) volunteers. The average column height of the dieting population ranged between about 22 to 24 mm (275-300 nM acetone concentration), compared to the non-dieting population average which ranged between about 5 to 10 mm (17-27 nM acetone concentration).

Figure 14:
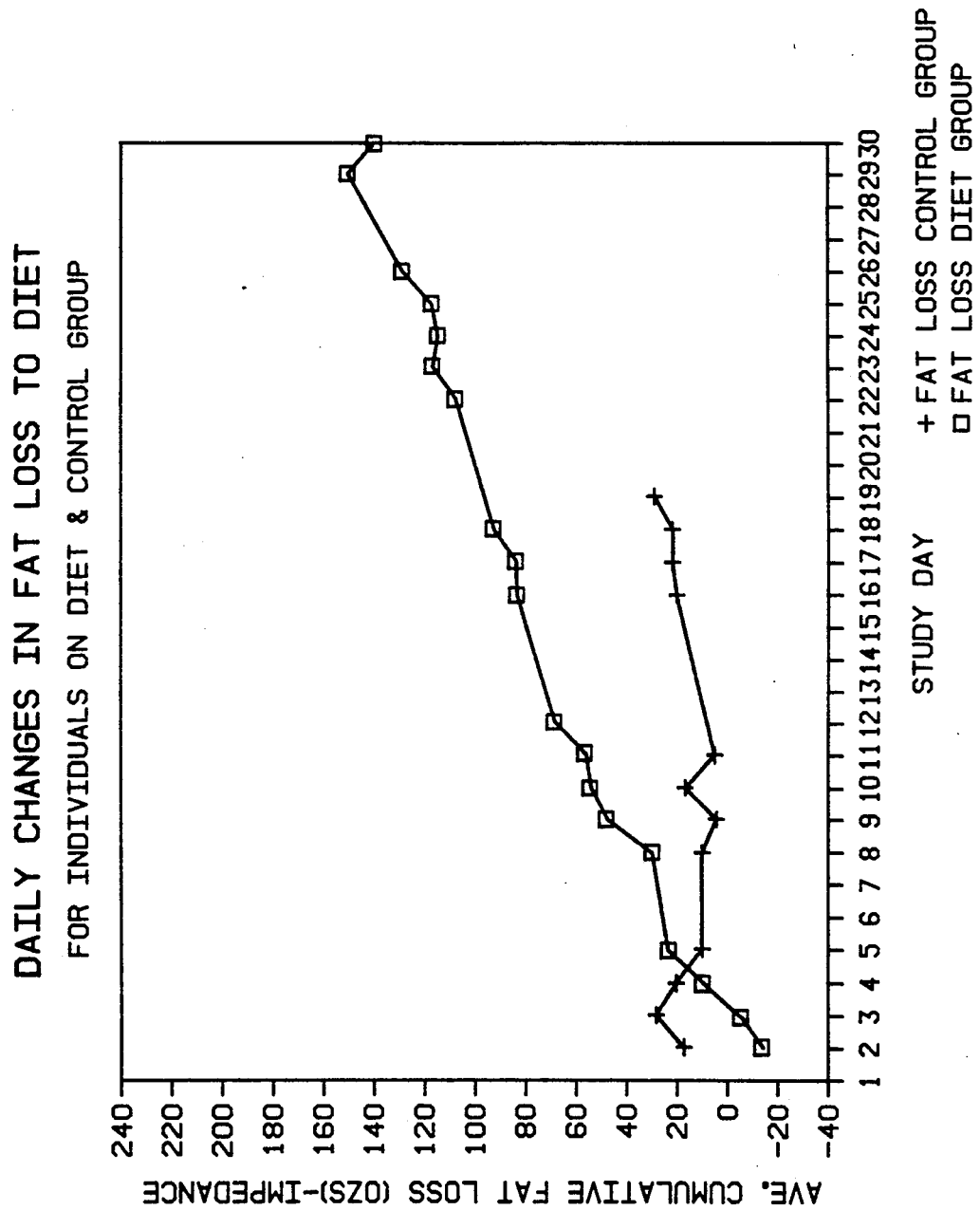
FIG. 14 is a graph illustrating the average cumulative fat loss for a dieting and for a non-dieting population.

The study also demonstrated that all subjects lost fat while on the study diet. The total fat loss was determined by body composition analysis using electrical impedance. FIG. 14 shows the average cumulative fat loss during the course of the 30 day study. The total average cumulative fat loss was approximately 150 ounces for the 30 day period, i.e., approximately 5 ounces fat loss per day, per volunteer.

Figure 15:
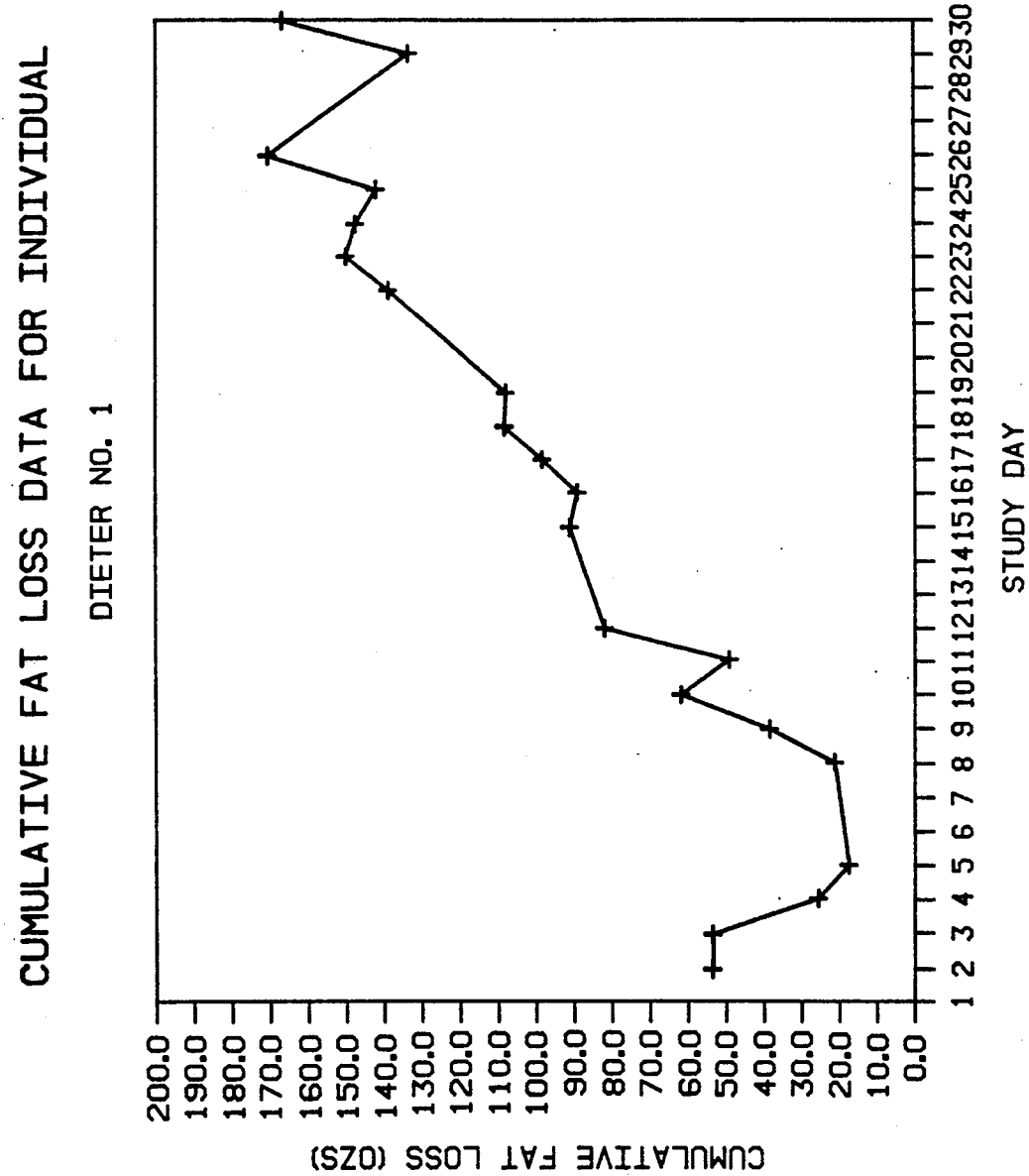
FIG. 15 is a graph illustrating the cumulative fat loss for a first individual dieter.
Figure 16:
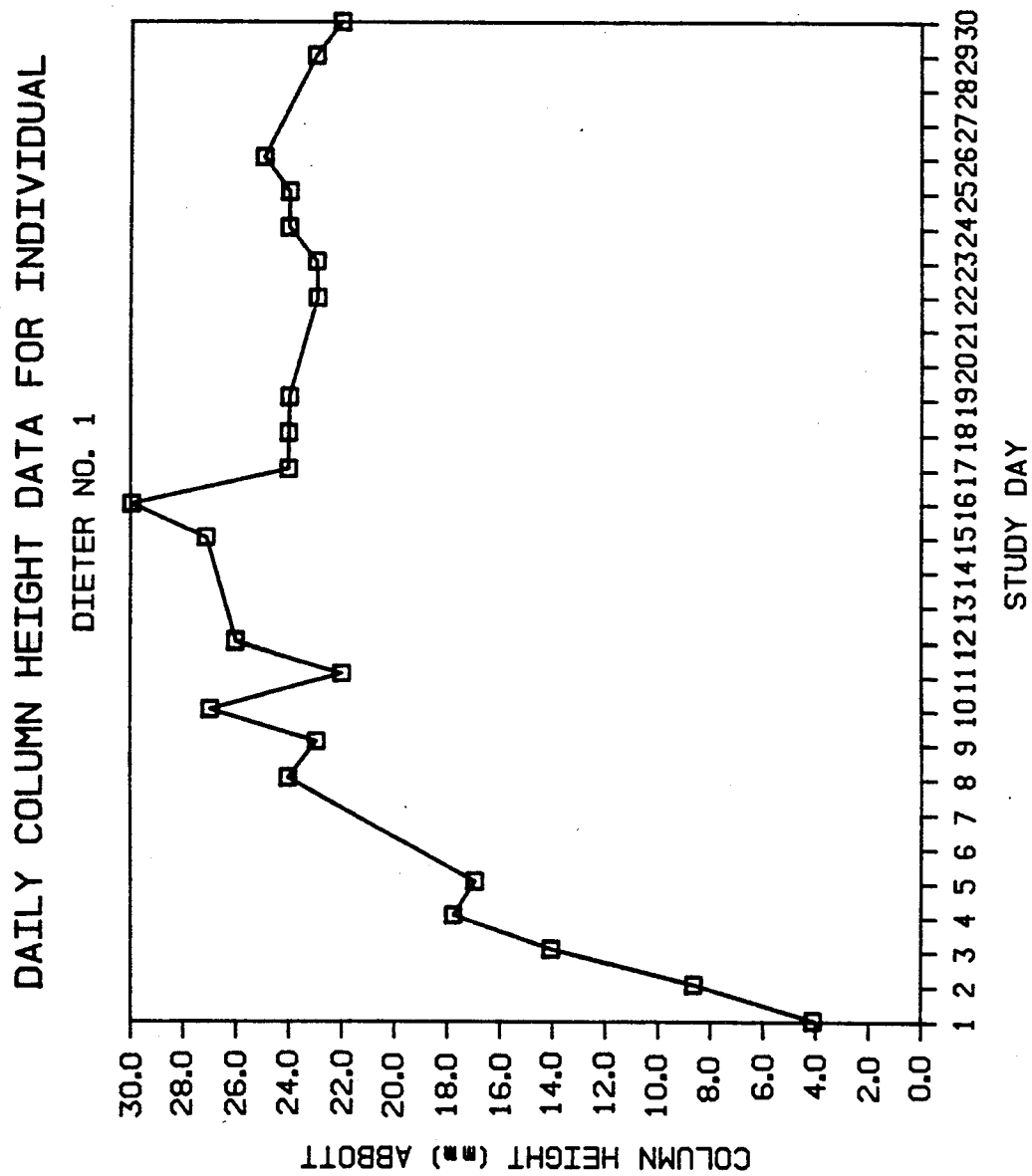
FIG. 16 is a graph illustrating the daily height of an indicator color bar in breath acetone measurement devices according to the invention for the first individual dieter monitored in FIG. 15.
Figure 17:
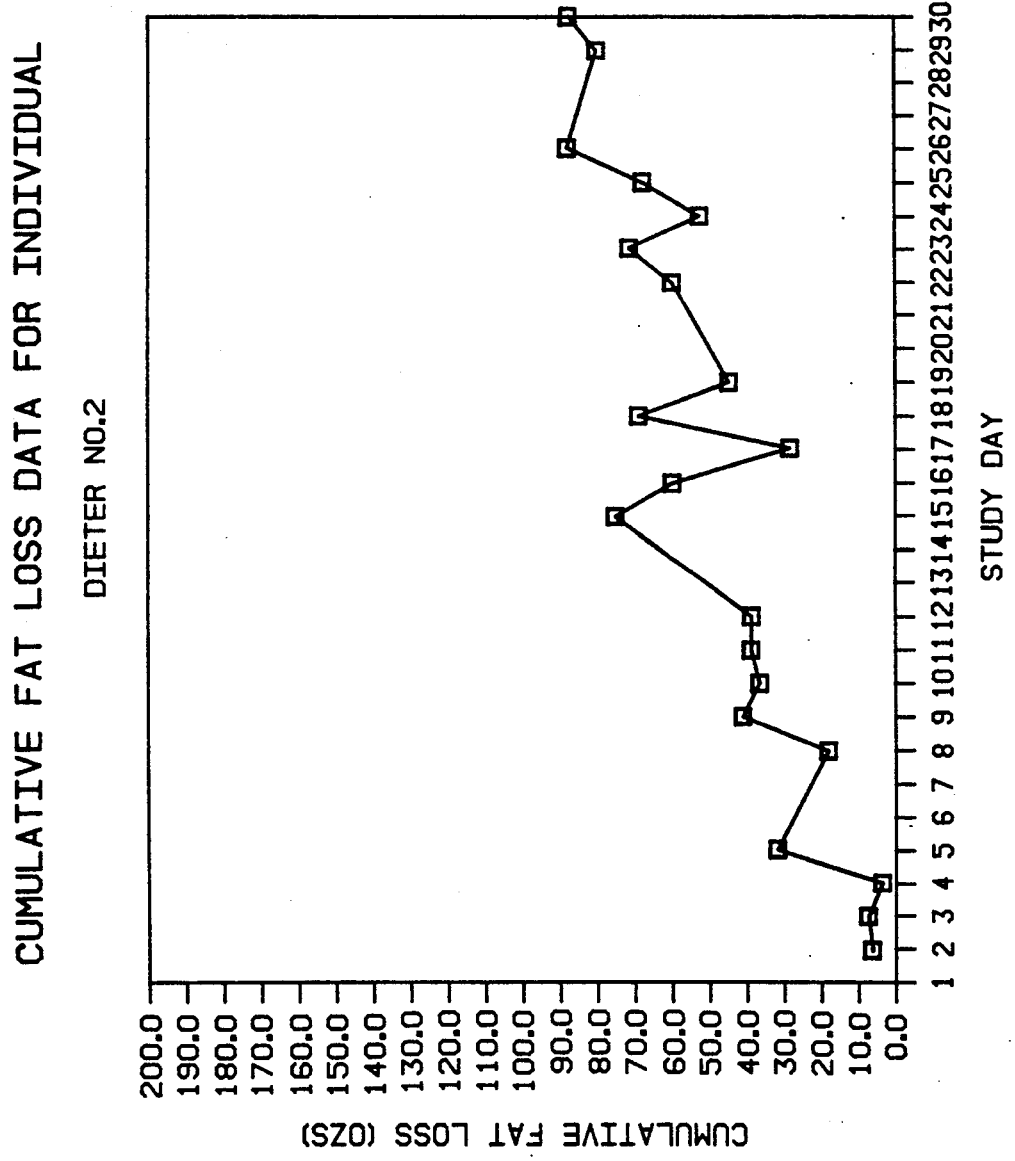
FIG. 17 is a graph illustrating the cumulative fat loss for a second individual dieter.
Figure 18:
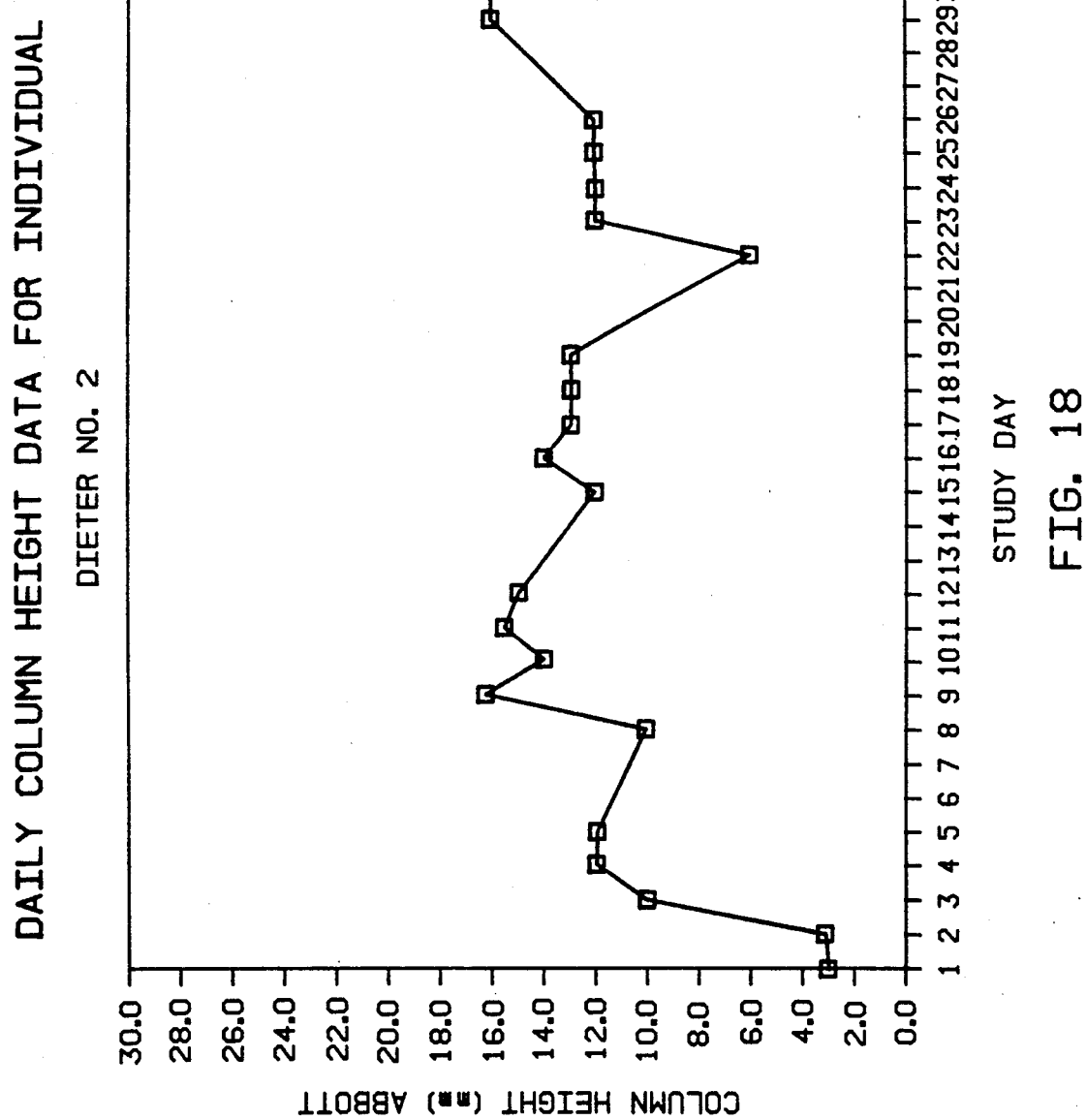
FIG. 18 is a graph illustrating the daily height of an indicator color bar in breath acetone measuring devices according to the invention for the second individual dieter monitored in FIG. 17.
Figure 19:
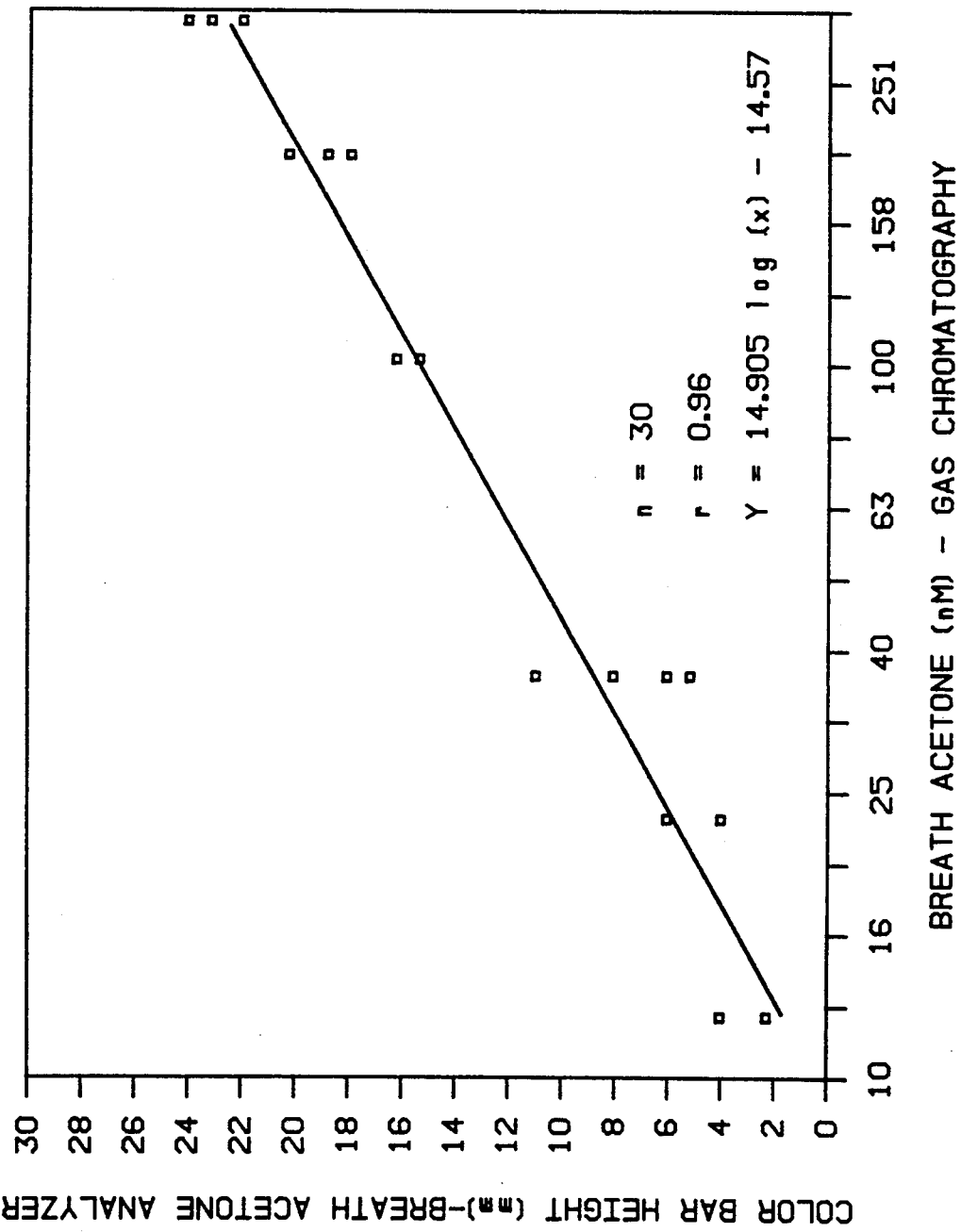
FIG. 19 is a graph illustrating the relationship between the concentration of breath acetone and the height of an indicator color bar in breath acetone measuring devices according to the invention.

It is important to note that the rate of fat loss was not the same for all participant dieters. To illustrate this, the individual profiles of two dieters are shown in FIGS. 15 and 16, together and 17 and 18 together. In FIG. 16, (Dieter 1), the column heights, as determined by the breath acetone analyzer devices of the invention, rose progressively from day 1 and reached a plateau on day 8. The column heights of this dieter remained elevated over 22 mm, corresponding to a breath acetone concentration approximately of 250 nM (FIG. 19). The total loss of body fat was 165 ozs. (10.3 lbs) (FIG. 15) or approximately 5.5 ounces per day. In FIG. 16, (Dieter 2), the column heights rose progressively from day 2 and reached a plateau on day 4. In contrast to Dieter 1, the average column height was reduced to approximately 13 mm. A reduced cumulative fat loss of 86 ounces, or approximately 3 ounces per day, corresponding to a breath concentration of approximately 70 nM (FIG. 19), was also observed for Dieter 2 (FIG. 17).

Individuals in a normal, healthy and non-dieting population have a breath acetone concentration of 15 nM with S.D. of 11 (N=78). This value was calculated from the day 0 baseline level for the dieting (N=58) and non-dieting groups. A threshold level of 37 nM acetone (above which indicates that the patient is losing fat) was calculated on the basis of the average breath acetone concentration of non-dieting subjects plus 2 S.D. The threshold level is indicated on the Diet Progress Chart.

The column height corresponding to the 37 nM acetone threshold level will vary slightly for each lot of columns and this lot specific adjustment is incorporated into a lot specific Diet Progress Chart, an example of which is illustrated in FIG. 21a.

Figure 20:
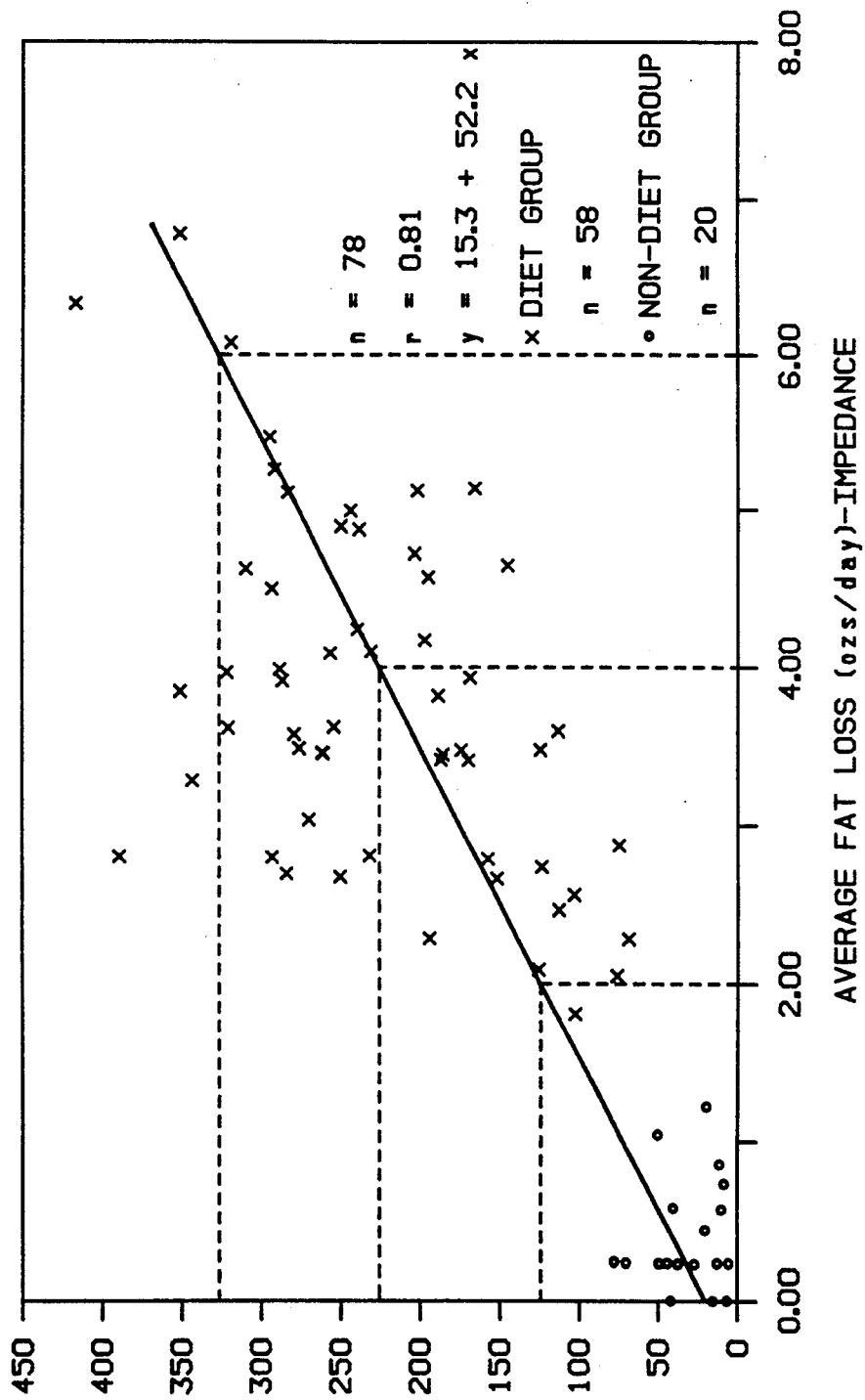
FIG. 20 is a graph illustrating the relationship between breath acetone concentrations and the rate of fat loss.

The average daily breath acetone concentration during the "plateau" phase of the study period (approximately days 8-30) was calculated for each volunteer (dieter and non-dieter) from daily determinations using devices produced according to the procedure of Examples 10 and 11 and a gas chromatograph. These values are shown in Table 9 along with the calculated average daily rate of fat loss determined by impedance over the same time period. A correlation of breath acetone concentrations using the Breath Acetone Analyzer and rate of fat loss is shown in FIG. 20. Analysis of the data by linear regression techniques provides a formula of: Rate of fat loss (oz/day)=(breath acetone conc. (nM)−15.3)/52.2. The formula has a correlation coefficient (r) of 0.8. The results demonstrate that the level of breath acetone measured by the devices of the invention is indicative of the relative rate of fat loss in the patient.

According to a method for use of the devices of the present invention, the acetone concentration of a breath sample may be determined by matching the observed column color zone height with a scale on the left side of a "Diet Progress Chart" shown in FIG. 21a. The scale is correlated to breath acetone concentration, which is itself correlated to the rate of fat loss. The correlation between column color zone height and breath acetone may be adjusted from lot to lot of the test device according to quality control techniques. In the case of the "Diet Progress Chart" of FIGS. 21a and 21b, quality control considerations indicated that a column height of 9.5 mm correlated to an acetone concentration of 120 nM, a column height of 7 mm correlated to an acetone concentration of 220 nM and a column height of 30 mm correlated to an acetone concentration of 330 nM. The subject plots the nM acetone concentration reading on the graph daily. All normal subjects should be below the threshold acetone concentration while not dieting. As the diet continues, the breath acetone concentration will rise for several days and then plateau. The rate of fat loss can be estimated by a scale on the right side of the graph. Non-dieting normal healthy people should have readings in the zone which is below the threshold line. The 0 zone indicates less than 2 ounces of fat loss/day. The + zone estimates a rate of fat loss of 2-4 ounces/day and the ++ zone estimates a rate of fat loss of 4-6 ounces/day.

FIG. 21b illustrates the actual data of an individual who was on a 1,000 caloric diet program for 30 days. The acetone concentration as determined from the measured column color zone height was plotted daily on the graph. As can be seen from the graph, the column heights (nM acetone concentrations) rise progressively from day 1 and exceeded the threshold mark on day 3. The nM acetone concentrations remained elevated in most of the days and fluctuated within the ++ zone. The graph indicates that this dieter remained above the threshold zone (4-6 ounces of fat loss per day). One can estimate the amount of fat loss during the 30 day period to be approximately between 120-180 ounces (4-6 ounces per day). The actual amount of fat loss over the 30 day period calculated using impedance measurements was 165 ounces.

Normal, healthy and non-dieting individuals have an average breath acetone concentration of 15 nM with a S.D. of 11 (N=78). The range varies between 6 to 30 nM in this population. The "threshold level" was calculated to be 37 nM acetone concentration of the basis of average breath acetone concentration plus 2 S.D. Subjects whose breath acetone concentration is below 37 nM are expected not to lose fat (less than 2 ounces/day). Individuals who consume a mixed 1,000-1,200 caloric diet can expect breath acetone concentrations above the threshold level corresponding to a fat loss rate of greater than two ounces per day. The rate of fat loss may not be the same for each individual. Those with a higher metabolic rate can expect greater fat loss.

TABLE 10

Average Breath Acetone Concentration and Fat Loss (Day 8-30)

| I.D. Number (Patient/Group) | Acetone Conc. (nM) | Fat Loss Imp. Oz/Day | I.D. Number (Patient/Group) | Acetone Conc. (nM) | Fat Loss Imp. Oz/Day |
|---|---|---|---|---|---|
| 1C1 | 163 | 5.2 | 1C3 | 121 | 2.1 |
| 2C1 | 120 | 3.42 | 2C3 | 279 | 3.69 |
| 3C1 | 61 | 2.28 | 3C3 | 144 | 2.72 |
| 4C1 | 264 | 4.17 | 4C3 | 275 | 3.05 |
| 5C1 | 137 | 4.72 | 5C3 | 380 | 2.76 |
| 6C1 | 302 | 5.61 | 6C3 | 242 | 4.97 |
| 7C1 | 293 | 4.4 | 7C3 | 223 | 4.09 |
| 8C1 | 70 | 2.8 | 8C3 | 416 | 6.32 |
| 9C1 | 177 | 3.79 | 9C3 | 159 | 3.92 |
| 10C1 | 188 | 4.17 | 10C3 | 249 | 4.89 |
| 11C1 | 121 | 2.73 | 11C3 | 259 | 2.75 |
| 12C1 | 110 | 2.49 | 12C3 | 263 | 3.53 |
| 13C1 | 62 | 2.27 | 13C3 | 317 | 6.09 |
| 14C1 | 84 | 3.13 | 14C3 | 290 | 3.98 |
| 15C1 | 162 | 3.53 | 15C3 | 290 | 4.01 |
| 16C1 | 232 | 3.31 | 16C3 | 257 | 3.72 |
| 17C1 | 153 | 2.81 | 17C3 | 324 | 3.64 |
| 18C1 | 105 | 2.54 | 18C3 | 283 | 2.7 |
| 1C2 | 185 | 2.36 | 19C3 | 281 | 5.08 |
| 2C2 | 347 | 3.9 | 20C3 | 200 | 5.18 |
| 3C2 | 339 | 3.31 | 1C4 | 44 | 0 |
| 4C2 | 276 | 3.6 | 2C4 | 70 | 0.16 |
| 5C2 | 177 | 3.5 | 3C4 | 7 | 0.8 |
| 6C2 | 343 | 6.62 | 4C4 | 9 | 0 |
| 7C2 | 97 | 1.85 | 5C4 | 7 | 0.16 |
| 8C2 | 68 | 2.1 | 6C4 | 51 | 1.12 |
| 9C2 | 64 | 3.58 | 7C4 | 7 | 0.16 |
| 10C2 | 294 | 2.76 | 8C4 | 39 | 0.16 |
| 11C2 | 202 | 4.8 | 9C4 | 4 | 0.64 |
| 12C2 | 322 | 4.03 | 10C4 | 17 | 0.16 |
| 13C2 | 233 | 4.27 | 11C4 | 14 | 0.32 |
| 14C2 | 88 | 3.05 | 12C4 | 18 | 1.28 |

TABLE 10-continued

| Average Breath Acetone Concentration and Fat Loss (Day 8-30) | | | | | |
|---|---|---|---|---|---|
| I.D. Number (Patient/ Group) | Acetone Conc. (nM) | Fat Loss Imp. Oz/Day | I.D. Number (Patient/ Group) | Acetone Conc. (nM) | Fat Loss Imp. Oz/Day |
| 15C2 | 312 | 4.52 | 13C4 | 18 | 1.28 |
| 16C2 | 105 | 3.53 | 14C4 | 68 | 0.16 |
| 17C2 | 176 | 3.55 | 15C4 | 6 | 0 |
| 18C2 | 239 | 4.84 | 16C4 | 4 | 0.16 |
| 19C2 | 295 | 5.32 | 17C4 | 32 | 0.48 |
| 20C2 | 190 | 4.6 | 18C4 | 44 | 0.16 |
|  |  |  | 19C4 | 5 | 0.48 |
|  |  |  | 20C4 | 48 | 0.16 |

Numerous modifications and variations in practice of the invention are expected to occur to those skilled in the art upon consideration of the foregoing description of preferred embodiments thereof. Consequently, only such limitations should be placed on the invention as appear in the following claims.

What is claimed is:

1. A device for monitoring levels of various components in the breath of a user, comprising:
    a) an outer tubular member having an open first end and a second end;
    b) valve means disposed toward the second end of said outer tubular member;
    c) a breath sample collection means having one end mounted on said outer tubular member and having the other end closed, and having an interior in communication with the inside of said outer tubular member through said valve means; and
    d) a disposable tubular analyzer column containing material reactive to the presence of at least one breath component wherein said column is insertable into and contained within said outer tubular member, co-operates with said valve means to permit breath blown by a user into said outer tubular member to pass through said outer tubular member into said breath sample collection means and to permit said collected breath sample to discharge through the reactive material of said analyzer column.

2. The monitoring device as recited in claim 1 wherein said analyzer column is insertable into and contained within said outer tubular member to a first rotational and axial position for breath collection in which breath blown into said outer tubular member bypasses said reactive material of said analyzer column and passes through said valve means into said breath sample collection means, said analyzer column being rotatable and further insertable to a second rotational and axial position wherein said analyzer column is in communication with said valve means such that a collected breath sample is discharged from breath sample collection means through said valve means into said reactive material of said analyzer column.

3. The monitoring device as recited in claim 2 wherein said analyzer column further comprises a mouthpiece which is receivable in said first open end of said outer tubular member and a reduced-diameter central portion creating a passageway between the inside of said outer tubular member and the outside of said analyzer column, said central portion being connected to said mouthpiece by a wall segment having at least one orifice therein such that, when said analyzer column is in said first position, the breath of a user passes from said mouthpiece through said passageway and said valve means into said breath sample collection means.

4. The monitoring device as recited in claim 2 wherein longitudinally extending rib means are provided on the inner surface of said outer tubular member for guiding said analyzer column when inserted therein.

5. The monitoring device as recited in claim 4 wherein positioning flats are provided on said analyzer column for cooperating with said rib means on said outer tubular member to guide and position said analyzer column during insertion of said analyzer column into said outer tubular member.

6. The monitoring device as recited in claim 4 wherein stop means are provided on at least one of said rib means for engagement by said analyzer column to determine a first axial position of said column.

7. The monitoring device as recited in claim 2 wherein said valve means comprises a housing member, a ball member disposed therein, an O-ring, and a further reduced-diameter end portion of said analyzer column, said further reduced diameter end portion of said column being axially spaced from said O-ring in said first position of the column and, in said second position of the column, passing through and sealingly engaging said O-ring and abutting against said ball.

8. The monitoring device as recited in claim 2 wherein said sample collection means comprises an inflatable/deflatable bag and a flat coil spring is provided on the outer surface of said bag so that, after said bag is inflated and said analyzer column is moved into said second position, said spring coils said bag into its deflated condition with the fixed volume of air being discharged at a substantially constant rate through said reactive material in the analyzer column.

9. The monitoring device as recited in claim 1 wherein said reactive material includes at least one fluid reactant, said tubular analyzer column has a flexible portion adjacent said reactive material and said outer tubular member includes means for squeezing said flexible portion thereby to break an ampule of said fluid reactant disposed in said flexible portion.

10. The monitoring device as recited in claim 9 wherein said means for squeezing comprises an outwardly biased but inwardly movable breaker button mounted in a portable housing surrounding said outer tubular member, said breaker button being in alignment with said flexible portion of the disposable analyzer column and having a stem and head for transferring pressure to said flexible portion.

11. The monitoring device as recited in claim 9 wherein said means for squeezing is axially positioned to break the end of said ampule most closely adjacent said reactive material.

12. A kit for the determination of levels of various components in a user's breath, said kit comprising:
    a) a portable housing with an opening at one end and containing:
        i) an outer tubular member having an open first end and a second end, wherein said outer tubular member is contained within said portable housing such that said open first end of said outer tubular member is in communication with said portable housing opening;
        ii) valve means disposed toward said second end of said outer tubular member; and
        iii) a breath sample collection means having one end mounted on said outer tubular member and having the other end closed, and having an interior in communication with the inside of said outer tubular member through said valve means for collecting a fixed volume of a user's breath; and b) a disposable tubular analyzer column containing material reactive to the presence of at least one breath component, wherein said column is insertable into said outer tubular member through said portable housing opening, co-operates with said valve means to permit breath blown by a user into said outer tubular member to pass through said outer tubular member into said breath sample collection means and to permit said collected breath sample to discharge through the reactive material of said analyzer column.

13. A disposable, tubular analyzer column for use in a blow tube, having an open first end and a valve disposed toward a second end, for monitoring levels of various components in the breath of a user, said analyzer column comprising:

a hollow mouthpiece portion of a diameter permitting partial insertion of said analyzer column into an open first end of a blow tube;

a central portion of reduced-diameter having a wall segment interconnecting said mouthpiece and said reduced-diameter central portion, said central portion housing a volume of reactive material, and said wall segment defining at least one breath passage opening such that when said analyzer column is inserted into said blow tube to a first position, a breath passageway to said valve is formed from inside said mouthpiece through said breath passage opening and through a space formed between an inner wall of said blow tube and an outer wall of said reduced-diameter central portion.

14. The analyzer column as recited in claim 13 wherein said central portion also houses a breakable ampule of liquid reactant adjacent said reactive material, said central portion being flexible enough to permit breaking of said ampule by applying pressure to sid central portion.

15. The analyzer column as recited in claim 13 wherein said tubular analyzer column is further characterized by an end portion opposite said mouthpiece portion, said end portion having a further reduced-diameter which is operably engageable wtih a valve means of said blow tube in a second position of said analyzer column in said blow tube, wherein said valve means comprises a housing member, a ball member disposed therein and an O-ring, said further reduced-diameter end portion of said analyzer column being axially spaced from said O-ring in said first position of said analyzer column and passing through and sealingly engaging said O-ring and abutting against said ball member in said second position of said analyzer column.

* * * * *

UNITED STATES PATENT AND TRADEMARK OFFICE
CERTIFICATE OF CORRECTION

PATENT NO. : 5,174,959                         Page 1 of 4

DATED : December 29, 1992

INVENTOR(S) : S. K. Kundu; S. C. March; R. W. George; and S. Rutnarak

It is certified that error appears in the above-indentified patent and that said Letters Patent is hereby corrected as shown below:

In Column 18, line 15, insert a --.-- after "funnel" and before "The".

In Column 22, line 49, insert a --.-- after "forms" and before "vapors".

In Column 23, line 38, insert a --.-- after "sample".

In Column 24, line 9, insert a --.-- after "(33)" and before "Ketones".

In Column 24, line 12, insert a --.-- after "(37)" and before "When".

In Column 24, line 16, insert a --.-- after "(38)" and before "There".

In Column 24, line 26, insert a --.-- after "assay" and before "The".

In Column 24, line 31, insert a --.-- after "phthalate" and before "Glass".

In Column 24, line 36, insert a --.-- after "ampule" and before "Alternatively".

In Column 25, line 12, insert a --.-- after "(DMSO)" and before "Suitable".

In Column 25, line 37, delete [Va.] and insert --Ca.--.

In Column 25, line 53, insert a --.-- after "bottle" and before "The".

In Column 25, line 56, insert --from-- after "moisture".

In Column 25, line 61, delete [F] after "' ".

In Column 25, line 66, insert --of-- before "calcium".

UNITED STATES PATENT AND TRADEMARK OFFICE
CERTIFICATE OF CORRECTION

PATENT NO. : 5,174,959   Page 2 of 4
DATED : December 29, 1992
INVENTOR(S) : S. K. Kundu; S. C. March; R. W. George; and S. Rutnarak It is certified that error appears in the above-indentified patent and that said Letters Patent is hereby corrected as shown below:

In Column 26, line 1, insert a --.-- after "samples" and before "Other".

In Column 26, line 38, insert a --.-- after "ran)" and before "Bolton".

In Column 27, line 47, insert a --.-- after "(94)" and before "As".

In Column 27, line 68, insert --the tube (86). All four of the ribs (110) and (112)-- after and before "converge".

In Column 28, line 21, insert a --.-- after "hereinafter" and before "The".

In Column 28, line 37, insert a --.-- after "(134)" and before "The".

In Column 29, line 20, insert a --.-- after "(148)".

In Column 29, line 48, insert a --.-- after "(146)" and before "Obviously".

In Column 30, line 19, insert a --.-- after "(122)" and before "The".

In Column 30, line 24, insert a --.-- after "(90)" and before "As".

In Column 30, line 51, insert a --.-- after "(108)" and before "This".

In Column 35, line 40, insert a --.-- after "diffusion" and before "The".

In Column 36, line 56, insert a --.-- after "surfaces" and before "Suitable".

In Column 38, line 62, insert a --.-- after "mg/dl".

In Column 40, line 68, insert a --.-- after "detector" and before "The".

UNITED STATES PATENT AND TRADEMARK OFFICE
CERTIFICATE OF CORRECTION

PATENT NO. : 5,174,959
DATED : December 29, 1992
INVENTOR(S) : S. K. Kundu; S. C. March; R. W. George; and S. Rutnarak It is certified that error appears in the above-indentified patent and that said Letters Patent is hereby corrected as shown below:

In Column 41, line 9, insert a --.-- after "peaks" and before "Calibrations".

In Column 41, line 16, delete the space between "sample" and the ".". Insert 2 spaces after the "." and before "A".

In Column 41, line 17, insert a --.-- after "purposes".

In Column 41, line 40, insert a --.-- after "method" and before "It".

In Column 43, line 48, insert a --.-- after "(FIG. 9)" and before "It".

In Column 44, line 10, insert a --.-- after "jogging)" and before "Immediately".

In Column 44, line 23, insert a --.-- after "(day 12)" and before "It".

In Column 45, line 14, insert a --.-- after "obesity" and before "Fifty".

In Column 48, Table 10, line 9C2, change "Acetone Conc. Col. to "164" instead of "64".

In Column 49, line 18, add an --s-- to "description" to read "descriptions".

UNITED STATES PATENT AND TRADEMARK OFFICE
CERTIFICATE OF CORRECTION

PATENT NO. : 5,174,959
DATED : December 29, 1992
INVENTOR(S) : S. K. Kundu; S. C. March; R. W. George; and S. Rutnarak It is certified that error appears in the above-indentified patent and that said Letters Patent is hereby corrected as shown below:

In Column 52, line 12, delete [sid] and insert --said-- after "to".

Signed and Sealed this

Thirtieth Day of August, 1994

Attest:

BRUCE LEHMAN

Attesting Officer        Commissioner of Patents and Trademarks